United States Patent
Bergstrom et al.

(10) Patent No.: US 9,848,774 B2
(45) Date of Patent: Dec. 26, 2017

(54) SYSTEM AND METHODS FOR IMPROVED DIABETES DATA MANAGEMENT AND USE EMPLOYING WIRELESS CONNECTIVITY BETWEEN PATIENTS AND HEALTHCARE PROVIDERS AND REPOSITORY OF DIABETES MANAGEMENT INFORMATION

(75) Inventors: Chris Bergstrom, Ramsey, NJ (US); Jay Butterbrodt, Andover, MA (US); Alan W. Fiedler, Wayne, NJ (US); Barry Ginsberg, Wyckoff, NJ (US); Tim H. Gordon, Rivervale, NJ (US); Paul Upham, Jersey City, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 493 days.

(21) Appl. No.: 13/601,163

(22) Filed: Aug. 31, 2012

(65) Prior Publication Data

US 2013/0030841 A1   Jan. 31, 2013

Related U.S. Application Data

(62) Division of application No. 12/293,120, filed as application No. PCT/US2007/007314 on Mar. 23, 2007, now Pat. No. 8,285,487.
(Continued)

(51) Int. Cl.
*G06Q 50/00* (2012.01)
*A61B 5/00* (2006.01)
(Continued)

(52) U.S. Cl.
CPC ........ *A61B 5/0002* (2013.01); *A61B 5/14532* (2013.01); *A61M 5/14244* (2013.01);
(Continued)

(58) Field of Classification Search
CPC .... G06Q 30/207; G06Q 30/04; G06Q 10/087; G06Q 10/06375; A61B 5/14532; A61B 2562/0295
(Continued)

(56) References Cited

U.S. PATENT DOCUMENTS

| | | |
|---|---|---|
| 4,814,763 A | 3/1989 | Nelson et al. |
| 4,893,270 A | 1/1990 | Beck et al. |

(Continued)

FOREIGN PATENT DOCUMENTS

| | | |
|---|---|---|
| DE | 102004036358 A1 | 2/2006 |
| EP | 1559364 A1 * | 8/2005 |

(Continued)

*Primary Examiner* — Elaine Gort
*Assistant Examiner* — John P Go
(74) *Attorney, Agent, or Firm* — Dickinson Wright PLLC

(57) ABSTRACT

Methods, devices and a system for disease management are provided that employ diagnostic testing devices (e.g., blood glucose meters) and medication delivery devices (e.g., insulin delivery devices) for providing data to a repository in real-time and automatically. Repository data can be analyzed to determine such information as actual test strip use, patient health parameters to outside prescribed ranges, testing and medication delivery compliance, patient profiles or stakeholders to receive promotional items or incentives, and so on. Connected meters and medication delivery devices and repository data analysis are also employed to associate a diagnostic test to a mealtime based on timing of a therapeutic intervention performed by an individual.

29 Claims, 47 Drawing Sheets

Related U.S. Application Data

(60) Provisional application No. 60/784,760, filed on Mar. 23, 2006.

(51) Int. Cl.
*A61B 5/145* (2006.01)
*A61M 5/142* (2006.01)
*G06F 19/00* (2011.01)
*G06Q 50/24* (2012.01)

(52) U.S. Cl.
CPC .......... *G06F 19/322* (2013.01); *G06F 19/345* (2013.01); *G06F 19/3406* (2013.01); *G06F 19/3418* (2013.01); *G06F 19/3468* (2013.01); *G06F 19/3487* (2013.01); *G06Q 50/24* (2013.01); *A61B 2560/0271* (2013.01); *A61B 2560/0456* (2013.01); *A61M 2205/3561* (2013.01); *A61M 2205/3569* (2013.01); *A61M 2205/3576* (2013.01); *A61M 2205/6018* (2013.01); *A61M 2230/201* (2013.01); *G06F 19/3475* (2013.01); *G06F 19/3481* (2013.01); *Y10T 436/144444* (2015.01)

(58) Field of Classification Search
USPC ..................................................... 705/2, 3, 4
See application file for complete search history.

(56) References Cited

U.S. PATENT DOCUMENTS

| | | | |
|---|---|---|---|
| 5,542,420 A | 8/1996 | Goldman et al. | |
| 5,555,191 A | 9/1996 | Hripcsak | |
| 5,619,991 A | 4/1997 | Sloane | |
| 5,772,585 A | 6/1998 | Lavin et al. | |
| 5,835,084 A | 11/1998 | Bailey et al. | |
| 5,905,262 A * | 5/1999 | Spanswick | 250/368 |
| 5,915,240 A | 6/1999 | Karpf | |
| 5,917,812 A | 6/1999 | Antonio et al. | |
| 5,950,632 A * | 9/1999 | Reber et al. | 128/898 |
| 5,953,704 A | 9/1999 | McIlroy et al. | |
| 6,039,688 A | 3/2000 | Douglas et al. | |
| 6,092,102 A | 7/2000 | Wagner | |
| 6,108,635 A | 8/2000 | Herren et al. | |
| 6,157,442 A | 12/2000 | Raskas | |
| 6,197,257 B1 | 3/2001 | Raskas | |
| 6,294,999 B1 | 9/2001 | Yarin et al. | |
| 6,295,506 B1 | 9/2001 | Heinonen et al. | |
| 6,380,858 B1 | 4/2002 | Yarin et al. | |
| 6,413,213 B1 | 7/2002 | Essenpreis et al. | |
| 6,600,997 B2 * | 7/2003 | Deweese et al. | 702/22 |
| 6,670,192 B1 | 12/2003 | Galen et al. | |
| 6,699,188 B2 | 3/2004 | Wessel | |
| 6,844,149 B2 | 1/2005 | Goldman | |
| 6,895,263 B2 * | 5/2005 | Shin et al. | 600/316 |
| 6,923,763 B1 * | 8/2005 | Kovatchev et al. | 600/300 |
| 6,951,728 B2 | 10/2005 | Qian et al. | |
| 6,976,958 B2 | 12/2005 | Quy | |
| 6,988,634 B2 | 1/2006 | Varis | |
| 2001/0028308 A1 * | 10/2001 | De La Huerga | 340/573.1 |
| 2001/0049608 A1 * | 12/2001 | Hochman | 705/3 |
| 2002/0007284 A1 | 1/2002 | Schurenberg et al. | |
| 2002/0007290 A1 * | 1/2002 | Gottlieb | 705/4 |
| 2002/0019707 A1 * | 2/2002 | Cohen et al. | 702/30 |
| 2002/0019749 A1 | 2/2002 | Becker et al. | |
| 2002/0072858 A1 | 6/2002 | Cheng | |
| 2002/0143434 A1 * | 10/2002 | Greeven et al. | 700/236 |
| 2002/0156654 A1 * | 10/2002 | Roe et al. | 705/3 |
| 2003/0032077 A1 | 2/2003 | Itoh et al. | 435/14 |
| 2003/0050537 A1 * | 3/2003 | Wessel | 600/300 |
| 2003/0050799 A1 * | 3/2003 | Jay et al. | 705/2 |
| 2003/0065536 A1 | 4/2003 | Hansen et al. | |
| 2003/0172009 A1 * | 9/2003 | Katou et al. | 705/28 |
| 2003/0195770 A1 | 10/2003 | Fukushima | |
| 2003/0216969 A1 * | 11/2003 | Bauer et al. | 705/22 |
| 2003/0229517 A1 * | 12/2003 | Meserol et al. | 705/2 |
| 2003/0232370 A1 * | 12/2003 | Trifiro | 435/6 |
| 2004/0015132 A1 | 1/2004 | Brown | |
| 2004/0015397 A1 * | 1/2004 | Barry et al. | 705/14 |
| 2004/0054263 A1 | 3/2004 | Moerman et al. | |
| 2004/0078219 A1 | 4/2004 | Kaylor et al. | |
| 2004/0106855 A1 * | 6/2004 | Brown | 600/301 |
| 2004/0117323 A1 * | 6/2004 | Mindala | 705/400 |
| 2004/0142722 A1 * | 7/2004 | Everett | 455/550.1 |
| 2004/0186794 A1 * | 9/2004 | Renz et al. | 705/28 |
| 2004/0193025 A1 * | 9/2004 | Steil et al. | 600/316 |
| 2004/0230502 A1 * | 11/2004 | Fiacco et al. | 705/28 |
| 2005/0010416 A1 | 1/2005 | Anderson et al. | |
| 2005/0038674 A1 * | 2/2005 | Braig et al. | 705/2 |
| 2005/0049179 A1 | 3/2005 | Davidson et al. | |
| 2005/0065464 A1 * | 3/2005 | Talbot et al. | 604/66 |
| 2005/0086071 A1 * | 4/2005 | Fox et al. | 705/2 |
| 2005/0096941 A1 * | 5/2005 | Tong | 705/2 |
| 2005/0108046 A1 * | 5/2005 | Craft | 705/2 |
| 2005/0108061 A1 | 5/2005 | Meserol et al. | |
| 2005/0171815 A1 * | 8/2005 | Vanderveen | 705/3 |
| 2005/0197553 A1 * | 9/2005 | Cooper | 600/365 |
| 2005/0197621 A1 * | 9/2005 | Poulsen et al. | 604/67 |
| 2005/0258242 A1 | 11/2005 | Zarembo | |
| 2006/0010098 A1 | 1/2006 | Goodnow et al. | |
| 2006/0019327 A1 | 1/2006 | Brister et al. | |
| 2006/0036134 A1 | 2/2006 | Tarassenko et al. | |
| 2006/0142648 A1 | 6/2006 | Banet et al. | |
| 2006/0287885 A1 | 12/2006 | Frick | |

FOREIGN PATENT DOCUMENTS

| | | |
|---|---|---|
| JP | 2001-017542 | 1/2001 |
| JP | 2005-267364 | 9/2005 |
| JP | 2006-507912 A | 3/2006 |
| WO | WO 03/015838 | 2/2003 |
| WO | WO-2005093629 | 10/2005 |
| WO | 2006-021566 A2 | 3/2006 |
| WO | 2006-026741 A1 | 3/2006 |
| WO | WO 2006/086423 | 8/2006 |

\* cited by examiner

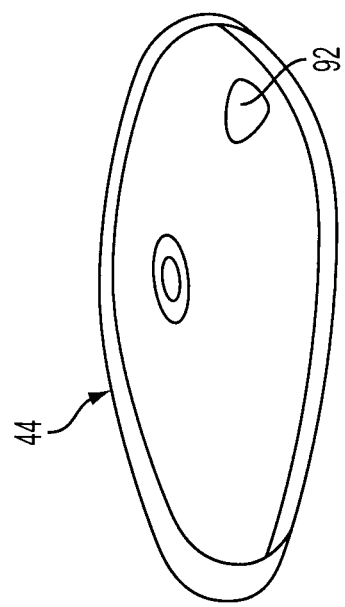
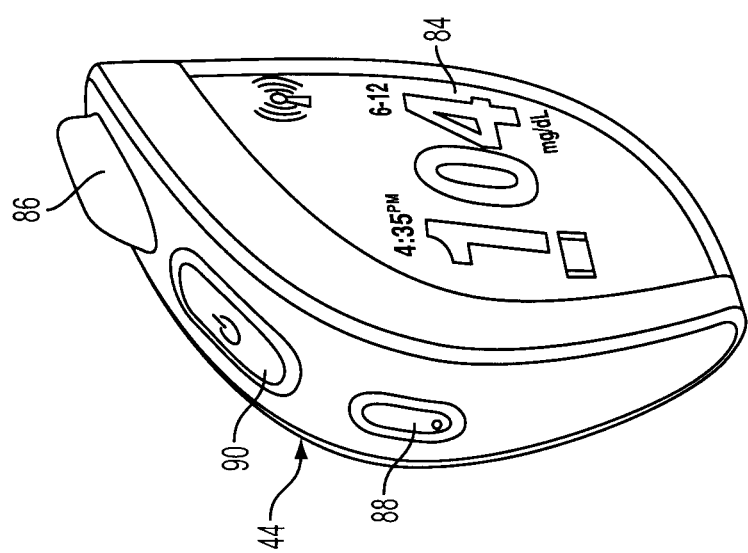

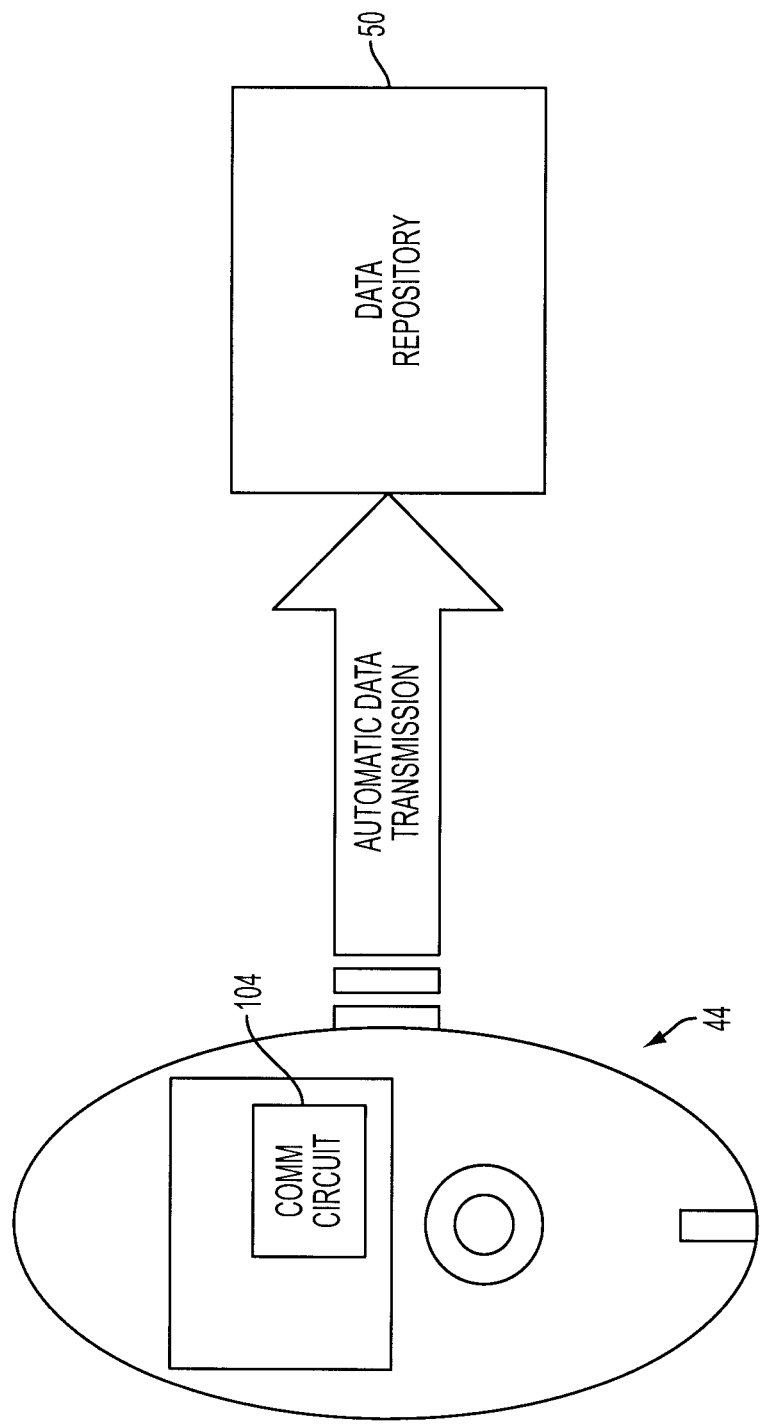

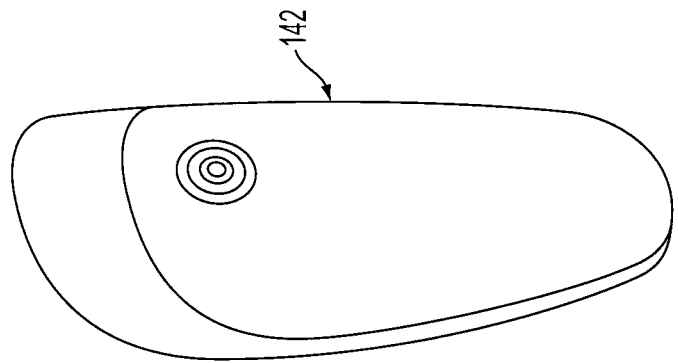
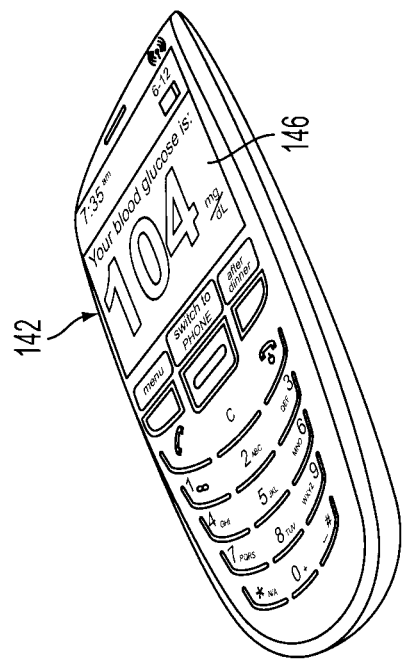
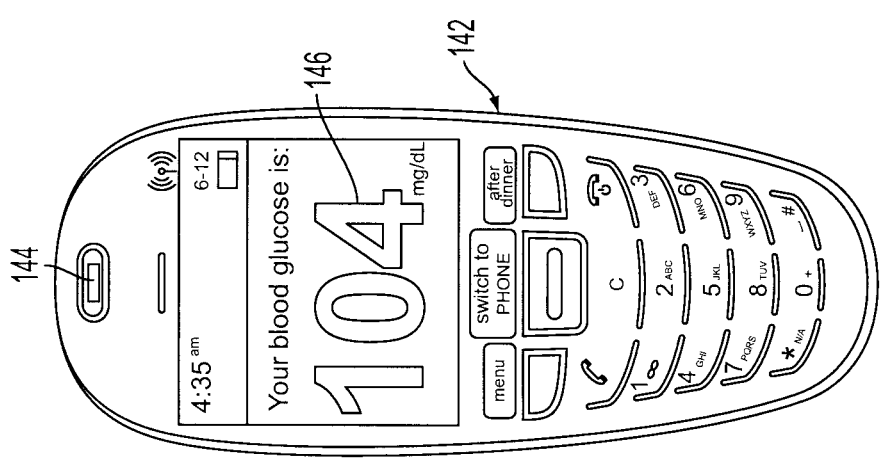
FIG. 13C
FIG. 13B
FIG. 13A

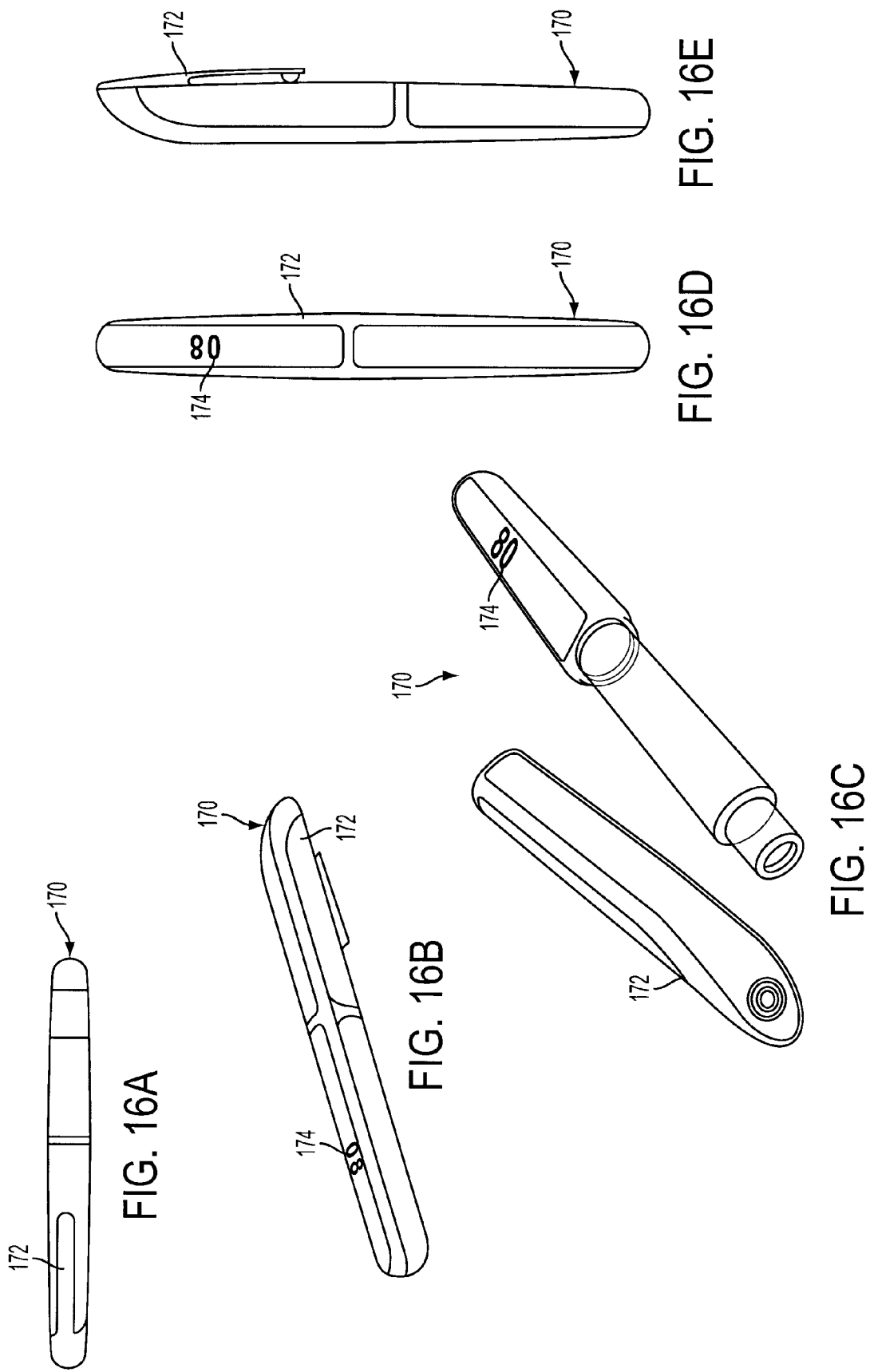

| OFFER | SERVICES | DESCRIPTION | EXAMPLES OF VALUE PROPOSITION |
|---|---|---|---|
| 1 | "EFFORTLESS DATA CAPTURE AND SEND" | MECHANISM TO CAPTURE AND TRANSMIT KEY BGM/ID/GSP/TBD DATA ELEMENTS TO A REPOSITORY | JOHNNY TESTS AT WORK & HOME USING 2 METERS AND 2 PENS, BUT ALL THE DATA IS SEAMLESSLY SYNCHRONIZED TO A REPOSITORY |
| 2 | "INFORMATION FROM DATA" | SYNTHESIZED INFORMATION FROM CAPTURED DATA ELEMENTS | "TEACHABLE MOMENT" JOHNNY GETS A TEXT MESSAGE FROM HIS CAREGIVER THAT HIS BG IS RAPIDLY DECLINING—MESSAGE SAYS "WHAT TO EAT" |
| 3 | INTEGRATED SERVICES FOR CONSUMERS | ADVANCED PATIENT-SPECIFIC INFORMATION ALERTS AND INTEGRATED PHARMACY SERVICES | JOHNNY SCHEDULES HIS NEXT LAB VISIT USING HIS RADIO METER |
| 4 | INTEGRATED SERVICES FOR BUSINESS | INFORMATION AIMED AT IMPROVING BUSINESS OPERATIONAL EFFICIENCY AS WELL AS IMPROVING PATIENT POPULATION HEALTH | THE MEDICARE COMP BIDDING REQUIREMENT FOR "FACE-TO-FACE START" IS WAIVED OR MADE MORE EFFICIENT (NEED = INSURE PATIENT USING PRODUCT SAFELY AND EFFECTIVELY) |

FIG. 30

| OFFER | SERVICES | DESCRIPTION | EXAMPLES OF VALUE PROPOSITION |
|---|---|---|---|
| 1 | "EFFORTLESS DATA CAPTURE AND SEND" | MECHANISM TO CAPTURE AND TRANSMIT KEY BGM/ID/GSP/TBD DATA ELEMENTS TO A REPOSITORY | JOHN MEASURES HIS GLUCOSE AND INJECTS AS USUAL, BUT THE DATA GOES TO A REPOSITORY WHERE OTHERS CAN SEE IT, WITHOUT ANY EFFORT BY JOHN |
| 2 | "INFORMATION FROM DATA" | SYNTHESIZED INFORMATION FROM CAPTURED DATA ELEMENTS | A DNE IN A DM CALL CENTER, TRACKING 300 PATIENTS, ACCESSES A PORTAL AND NOTES THAT 3 OF HER PATIENTS NEED IMMEDIATE ATTENTION |
| 3 | INTEGRATED SERVICES FOR CONSUMERS | ADVANCED PATIENT-SPECIFIC INFORMATION, ALERTS AND INTEGRATED PHARMACY SERVICES | JOHN GETS A PACKAGE OF STRIPS AND PEN NEEDLES TWO DAYS BEFORE HE RUNS OUT |
| 4 | INTEGRATED SERVICES FOR BUSINESS | INFORMATION AIMED AT IMPROVING BUSINESS OPERATIONAL EFFICIENCY AS WELL AS IMPROVING PATIENT POPULATION HEALTH | THE DM COMPANY (OR MEDICARE UNDER COMPETITIVE BIDDING) IN ONLY CHARGED FOR TEST RESULTS TRANSMITTED, NOT STRIPS |

FIG. 31

Diabetes Manager

File  Tools  Options  About

A Diabetes Patient Population Management Portal

2:45 pm
16 Sept 2005

[Search ▽]

| Patient Name | Blood Glucose Information | | Today's Insulin Dose Compliance ▽ |
|---|---|---|---|
| | Most Recent Reading ▽ | 7-day Average ▽ | |
| ☐ Hernandez, Jose | Low ⇨ | Low ⇦ | Non |
| ☐ Slutskaya, Yuri | Low ⇦ | Low ⇨ | Non |
| ☐ Yamaguchi, Kyoko | Low ⇦ | Low ⇦ | Full |
| ☑ Rogers, Erik | Low ⇨ | | Full |
| ☐ Smith, Karen | Low | In target range | Non |
| ☑ Grenoble, Alex | Low ⇦ | In target range | Full |
| ☑ Linden, Keith | | Low ⇦ | Non |
| ☑ Martinez, Jorge | | | |
| ☐ Wellington, Grant | | | Full |
| ☑ Adamson, Adrianna | | | Full |
| ☑ Gardner, Derek | | | Full |
| ☑ Schroeder, Berthold | | | Full |
| ☑ Taylor, Samantha | | In target range | Non |
| ☑ Antonucci, Heather | | In target range | |
| ☐ Weiss, Sandy | In target range | Low ⇨ | Non |
| ☑ Proctor, Josh | In target range | Low ⇦ | Non |
| ☐ Zimmer, Carly | In target range | High | Non |
| ☐ Dawson, LaShawanna | In target range | In target range | Non |
| ☑ McGowin, Cade | In target range | In target range | |
| ☑ Grobowski, Peter | In target range | In target range | |
| ☐ Johnstone, Emily | In target range | In target range | |
| ☐ Spano, Bella | In target range | In target range | |
| ☐ Wang, Valerie | In target range | In target range | |
| ☑ Chen, Bruce | | | Full |

FIG. 42

Diabetes Manager

A Diabetes Patient Population Management Portal

2:45 pm
16 Sept 2005

Patient Information

| | |
|---|---|
| Name: | Emily Johnstone |
| Age: | 27 |
| Date of Birth: | 13 February 1978 |
| Height: | 5' 3" |
| Weight: | 106 lbs. |
| Diabetes Type: | Type 1 |
| Initial Diagnosis: | 12 August 1984 |
| Last office visit: | 27 Aug 2005 |
| A1C Results: | 8.4% |
| Insulin Delivery: | Injection |
| Medical Allergies: | Penicillin |

Notes:

Blood glucose (mg/dL) — March 2006 — Days

| | |
|---|---|
| Average # of tests/day: | 3.7 |
| Average insulin doses/day: | 10 Units |
| Most Recent BG Reading: | 120 mg/dL  16 Sept 2005 13:40 |
| 7-day BG Average: | 105 mg/dL |
| Today's Insulin Dose: | Lantus: 10 Units 8:00  Humalog: 5 Units 12:00 |

FIG. 43

SYSTEM AND METHODS FOR IMPROVED DIABETES DATA MANAGEMENT AND USE EMPLOYING WIRELESS CONNECTIVITY BETWEEN PATIENTS AND HEALTHCARE PROVIDERS AND REPOSITORY OF DIABETES MANAGEMENT INFORMATION

This application is a divisional application of U.S. patent application Ser. No. 12/293,120, filed Sep. 16, 2008 and having a 35 U.S.C. §371(c) date of Feb. 23, 2009, which claims the benefit under 35 U.S.C. §119(e) of U.S. provisional patent application Ser. No. 60/784,760, filed Mar. 23, 2006; the contents of each being incorporated herein by reference.

BACKGROUND OF THE INVENTION

Field of the Invention

The present invention generally relates to improved methods, devices and system for disease management. More particularly, the present invention relates to real-time communication of data between devices (e.g., blood glucose meters, insulin delivery devices) and a repository and analysis of repository data to obtain information to improve disease management and provide cost savings to disease management stakeholders.

Description of the Related Art

FIG. 1 illustrates an existing system 10 for diabetes management. For convenience, the following abbreviations shall be used herein:
BGM blood glucose meter
DM diabetes management
DMC disease management companies
DMD diabetes management data
WM wireless BGM As shown in FIG. 1, a patient 12 performs blood glucose monitoring (e.g., using lancets and a BGM 18 with test strips, or a continuous meter) and administers insulin injections (e.g., via a syringe, pen or pump 20) as needed. The BGM and the insulin injections are typically recorded manually in a notebook 22 by the patient or his or her caregiver to share with a healthcare provider such as a doctor 14 or a disease management company 16. This information is typically shared via telephone (e.g., telephone 26, 28 and 32), computer (e.g., computers 24 and 30), or in person during office visits. This information can also include information relating to diet, exercise and other factors that influence diabetes management outcomes. Unfortunately, this information is not verified and often not recorded, collected or managed in a reliable and cohesive manner to be useful to the patient's healthcare team in facilitating optimal diabetes management.

With continued reference to FIG. 1, diabetes management data such as blood glucose tests and insulin intake can be recorded using a personal computer (PC) 24, as opposed to handwritten recordkeeping 22, or uploaded to a patient's PC 24 from a device (e.g., a blood glucose meter 18 or insulin delivery pen 20) using a software interface. Conventional communications interfaces, however, are inconvenient because a patient 12 must acquire a communication interface such as a specialized modem and/or install software on a PC 24 to upload data from a BGM 18. Further, such PC interfaces for diabetes data management do not necessarily allow the entered data to be shared with other stakeholders in diabetes management and care, that is, physicians and other healthcare providers 14, insurers, or disease management companies (DMCs) 16 that are typically hired by employers or insurance companies, as indicated by the optional lines shown in phantom in FIG. 1. If diabetes management data from a patient 14 can be provided to a healthcare team member's PC 30, that information is generally not recorded in a comprehensive manner that assures completeness, accuracy and timeliness of the data. For example, quite often patients 14 fail to test, or to write down, enter or upload a blood glucose test result or insulin injection, leaving healthcare team members 30 and 16 with incomplete information and not allowing them to identify teachable moments or events in diabetes management or respond in real-time.

Similarly, special cradles such as GlucoMON by Diabetech in Dallas, Tex., are currently available to get data from a patient 14 securely to other people. Diabetech makes the device and manages the service to transmit blood glucose test results to selected people, typically via cell phone, pager, or e-mail, according to the instructions of the patient 14 or their legal guardian. This data, however, is merely reported to selected persons and not collected and managed in a comprehensive manner. Additionally, this system requires that the user 14 acquire and connect a secondary device to their BGM 18. Thus, a need exists for an integrated device for monitoring glucose levels and reporting same to other stakeholders in diabetes management and care.

Cell phones combined with diabetes data management functions have been proposed, not surprisingly in an era of increasingly indispensable personal electronic devices. For those with chronic conditions such as diabetes, technical convergence of healthcare and personal electronic technology makes even more sense to facilitate use of medications, meters, pumps, injections, and the need to carefully track and document important health data, particularly for those with chronic conditions that require significant self-management.

Several medical companies are developing smarter, more convenient monitoring equipment and are using telecommunications technology to create multipurpose, portable devices for patient use. One of these companies is HealthPia America, a Newark, N.J.-based telemedicine venture that has developed a cell phone that also serves as a blood glucose monitor and features a pedometer. An embedded electronic biosensor in the battery pack enables the cell phone to have a glucose meter function. The sensor reads blood glucose levels from a strip. The data is then uploaded to the cell phone's display. The phone can be programmed to send the information instantly to a health care provider 14, parent, or guardian. Movement and exercise also can be monitored with the built-in pedometer. The phone can be programmed to send an alert to the caregiver or clinician via short-message service if there is no pedometer reading for a pre-programmed length of time. The care manager can call back to check if the patient 12 is okay, and if there is no response, prearranged emergency procedures can be initiated. This feature could be especially useful for detecting insulin reactions or severe hypoglycemia in diabetes patients 12. The biggest advantage of the Diabetes Phone is its alarm features, which allow a physician to set specific parameters. If the phone reports continuously high blood glucose, for example, a doctor can react in real-time.

Other diabetes cell-phone projects include research at Oxford University in the U.K. to test a system similar to that of HealthPia America. In another venture, British patients 12 with diabetes have been able to register since 2002 with Sweet Talk, a message service that reminds them via cell phone to take their insulin and offers general education about living with diabetes. Further, in 2003, IBM announced that its "Bluetooth" short-range wireless technology could be used to intercept a person's 12 heart rate and send it to a cell phone.

At the ITU Telecom Asia 2004 show in Korea, LG Electronics showed a novel handset, the KP8400. The KP8400 is designed for diabetics and is capable of doing blood sugar level tests just as would a dedicated device. Users 12 place a strip of testing paper into the sensor located in the phone's battery pack, place a drop of blood on the end of the strip, and then get a reading from the phone. The reading can then be uploaded to an online database for later retrieval. LG Electronics has a strategic alliance with Healthpia Co., Ltd. to implement the KP8400.

Whether these new and proposed electronic devices for diabetes management will result in their widespread adoption and better self-care for patients 12, or simply more work for clinicians 14 as they strive to manage a new stream of information, is the central question as this new frontier of electronic medicine is explored. For example, the data reported by one of these emerging cell phone technologies does not appear to be managed in a cohesive manner such that the real-time test results can be associated with other information such as test trip lot number and use verification, or mealtime events and therapy intervention (e.g., insulin injection), and the like.

Further, what is largely overlooked is the value to less traditional stakeholders in the business of DM. A need therefore exists for business models, methods and apparatuses that maximize the value of collected DMD for various stakeholders such as disease management companies 16, insurers and healthcare networks.

As stated above, disease management companies 16 are typically hired by a patient's insurer or employer to provide the patient 12 with educational support for their disease. DMCs obtain claims data such as prescriptions and visits to healthcare providers 14, as well as other data such as BG measurements, insulin dosages, diet and exercise. Much of this information is collected from the patient 12 via telephone (e.g., telephones 26, 28 and 32) which is problematic for a number of reasons. For whatever reasons, patients are often not completely truthful with their healthcare providers 14 and DMC 16 representative about their DM lifestyle choices (e.g., diet, exercise, BG testing and medicating with insulin). Some of the reasons are inadequate education about diabetes self-management, apathy, embarrassment, economic barriers, lack of proficiency in testing and use of data interface equipment, or faulty equipment or testing technique (e.g., poor timing with respect to meal times).

A need therefore exists for a diabetes data management system that allows DMCs 16 and other third parties (e.g., insurance companies, Medicare, Medicaid, HMOs, etc.) to provide patients 12 with incentives to take better care of themselves and manage their diabetes and otherwise improve their outcomes. For example, a need exists for a system that can monitor and have verification of a patient's actual blood glucose monitoring practices. A DMC 16 can then, for example, remove economic barriers by giving patients, who have shown progress in managing their diabetes, test strips and/or a blood glucose monitor at nominal cost or no charge or by waiving their co-pays.

Currently, reimbursement for diabetes testing supplies by third parties (e.g., insurance companies, Medicare, Medicaid, HMOs, etc.) is based on a model where a specific number of BGM test strips are covered depending on the patient's condition (e.g., a person 12 with diabetes who requires insulin injections to help manage their diabetes may have coverage for 60 BGM test strips per month (2 per day); or a person 12 with diabetes who uses an oral medication to help manage their diabetes may have coverage for 30 BGM test strips per month (1 per day).) In this model, the refill of a BGM test strip prescription is the only indication of use of the BGM test strips. However, this does not provide any objective evidence: a) that the patient 12 actually tested their blood glucose using the BGM test strips; b) that the tests were done at appropriate times; c) of the results of any tests that were done. In some situations, patients 12 may "stockpile" their test strips or provide them to other family members or friends who do not have equivalent insurance coverage for their needs. In these cases, the third party payor is making payments for testing supplies that are not being used or not being used appropriately. In this model, for example, the mail order supplies company and, ultimately, the BGM test strip manufacturer benefit because they are paid by the third parties for all test strips that are delivered to the patient regardless of the patient's actual use. A need therefore exists for a "pay for results" model wherein a payor pays for only those strips that are actually used.

SUMMARY OF THE INVENTION

Aspects of the exemplary embodiments of the present invention address at least the above problems and/or disadvantages and provide at least the advantages described herein.

For example, an exemplary embodiment of a DM system is provided that simplifies patient involvement with DMD reporting by automating sharing of collected data among other stakeholders. Preferably, there is no patient involvement in the automated data movement (e.g., not even the need to press a "Send" button to upload BG measurement data to a stakeholder, or the more user-intensive option of connecting their BGM device to a computer or other communications device).

An exemplary embodiment of a DM is provided that improves patient compliance for record-keeping and sharing information with healthcare providers. For example, data collected accurately reflects status of patient and obviates failure to test for or reporting of events of interest to stakeholders, use of bad test strips, etc.

Exemplary embodiments of DM system business models are provided that emphasize payors' use of data and not only patients' use of data, and emphasizes the value of the DMD versus the devices used to collect the data.

Real-time reporting of event data relative to a stakeholder is provided in accordance with exemplary embodiments of the present invention. A transaction is tailored to use (e.g., 100% real-time upload but less than real-time for retrieval and access, depending on which stakeholder is involved).

Exemplary embodiments of BGM devices are simplified to be display devices and whose analytical capabilities for generating averages and trend data are moved to a repository level. The devices therefore become less complex, which provides a number of benefits (e.g., reduced development time and therefore time to market; and reduced complexity and thereby reduced potential for safety hazards). Simplified BGM devices also increases useable life of the device because software "upgrades" are performed at the repository level, and not at the device level. These simplified devices do not have to be replaced as often due to upgrades because device firmware upgrades can be performed wirelessly. For example, instead of upgrading a memory module, the device can be provided with FLASH memory to receive upgrades from a repository over a communication network.

The exemplary embodiments of the present invention replace the current state of reimbursement for test supplies model with a "pay-for-result" model of doing business and realizes many advantages.

The exemplary embodiments of the present invention provide several business models, methods and apparatuses for maximizing the value of collected DMD for various stakeholders such as disease management companies, insurers and healthcare networks.

In accordance with an exemplary embodiment of the present invention, an insulin delivery system is provided comprising: an insulin delivery device comprising at least one of a syringe, a microneedle, a pump and an insulin pen configured to deliver insulin, an RFID tag connected to the insulin delivery device for transmitting an insulin delivery device identification number corresponding to the insulin delivery device and for storing insulin delivery device data comprising insulin-type delivered via the insulin delivery device, and a blood glucose meter comprising an RFID reader for activating the RFID tag to collect at least the insulin delivery device data, and a wireless communication circuit configured for wireless communication with a repository for transmitting data relating to insulin delivered by the insulin delivery device to the repository automatically and substantially in real-time without user involvement.

In accordance with another exemplary embodiment of the present invention, a method of monitoring test strip usage comprises: storing testing data for patients in a repository, the testing data comprising for respective patients at least one of the number of recommended tests per day and the number of test strips allotted to the patient via one of a supplier and an insurer, automatically transmitting test results from a blood glucose meter to the repository without user involvement, the test results comprising measured glucose level, and comparing the testing data and the test results stored in the repository for at least a selected one of the patients to determine at least one of the number of test strips actually used by the patient and the number of allotted test strips that are unused within a selected time period.

In accordance with an exemplary embodiment of the present invention, a method of using diagnostic data comprises: receiving therapy data and corresponding time stamps for when different therapy events were administered to a patient, receiving diagnostic test data and corresponding time stamps for when diagnostic tests were administered to the patient, receiving parameters comprising respective time stamps for at least two of when the patient eats meals, sleeps and night-time tests are administered to the patient, and analyzing the therapy data time stamps, the diagnostic test data time stamps and the respective time stamps for at least two of when the patient eats meals, sleeps and night-time tests are administered to the patient to associate a therapy event with a test administered to a patient and at least one of a meal-time, bedtime, and night-time test. Alternatively, the method can comprise receiving a parameter corresponding to a typical number of meals eaten per day, and then analyzing the therapy data time stamps, the diagnostic test data time stamps and the number of meals eaten per day to determine how the therapy data time stamps and the diagnostic test data time stamps cluster relative to the number of meals eaten per day for segmenting a day into mealtimes and categorizing the therapy data time stamps with respect to mealtimes.

BRIEF DESCRIPTION OF THE DRAWINGS

The above and other objects, features, and advantages of certain exemplary embodiments of the present invention will be more apparent from the following detailed description, taken in conjunction with the accompanying drawings in which:

FIGS. 5A and 5B are perspective views of a wireless meter constructed in accordance with an exemplary embodiment of the present invention;

FIGS. 10A and 10B are block diagrams of a wireless meter employing a built-in or cell modem attachment for connectivity in accordance with an exemplary embodiment of the present invention;

FIGS. 13A, 13B and 13C are perspective side and back views of a BGM in a cell phone in accordance with an exemplary embodiment of the present invention;

FIGS. 16A, 16B, 16C, 16D and 16E illustrate a connected pen in accordance with an exemplary embodiment of the present invention;

FIGS. 29, 30 and 31 illustrate the benefits of the connectivity and value added information provided by exemplary embodiments of the present invention in the context of overall patient and disease management;

FIGS. 42 and 43 illustrate display screens generated for viewing via a disease management stakeholder computing device in accordance with exemplary embodiments of the present invention.

Throughout the drawings, the same drawing reference numerals will be understood to refer to the same elements, features, and structures.

DETAILED DESCRIPTION OF EXEMPLARY EMBODIMENTS

The matters defined in the description such as a detailed construction and elements are provided to assist in a comprehensive understanding of the embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

With regard to the present invention, the term "data" generally refers to numerical values such as blood glucose levels, times of day, dosage amounts, and so on. The term "information" generally refers to educational information, feedback, qualitative status of patient, analysis of data, and so on. DMCs generally have proprietary algorithms for synthesizing information and data received from patients; however, this information and data is often faulty due to inadvertent or intentional misinformation from the patient, poor record keeping, failure to contact patient, and so on.

The present invention provides an improved DM system whereby sharing of patient DM-related data with other stakeholders is fully automated and real-time. Further, improved access to more reliable patient DM data by the other stakeholders allows for improved use of the information to facilitate better management of the disease.

Figure 2:
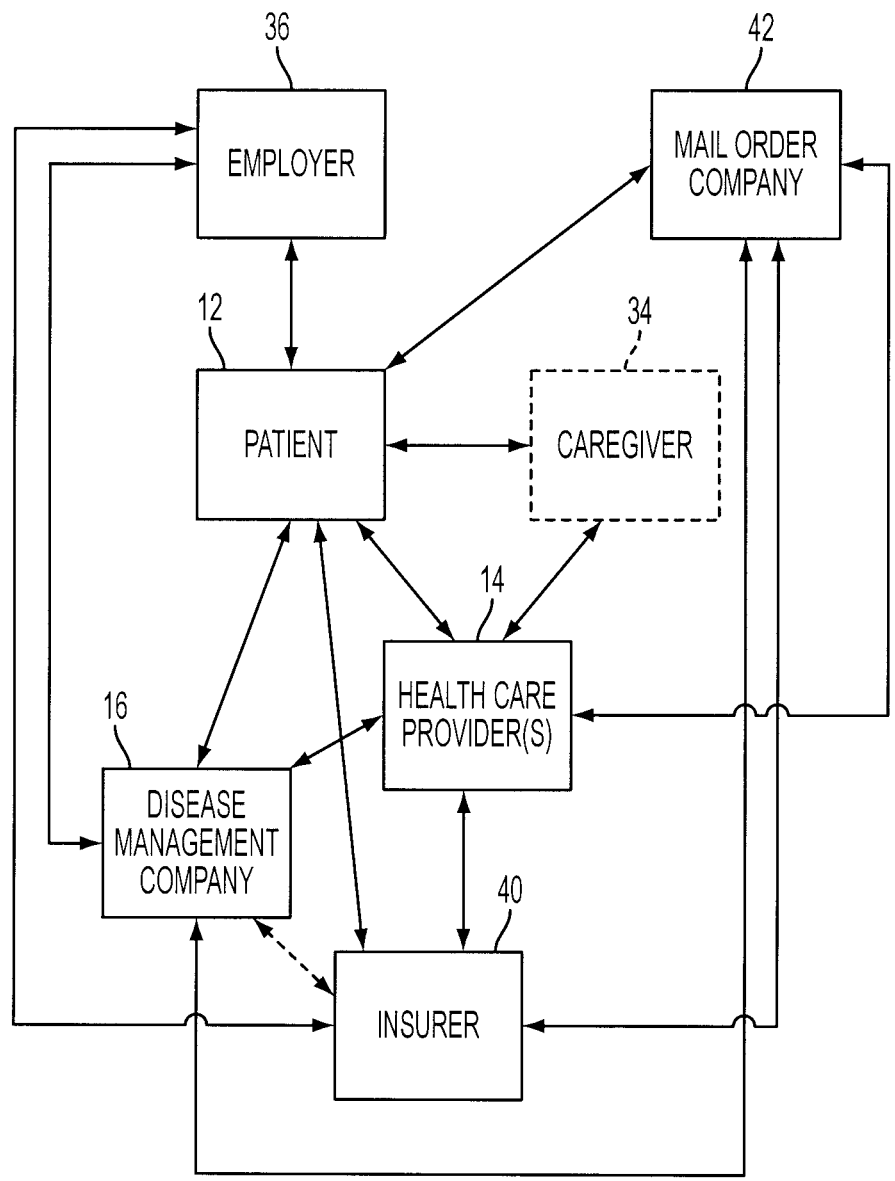
FIG. 2 shows stakeholders in disease management and the typical flow of information.

FIG. 2 illustrates the stakeholders in diabetes management. The stakeholders are the patients and optionally their caregivers, their healthcare team members (e.g., physician), their insurers, their employers. As described above, a DMC 16 can be hired by a patient's insurer or employer to provide the patient 12 with educational support for his or her disease. DMCs 16 obtain medical claims data such as prescriptions and visits to healthcare providers, pharmacy data and laboratory data, and then other data such as BG measurements, insulin dosages, A1c levels, diet and exercise. Currently, much of this information is collected from the patient via telephone which is problematic (i.e., expensive, inconvenient and inaccurate). Other stakeholders in DM can be mail order companies providing DM supplies such as test strips to patients and caregivers. As described below, mail order companies currently exist that mail a maximum number of test strips allowed to patients each month by Medicare or other third party payors. This practice of mailing strips leads to unfair billing since many of these strips are unused or used ineffectively. The present invention provides benefits to each of these stakeholders and particularly to disease management companies, healthcare networks and providers, insurers and Centers for Medicare and Medicaid Services (CMSs), whose needs are often not emphasized as technological advances in diabetes management are developed.

Figure 1:
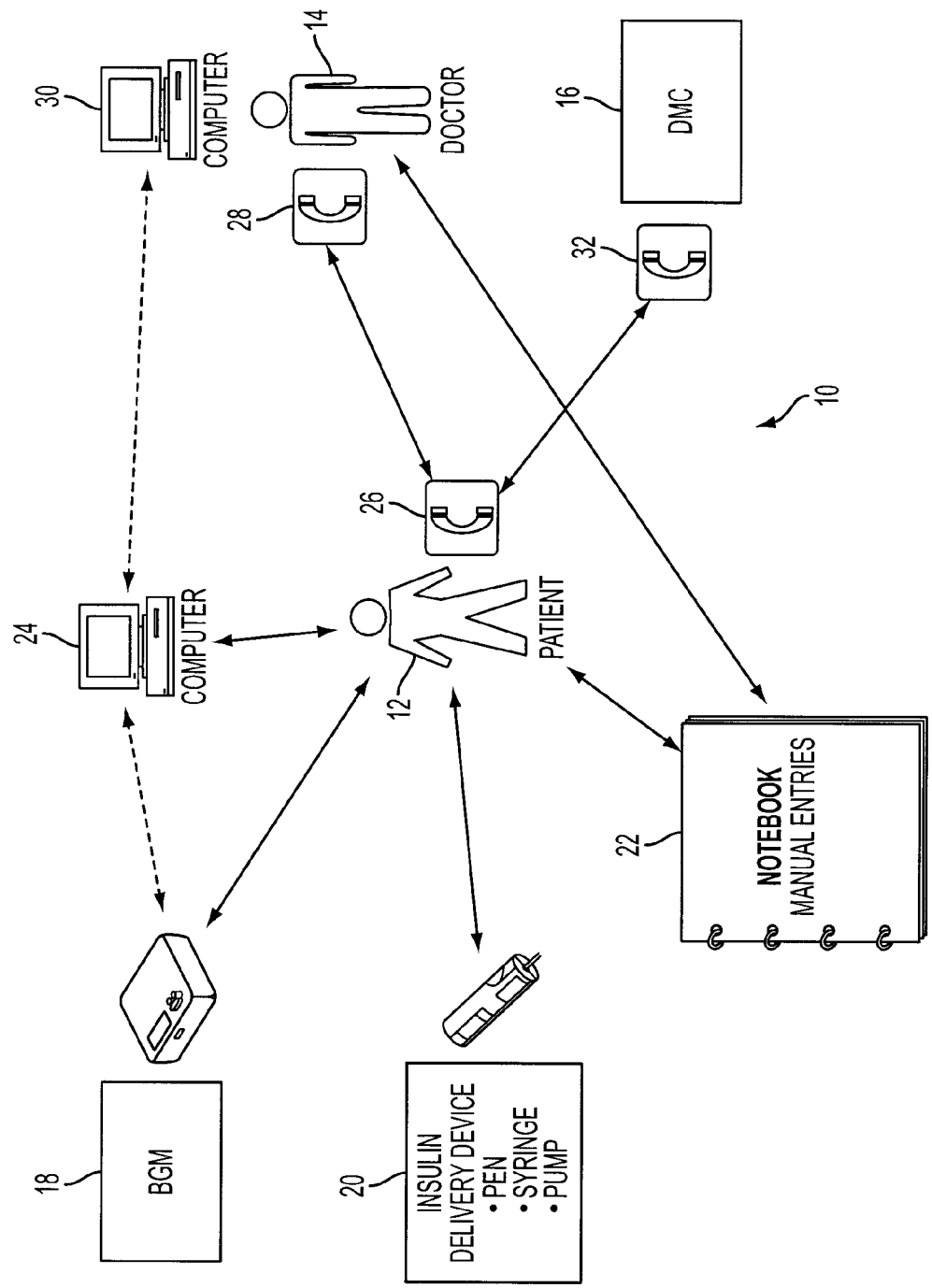
FIG. 1 shows current flow of data and information between patients and their disease management devices and stakeholders.
Figure 3:
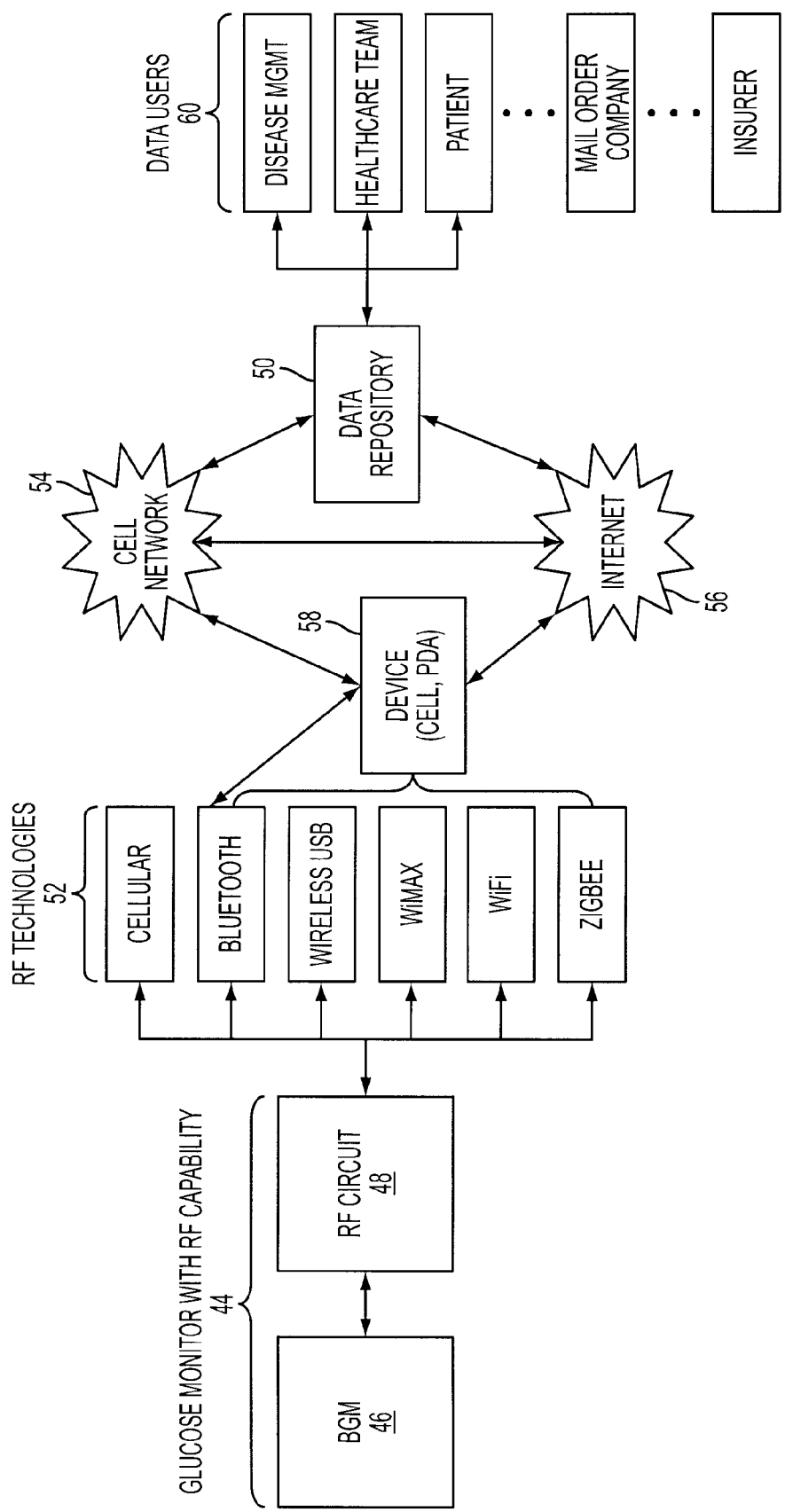
FIG. 3 shows wireless connectivity and RF communication pathway options to improve flow of data and information between patients and their disease management devices and stakeholders and a repository in accordance with an exemplary embodiment of the present invention.

FIG. 1 illustrates some of the devices (e.g., BGM 18 and insulin delivery device 20) that can be used by a patient 12 or his or her caregiver 34 to collect DM-related data and information. FIG. 3 illustrates additional patient devices and some of the stakeholder devices that can be used to connect to a repository 50 for diabetes data and information and communicate with patient devices in accordance with an exemplary embodiment of the present invention. The patient devices can include, but are not limited to, BGMs, insulin delivery devices, position tracking devices, nutrition and other data or information input devices. BGMs can be, but are not limited to, non-continuous BGMs (i.e., BGMs that require a patient to draw blood for use as a sample on a test strip that is then inserted into and read by a meter), or continuous monitors (i.e., monitors using a catheter inserted under the skin to take fluid measurements for BG level). Insulin delivery devices can be syringes, insulin pens, insulin jet injectors, external insulin pumps, and implantable insulin pumps. Position tracking devices can be, but are not limited to, pedometers and GPS tracking devices. Other devices for automating DM-related data delivery from the patient 12 to other stakeholders can be smart bottles for test strips, and wireless syringes, as described in more detail below. Other examples of patient information can be recording of activities such as diet, exercise and lifestyle (when meals are taken, exercise occurs, etc). A WiMax docking station or cell phone can have a display and be programmed to generate a dialog screen to request input of food intake after a noon-time reading. A GPS tracking device can indicate when patient is at home or the gym and generate a screen to enter exercise information. Similarly, a pedometer can monitor general exercise level via recorded movement.

Figure 4:
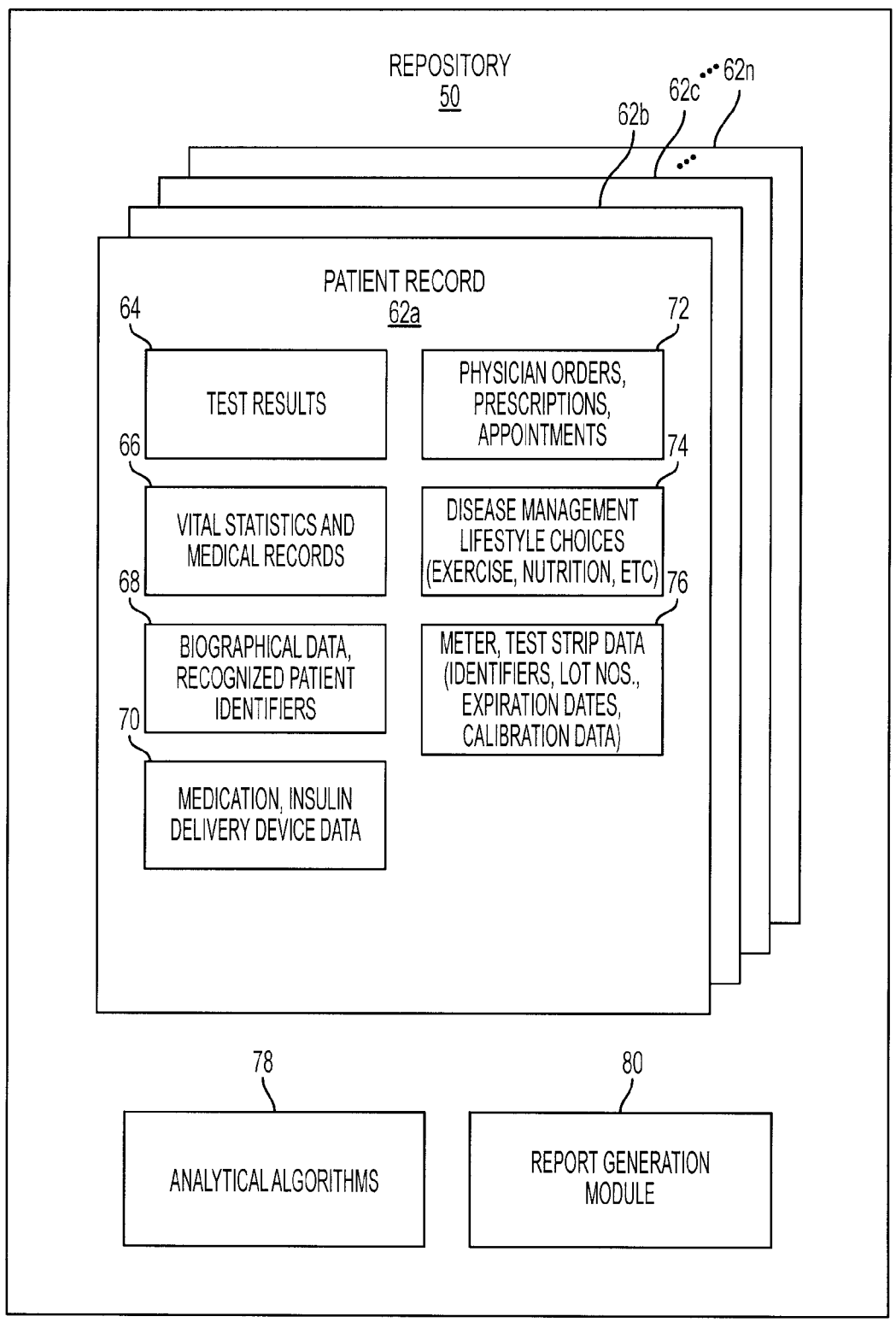
FIG. 4 is a block diagram of a repository in accordance with an exemplary embodiment of the present invention.

FIG. 4 illustrates a repository 50 in accordance with an exemplary embodiment of the present invention, and types of data and information stored therein. For example, the repository 50 can store data 64 and 70 from BGMs and insulin delivery devices, lifestyle information 74 such as meal-times and food intake, exercise, patient location, medical data such as cholesterol, blood pressure, information 76 pertaining to number of and lot number of test strips allotted to patient, testing frequency and BG level goals and variances, meter/strip calibration data, and so on. The repository 50 also stores for each patient biographical data 60, including one or more recognized patient identifiers as described below, medical data and vital statistics 66, physicians orders. Appointment and prescriptions 72, among other information. The repository 50 can also contain analytical algorithms 78 for analyzing data stored therein and a report generation module 80.

With continued reference to FIG. 3, a wireless blood glucose meter (BGM) 44 comprising a BGM 46 radio frequency (RF) communications circuit 48 can communicate with various data users 60 (e.g., the patient wireless communication devices such as PDA or laptop or PC, physician and other members of the patient's healthcare team and the disease management company hired to work with patient) via various RF communications pathways 52 in accordance with an exemplary embodiment of the present invention. FIGS. 5-17 illustrate different types of wireless BGMs or devices 44 containing BGMs and their respective communications pathways to the different data and information users. These devices can communicate with the data and information users and repository 50 via a cellular network 54 and/or the internet directly 56 via one or more devices 58 such as a cellular phone, personal data assistant (PDA), docking station, personal computer CPs or other computing device with communications capability. The RF technologies illustrated in these figures include, but are not limited to, cellular, Bluetooth, Wireless USB, WiMax, WiFi and ZigBee.

With reference to FIGS. 5A and 5B, an exemplary wireless BGM 44 is shown as constructed in accordance with an illustrative embodiment of the present invention. The wireless BGM 44 includes a display 84 to show blood glucose level, date and 86 time the level was measured, along other information. The wireless BGM has an antenna 86, a test strip reader input 88 and an on/off button 90. FIG. 5B illustrates a port 92 for connecting the wireless meter to another device such as a docking station, cellular modem, and so on.

Figure 6:
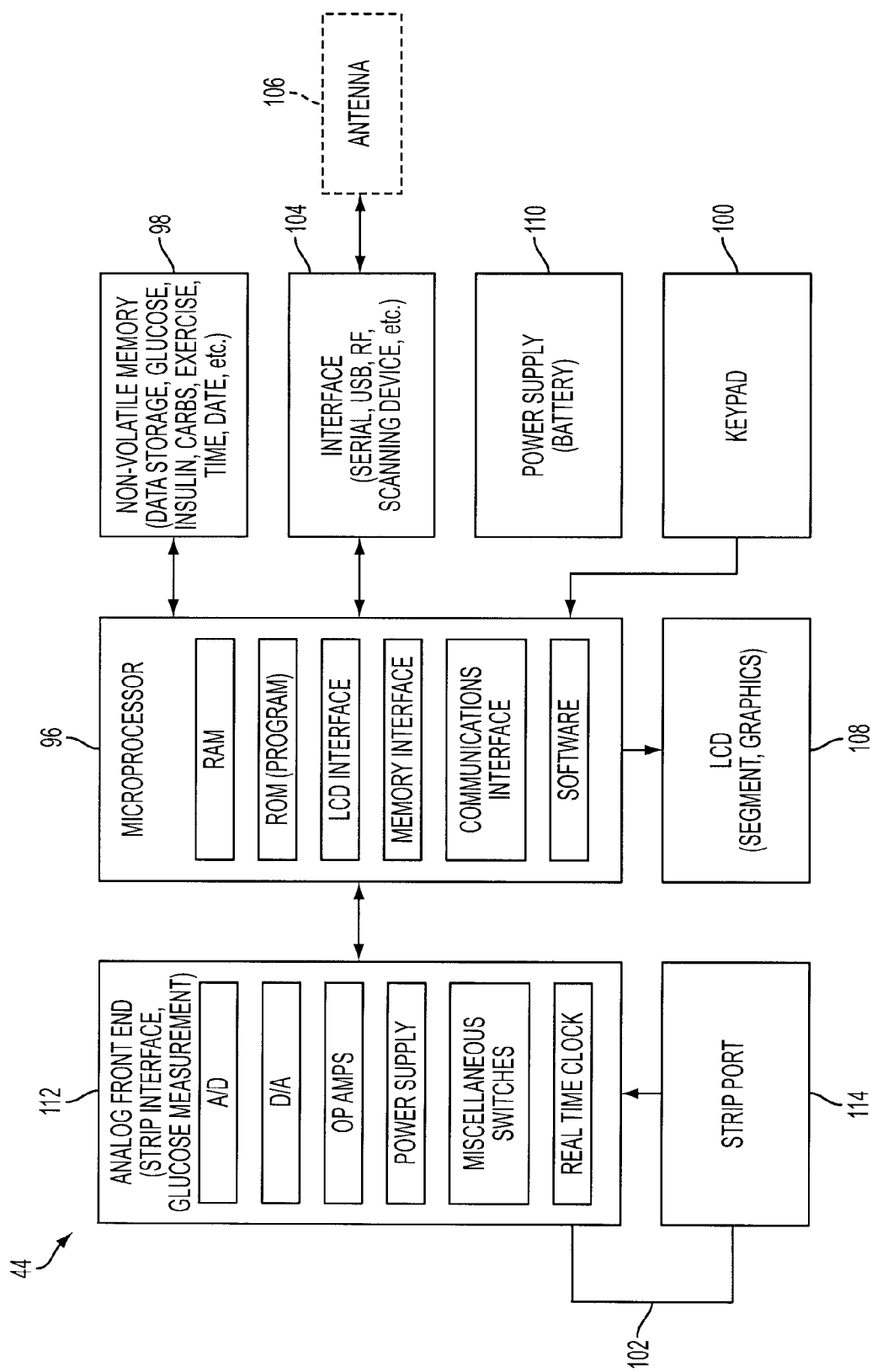
FIG. 6 is a block diagram of a wireless meter constructed in accordance with an exemplary embodiment of the present invention.

FIG. 6 illustrates components of an exemplary wireless BGM 44 as constructed in accordance with an illustrative embodiment of the present invention. The wireless BGM 44 comprises a processor 96, a memory device 98, a display 108 an input device (e.g., keypad 100), a test reader 102, a communications interface circuit 104, antenna 106 and power supply 110. The test reader can comprise an analog front end 112, that is, a test strip interface between a strip port 114 and a processor 96 for glucose measurement. As described below, a BGM can be provided that operates with a base station, as shown in FIG. 11A, and therefore does not need an antenna 106. A communications interface circuit 104 can be configured to allow the wireless BGM 44 to communicate with one or more wireless protocols illustrated in FIG. 4, among others. If the communications interface circuit 104 enables the wireless BGM 44 to communicate via more than one wireless protocol, it can include a scanning device to scan the wireless frequencies available and to select, based on optimal transmission qualities, the best communications protocol to use to transfer data such as the most recent blood glucose reading to the repository.

In accordance with a preferred embodiment of the present invention, the wireless BGM 44 requires no user involvement to transmit blood glucose readings following a test to the repository 50. For example, the wireless blood glucose meter 44 can be programmed and configured to be an event-driven device that automatically sends recently acquired test data from the reader based on detection of insertion of the strip into the reader, telephone activation if the wireless BGM is built into or connected to a cellular telephone, pressure activation or selected motion activation of the wireless BGM. An embedded acknowledgement function is preferably implemented to ensure that the repository 50 received the results completely (i.e., any errors in the transmitted data can be sufficiently corrected or the data is retransmitted).

The wireless connectivity of the blood glucose meter 44 to the repository 50 and the automated transfer of blood glucose test results via the wireless RF communications pathway facilitate increased compliance of the patient with diabetes management guidelines. This is because the test results are automatically provided to diabetes management stakeholders. Further, the repository data is more comprehensive since the automated delivery of the test results obviates situations where patients or the caregivers fail to test and/or fail to report the test results to the requisite stakeholders. Also, the communication of the data to a repository allows a level of abstraction and analysis of the data to provide other information (e.g., data on the number of tests performed could be used to facilitate test strip prescription tracking and replenishment; data on insulin delivery could be used to facilitate prescription tracking and replenishment of supplies.) In addition, as described above, other disease management information can be transferred to the repository 50 and therefore to the requisite stakeholders via the same radio frequency communications pathways such as GPS and pedometer readings, insulin delivery information and meal-time information. These devices can be connected to the blood glucose meter 46 and/or its RF circuit 48, or have a separate RF circuit, for communicating this additional information to the repository. Accordingly, unlike present blood glucose readers and communications interfaces such as patients' PCs, data such as blood glucose test results and insulin intake and other disease management information is given a wider view. In other words, the diabetes management data and other information are available to more stakeholders, and the stakeholders have access to more comprehensive information relating to the patient. By contrast, conventional devices generally only give selected test results to selected persons who have only a local view of the test result information and no control over compliance of the patient in testing or reporting the test results. Further, conventional blood glucose meters and other data devices generally use separate communications transactions to send these results to the various persons involved, and generally do not employ a repository for the test results or other information.

In addition, the present invention allows for transfer of information from patients 12 and other stakeholders (e.g., 14, 16, 40 and 42) to the repository and from the repository to patients and to other stakeholders is preferably or ideally in real-time (e.g., immediately following a blood glucose test or insulin injection). It is to be understood, however, that the transfer of data between the stakeholders and the repository 50 can be configured to occur within a selected time period following an event (e.g., patient test, or repository algorithmic determination that a patient should receive a selected message), or a selected number of times per day, and so on.

FIG. 4 is a block diagram of an exemplary repository 50 in accordance with an exemplary embodiment of the present invention. The repository preferably comprises many records $62_1, \ldots 62_n$, for respective patients 12 such as data transmitted from wireless meters and syringes or pens, data received via traditional means such being collected as the result of telephone calls between two or more of a physician, disease management representative, insurer, and the patient, information collected from GPS devices, pedometers and meal-time information. As will be described in greater detail below, an illustrative embodiment of the present invention allows for test strip use, lot numbers, calibration data and meter number to be maintained for each patient 12. The organization of the data and information and identification of same with respect to a particular patient 12 can be accomplished in a number of different ways. For example, data received from a communications chip configured for use with the repository 50 can be sent packetized with a header including a unique identification number assigned to a device 44 or 58 as well as a patient 12. Data and information relating to a particular patient 12 can be related to that patient via more than one identification means. For example, wireless meter 44 data can use a identification code which can be a randomly generated code, and test strip information can be related to the patient 12 and become a part of the patient's repository records based on a recognized patient ID assigned by Medicare, insurer or other payor, for example.

Returning to the wireless blood glucose meters of FIGS. 5, 7, 8, 9, 10A and 10B, these devices referred to generally as 44 illustrate different RF communication pathways between the wireless blood glucose meter and the repository 50.

Figure 7:
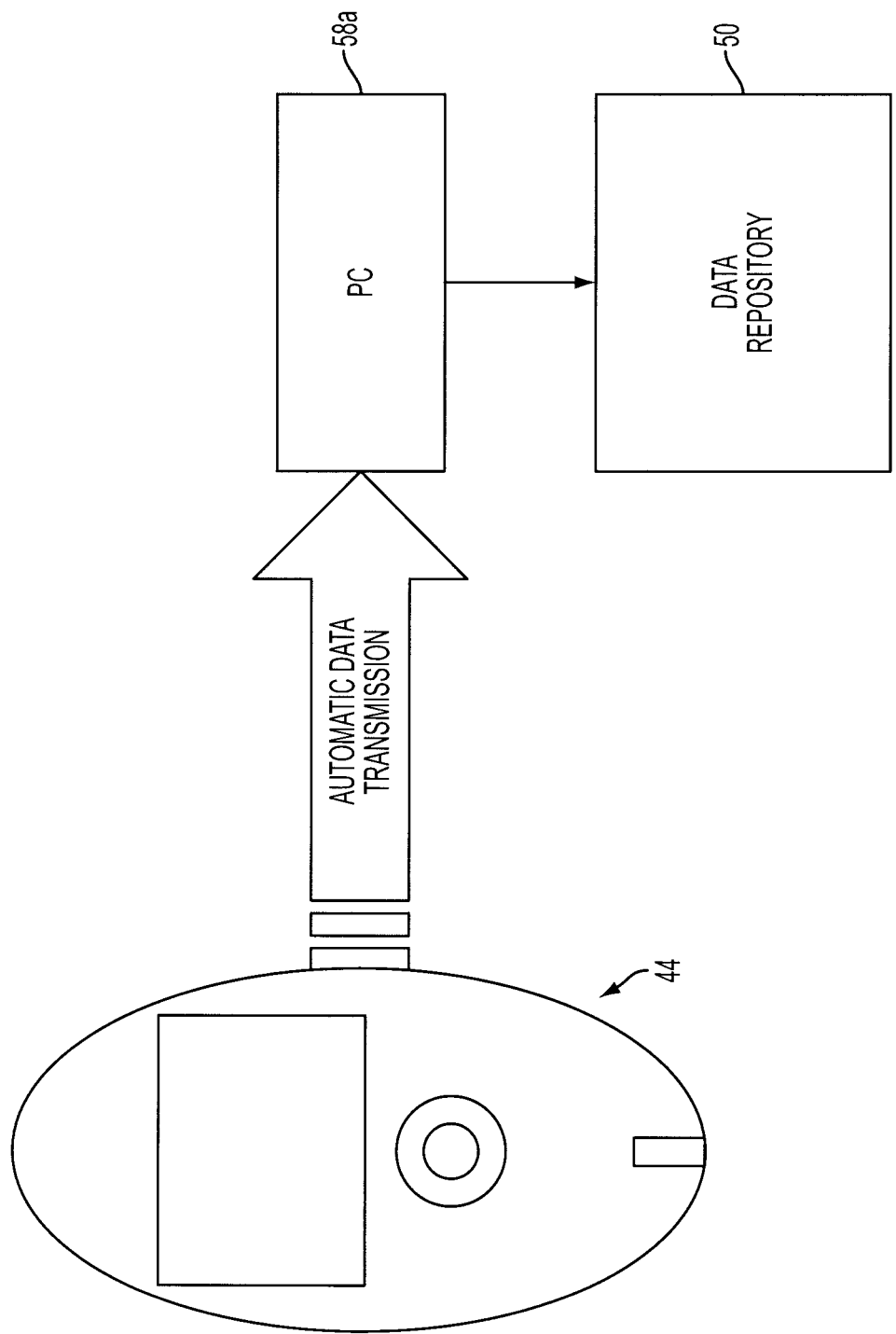
FIG. 7 is a block diagram of a wireless meter employing wireless USB connectivity in accordance with an exemplary embodiment of the present invention.

FIG. 7 illustrates a blood glucose meter 44 having a communications circuit configured to communicate with a device 58 such as a PC indicated generally as 58a via wireless USB technology. The PC 58a, in turn, can communicate with the repository 50 via the internet 56 or a cellular network 54. In other words, the PC 58a can be connected, for example, to the internet 56 via an analog or digital connection or connected to a cellular network 54 via a cellular modem card.

Figure 8:
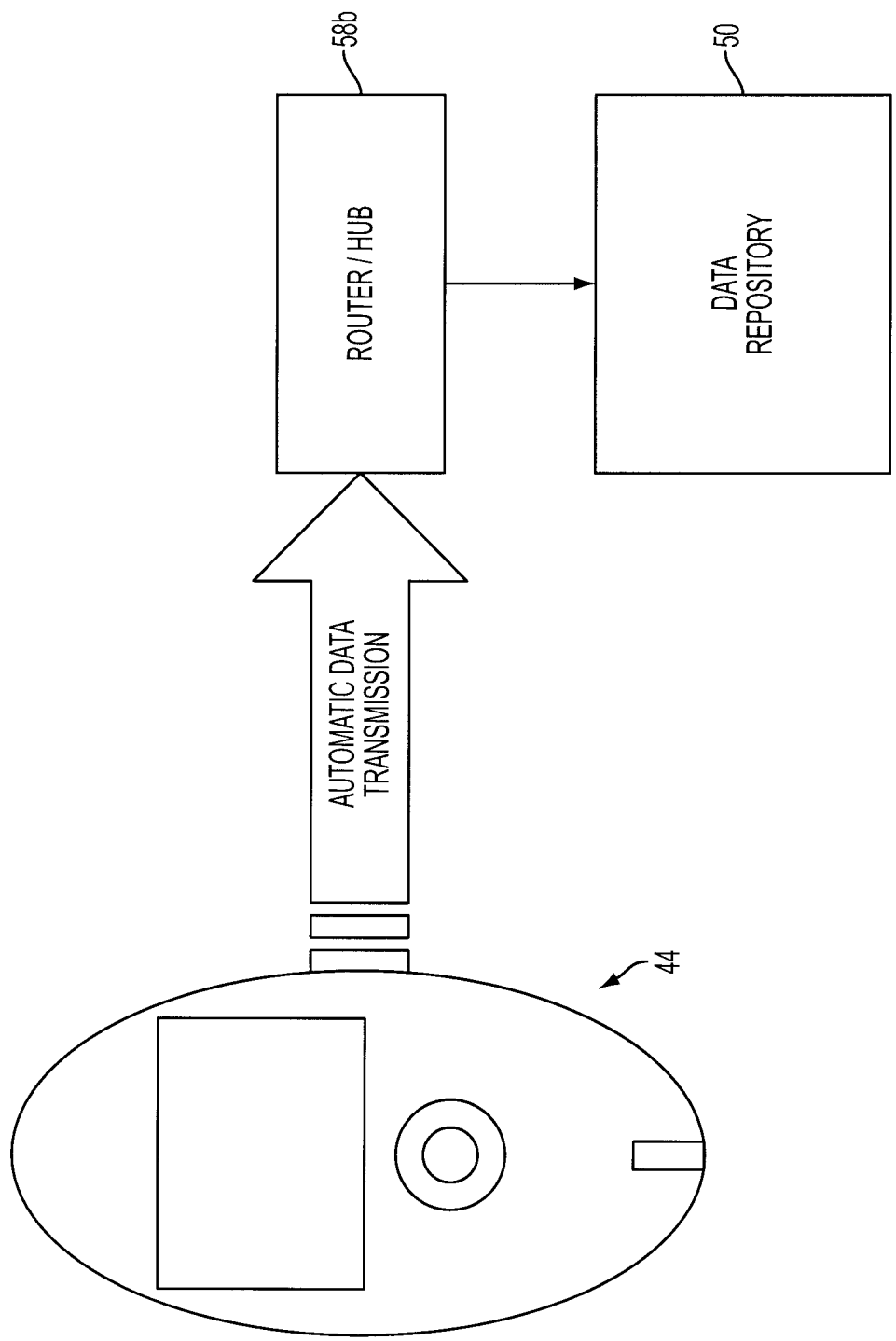
FIG. 8 is a block diagram of a wireless meter employing WiFi or WiMax connectivity in accordance with an exemplary embodiment of the present invention.

FIG. 8 illustrates a blood glucose meter 44 with the communications interface circuit 104 having a built-in WiFi or WiMax communications capability for automated data transmission to a router or hub for providing meter data to the repository via the internet.

Figure 9:
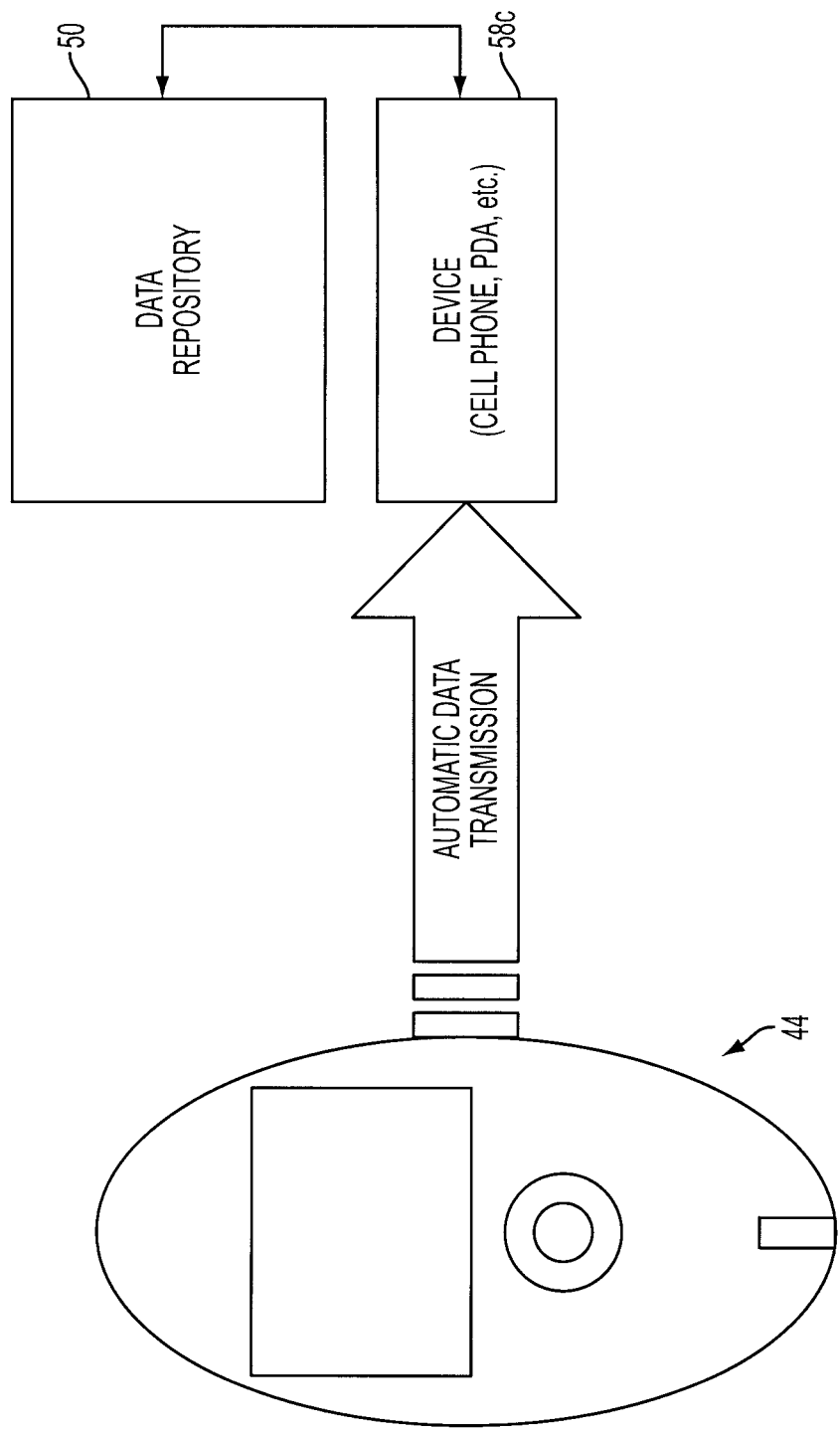
FIG. 9 is a block diagram of a wireless meter employing Bluetooth or ZigBee connectivity in accordance with an exemplary embodiment of the present invention.

FIG. 9 illustrates a blood glucose meter 44 with the communications interface 104 circuit having a built-in Bluetooth or ZigBee communications capability for automated data transmission to the repository 50 via a user device 58c such as a cell phone, PDA, and the like, via the internet 56 and/or a cellular network 54.

Figure 10B:
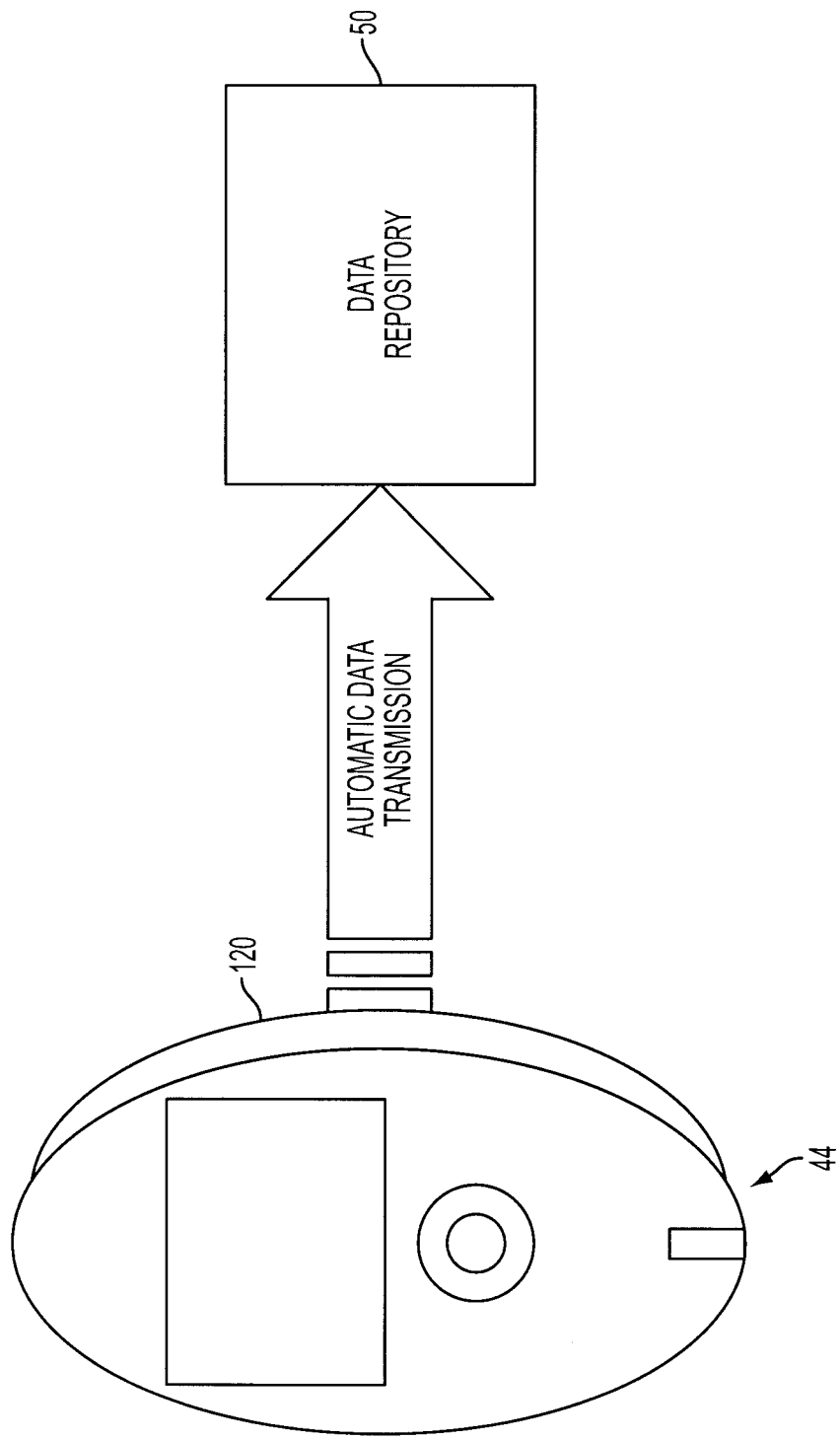

FIGS. 10A and 10B illustrate a blood glucose meter 44 that communicates with the repository 50 via a cellular network 54. As shown in FIG. 10A, the blood glucose meter 44 can have a cellular communications chip built into it as the communications interface circuit 104. Alternatively, the blood glucose meter can be provided with the cellular modem attachment 120, as shown in FIG. 10B.

Figure 11B:
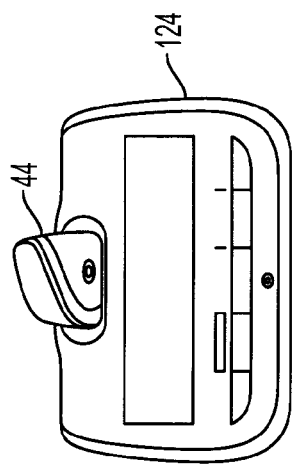
FIGS. 11A, 11B and 11C are, respectively, a perspective view, a top view and a side view of a base station and meter in accordance with an exemplary embodiment of the present invention.
Figure 11C:
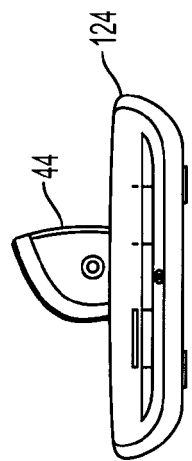
Figure 11A:
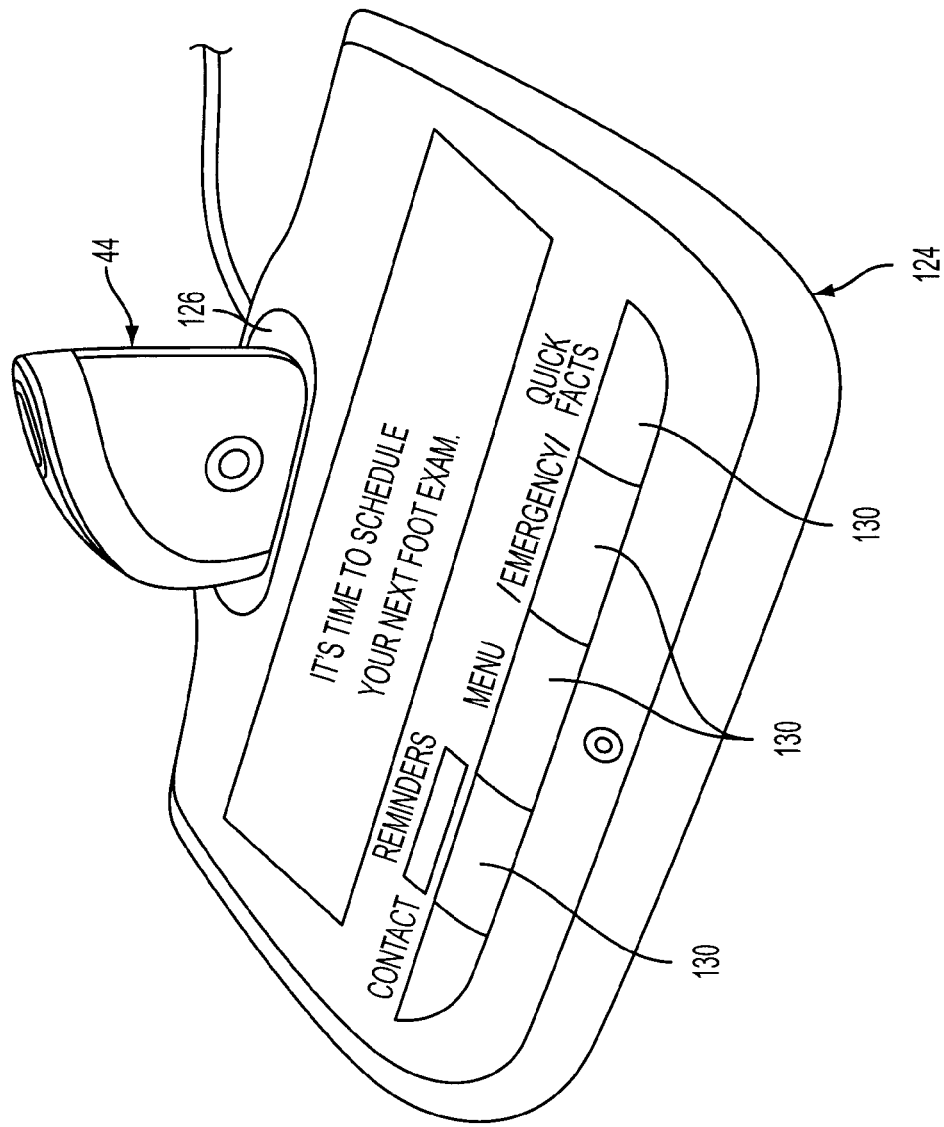
Figure 11E:
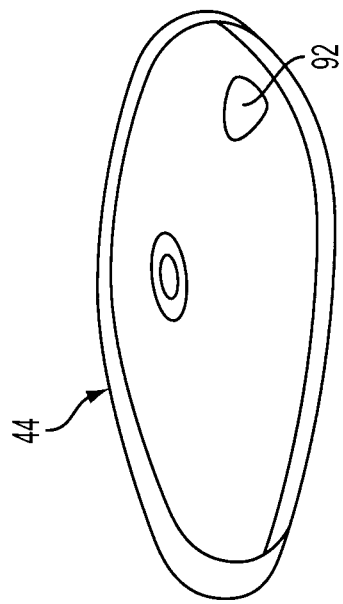
FIGS. 11D, 11E and 11F are respective views of a base station and meter, that is, a meter-only perspective view, and meter side view showing a port to connect with base station, and block diagram of docking station components and meter components with corresponding interfaces for connection to each other, in accordance with an exemplary embodiment of the present invention.
Figure 11D:
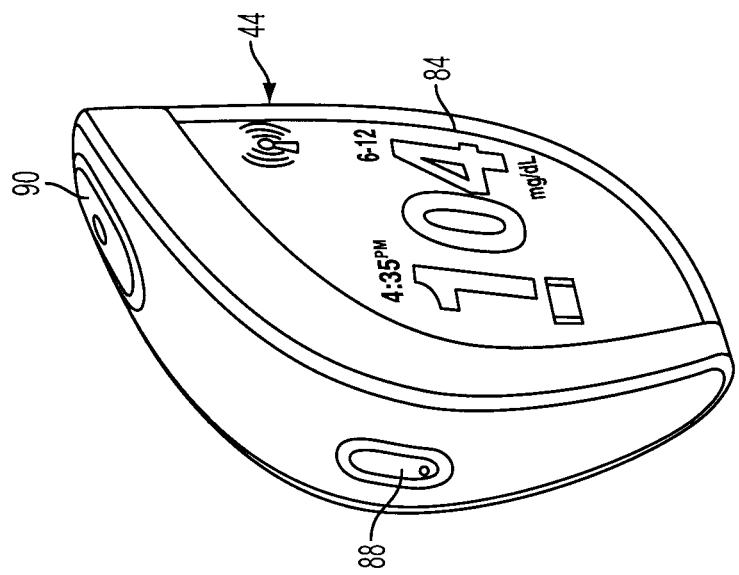

In accordance with the another exemplary embodiment of the present invention, a blood glucose meter 44 can be configured for use with a docking station 124, as shown in FIGS. 11A, 11B and 11C, in lieu of having a communications interface circuit 104 and antenna 106 as described above in connection with FIG. 5A. The docking station 124 comprises a cradle 126 for receiving the blood glucose monitor 44, a display 128, and a number of user buttons or controls indicated generally at 130. The buttons indicated at 130 comprise, but are not limited to, a button for contacting specified persons such as a physician, a button for reviewing reminders sent to the docking station from the repository in accordance with instructions from a disease management representative or physician, a button for displaying menu options on the display 128, an emergency button for one-touch dialing of an emergency number such as 911, and a button for indicating quick facts on the display regarding diabetes management. Among the menu options is a send option to send recent blood glucose test results to the repository 50 when the meter 44 is in the cradle 126. With reference with FIGS. 11D and 11E, the portable meter 44 has a display 84, a test strip input 88, and on/off button 90 and a port 92 for connecting to a corresponding connector in the cradle 126.

Figure 11F:
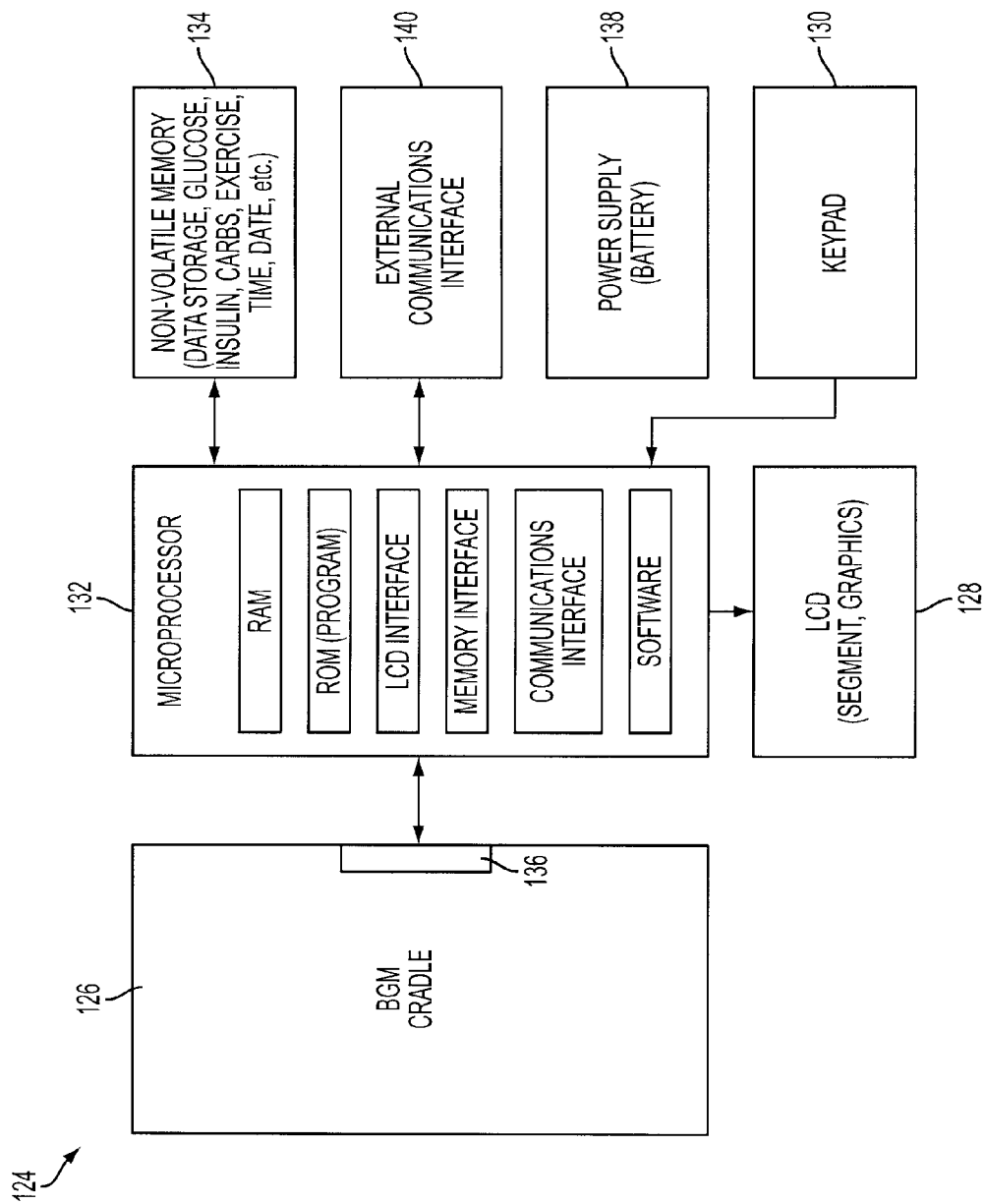

With reference to FIG. 11F, the docking station 124 comprises a programmable processor 132, a display 128, a memory device 134, a connector 136 for electrically communicating with the meter when the meter is inserted in the cradle, a number of buttons and other user input devices 130, a communications interface 140 to the repository via the internet or a wireless network and a power supply 138. The meter 44 has a test strip reader 114, a processor 96, a memory 98, a display 108 and on/off button 90 or other user input device, and a connector (not shown) for electrically communicating with the docking station when the meter is inserted in the cradle.

Figure 12B:
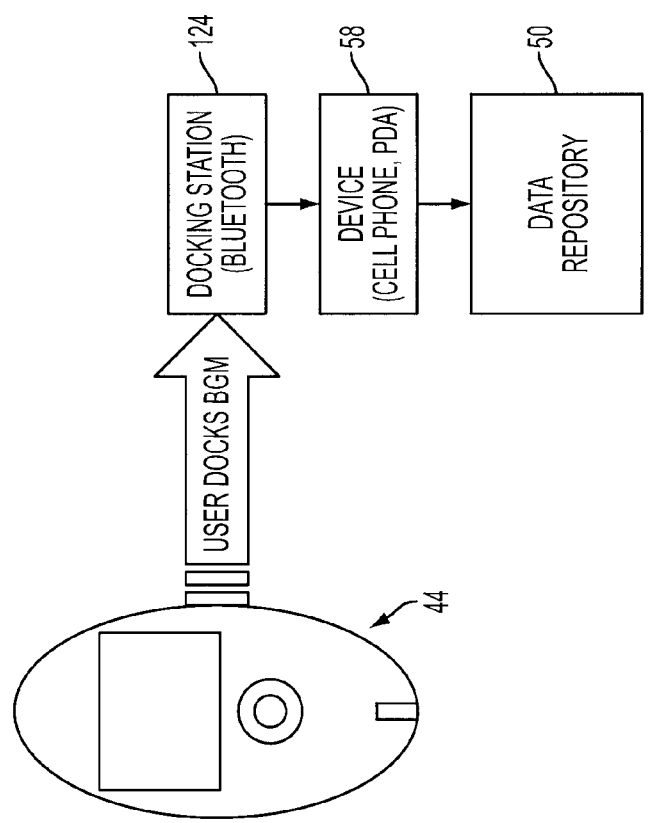
FIGS. 12A and 12B are block diagrams of a base or docking station and a meter having connectivity to a repository directly or via a device in accordance with an exemplary embodiment of the present invention.
Figure 12A:
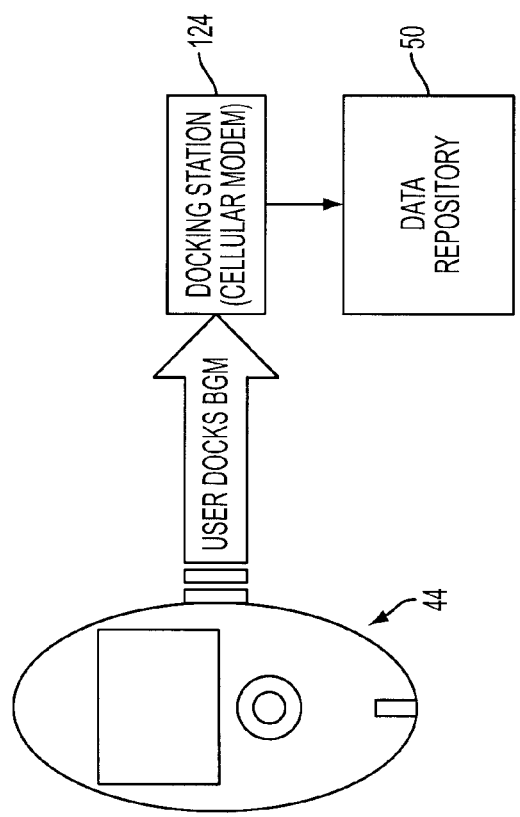

As shown in FIGS. 12A and 12B, when the blood glucose meter 44 is docked in the docking station 24, the docking station can communicate via wireless technology such as Bluetooth to a device 58 such a cellular phone or PDA which, in turn, communicates with the repository 50 via a wireless network or the internet. Alternatively, the docking station 124 can be provided with the cellular modem such that, when the meter 44 is in the docking station cradle 124, the docking station 124 can transmit test results to the repository 50 via the cellular network.

FIGS. 13-16 illustrate other types of devices having a blood glucose meter and radio frequency connectivity to the repository.

FIGS. 13A, 13B and 13C illustrate a cellular telephone 142 having a built-in test strip reader 144 and display 146 similar to that of the blood glucose reader described above in connection with FIGS. 11B and 11C.

Figure 14:
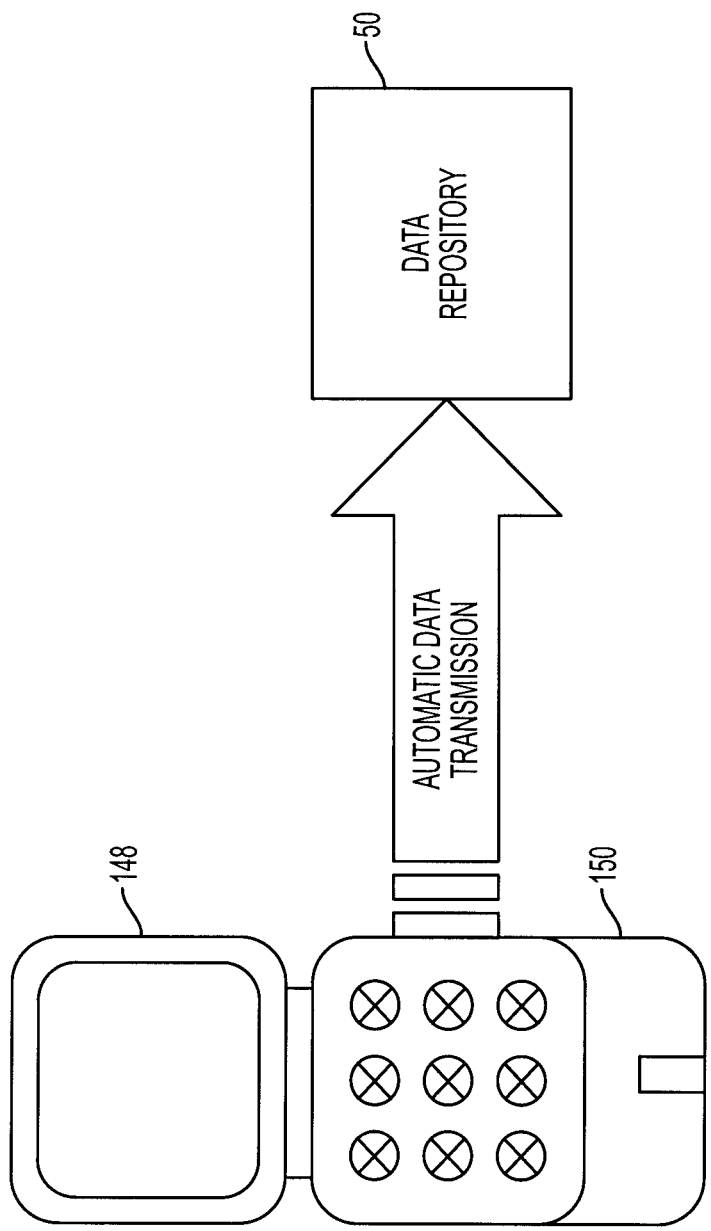
FIG. 14 is a block diagram showing connectivity of a BGM in a cell phone in accordance with an exemplary embodiment of the present invention.

As shown in FIG. 14, a cellular telephone 148 can have automatic data transmission connectivity to the data repository 50 via the cellular network. FIG. 14 illustrates a cell phone 148 with a BGM attachment 150.

FIGS. 15A through 15D are various views of an insulin delivery device 160 such as a syringe that is provided with an RFID tag for transmitting information such as syringe identification number, and data stored in a non-volatile EEPROM in the tag such as insulin-type delivered by the syringe, amount, insulin type, and so on. The amount can be detected and stored based on plunger motion. Accordingly, when a glucose meter 44 is proximal to the syringe 160 to create a sufficient electromagnetic field, the RFID in the syringe can be activated to send the data relating to the insulin dose delivered by the syringe.

Figure 15D:
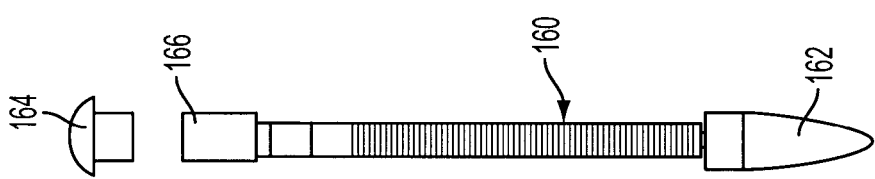
FIGS. 15A, 15B, 15C and 15D illustrate a connected syringe in accordance with an exemplary embodiment of the present invention.
Figure 15C:
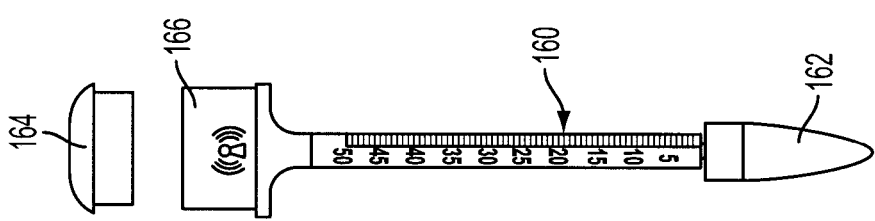
Figure 15B:
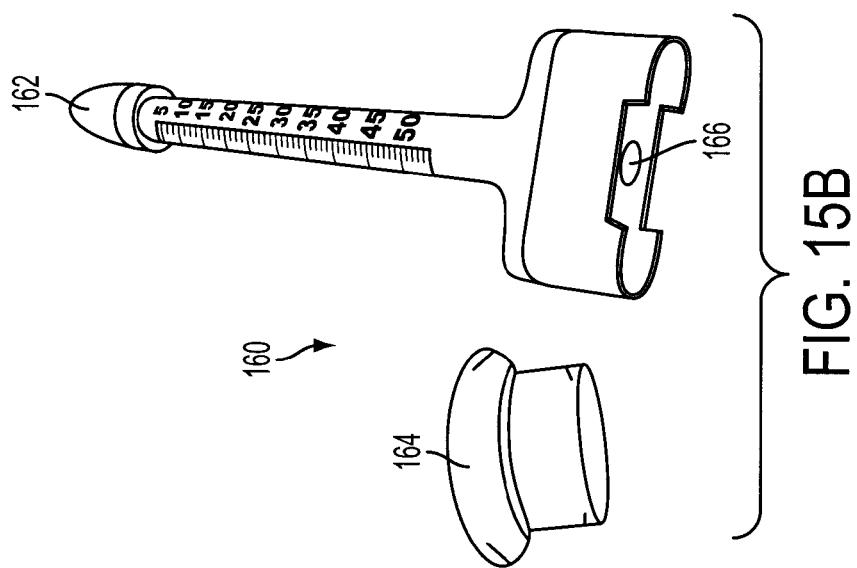
Figure 15A:
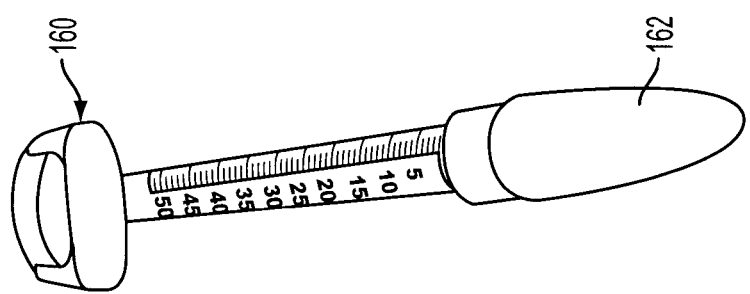

FIG. 15A is a perspective view of the syringe 160 having a cap 162 on the needle. FIG. 15B is a perspective view of the syringe 160 having the cap 164 at the top of the reservoir 166 for the insulin removed. The top of the reservoir can be configured with the RFID tag, the plunger and the plunger motion sensor. FIGS. 15C and 15D are front and side elevated views of a syringe 160 having the reservoir cap 164 removed.

FIGS. 16A through 16E are various views of another insulin delivery device 170, that is, an insulin pen having RF connectivity in accordance with an exemplary embodiment of the present invention. FIGS. 16A and 16B are perspective views of the pen 170 with the cap 172 on. FIG. 16C is a perspective view of the pen 170 with the cap 172 removed and the insulin delivery mechanism exposed. FIGS. 16D and 16E are top and side elevated views of the insulin delivery pen with the cap on.

As indicated in FIGS. 16B, 16C and 16D, the insulin delivery pen 170 has a display 174 for indicating insulin dose and other information such as mix amount, time and date of insulin delivery. The pen 170 is provided with a communication circuit (not shown) for communicating the data to the repository using one of the RF communication pathways described above in connection with the blood glucose meter 44.

Figure 17:
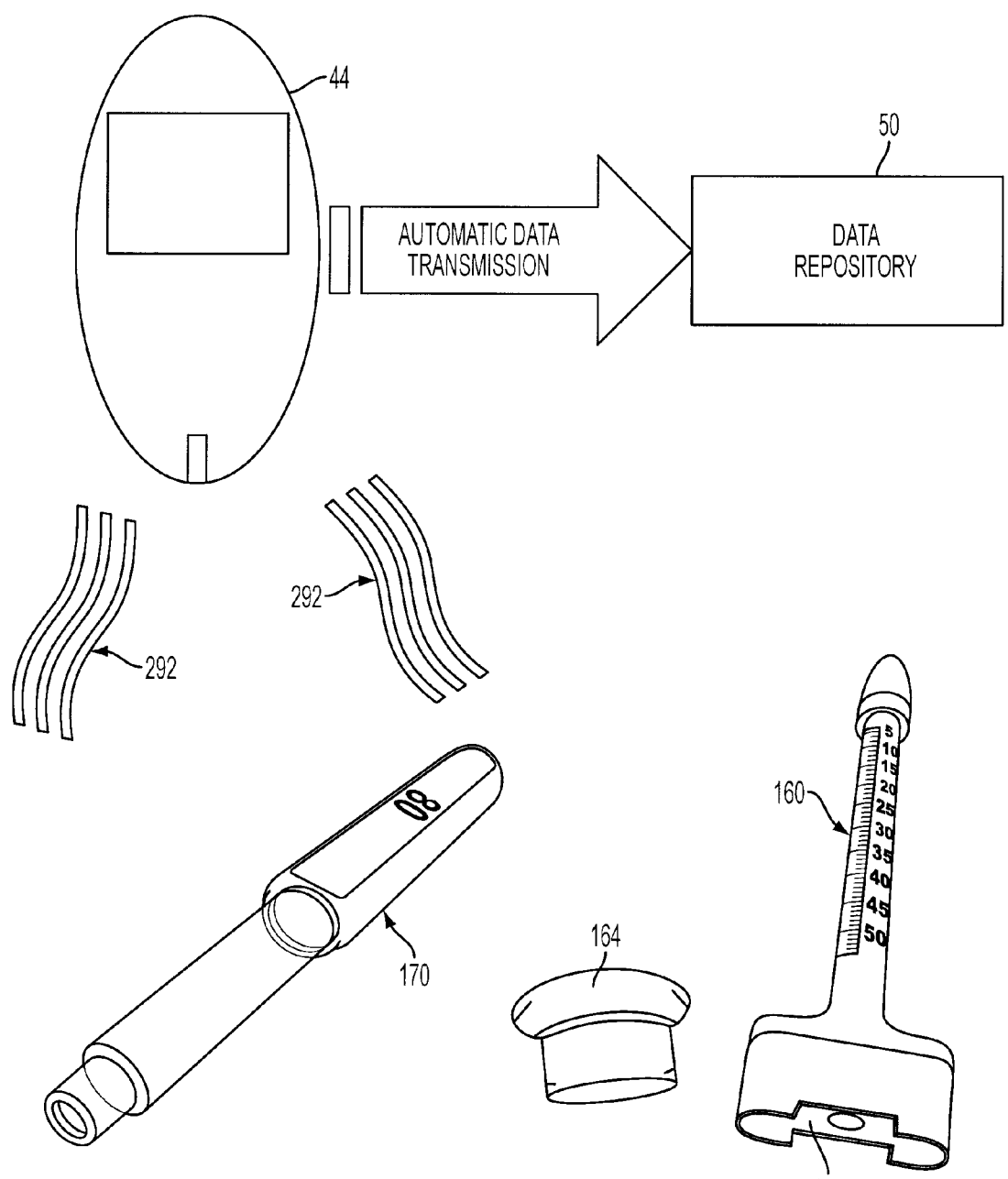
FIG. 17 is a block diagram showing connectivity of a pen or syringe in accordance with an exemplary embodiment of the present invention.

The exemplary insulin delivery devices shown in FIGS. 15A-15D and FIGS. 16A-16E require no patient or caregiver involvement to communicate the insulin delivery data to the repository. The connected syringe data can be sent when the meter data is sent and basically coincides with blood glucose testing. The connected pen data can be automatically transmitted to the repository 50 upon detection of complete insulin delivery. As shown in FIG. 17, the insulin delivery data can therefore be sent using, for example, the wireless transmission methods described above in connection with FIGS. 4 through 10. Other injection devices can include, but are not limited to, microneedle delivery, external and implanted insulin pumps with or without PC interfaces. With further reference to FIG. 17, a meter 44 can therefore be configured to communicate with a pump, for example, via a local network and with the repository 50 via a wide network. In accordance with the exemplary embodiment of the present invention, the pens 170 are configured to store multiple dose information which can be transmitted automatically to the repository.

Exemplary embodiments of the present invention allow for reactive and real-time management of diabetes management data and information by diabetes management stakeholders, in particular stakeholders such as disease management companies, insurers, healthcare networks and employers whose functions have not, in the past, been optimized. As stated above, the automatic transmission of blood glucose meter data and insulin delivery device data to a repository 50, and the use of the repository 50 to also collect, store and access diabetes management information such as food intake and exercise and other health parameters such as blood pressure and cholesterol, allow for increased patient compliance and more comprehensive information for review by disease management case workers, physicians, insurers, and other diabetes management stakeholders. DMCs, in particular, benefit form the real-time and comprehensive information and data provided to the repository 50 in accordance with an exemplary embodiment of the present invention. In the past, problems commonly experienced by disease management companies included lack of real-time data access (i.e., because much of the data was collected via telephone conversations between representative and patients), insufficient physician involvement, inability to scale operations cost-effectively and therefore costly case management. A number of improved disease management operations will now be described with reference to FIGS. 18A and 18B and in accordance with exemplary embodiments of the present invention.

Figure 18A:
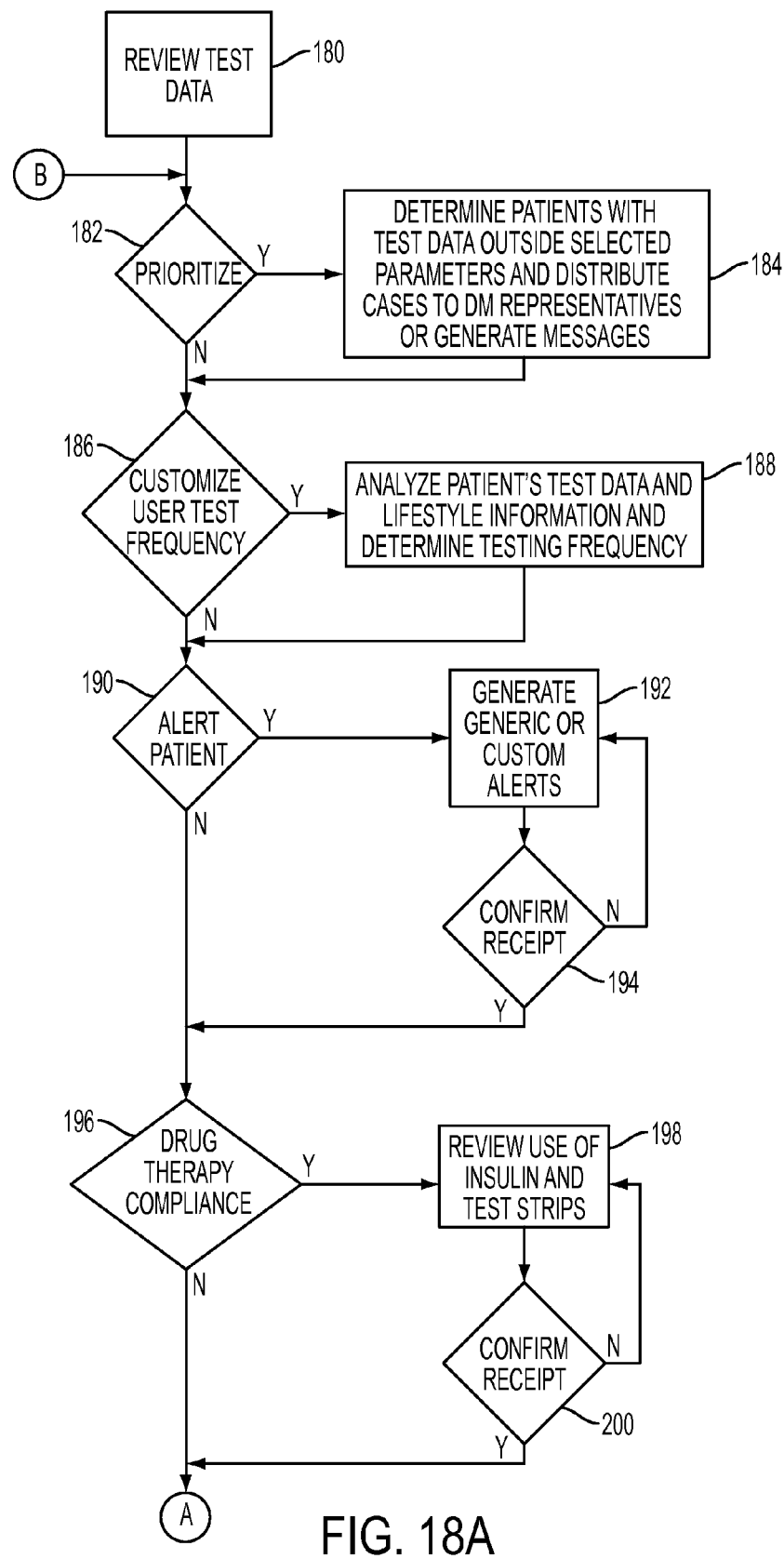
FIGS. 18A and 18B illustrate a flow chart for use of test data by a DMC in accordance with an exemplary embodiment of the present invention.
Figure 18B:
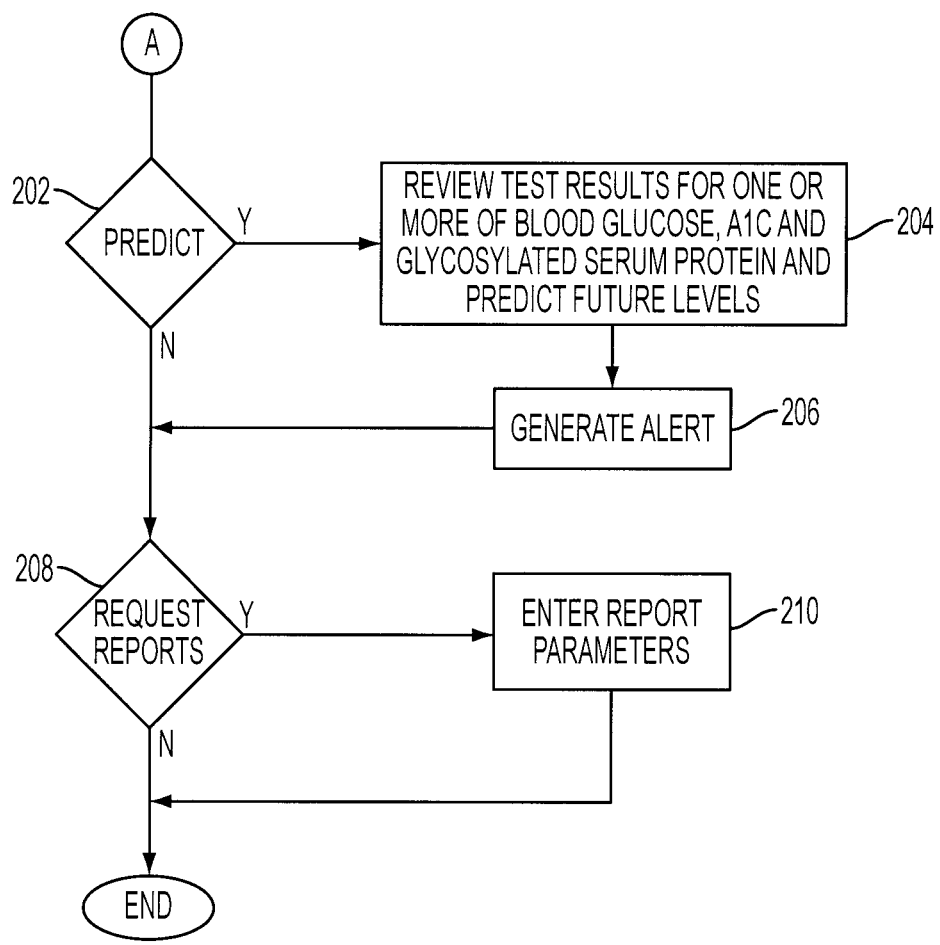

Referring to FIGS. 18A and 18B, disease management companies can now review (block 180) the various records available for selected patients in the repository 50 and determine when blood glucose test results and other test results such as A1c testing are outside selected parameters for respective patients based on variations in a patient's blood glucose levels and other test results. The disease management company can prioritize which patients need to be contacted by a representative and provided with additional educational information (blocks 182 and 184). For example, an algorithm at the repository can use parameters specified by a stakeholder to determine those patients whose test results indicate that prompt attention or intervention is needed. A report generating module at the repository 50 allows for exception reporting, that is, selection of patients whose parameters meet selected criteria and need an alert message to be sent via the two-way wireless pathway of the present invention, or simply generation of an exception report (blocks 208 and 210). Thus, a stakeholder can use the reports generating ability of the repository 50 to know how many hypoglycemic events occurred among their patients in a given time period. In addition, a disease management company can also improve the assignment of cases among disease management representatives to facilitate their case load management. In addition, variations among a patient's blood glucose data, as well as meal-time habits and other stored information, can be analyzed to allow the data management company to customize the frequency with which a patient tests blood glucose levels and performs other tests such as A1c testing (blocks 186 and 188). Users can then be sent reminders via the base station or the display on wireless blood glucose meters regarding when to test, if a particular test has been overlooked by the patient, or alerts when levels are outside a selected range (blocks 190 and 196). Alerts can be custom or generic alerts in accordance with an aspect with the present invention.

With continued reference to FIGS. 18A and 18B, stakeholders can use the repository and two-way radio frequency communications between themselves and patients (i.e., via meters, docking stations, cellular phones, computers, PDAs or other devices) via the communication pathways illustrated in FIG. 4 or other networks such as the public switch telephone network (PSTN). The two-way communications provided by the present invention between the patient and other diabetes management stakeholders allows determining drug therapy compliance (block 196) through the analysis of repository 50 data relating to test strip use verification and insulin doses administered (block 198), as well as for the confirmation (block 194 and 200) of receipt of an alert sent to the patient (e.g., when a test blood has expired or is defective, when test blood glucose levels are outside a selected range, and so on) (blocks 192 and 206). The repository 50 can comprise different test data such as A1c and glycosylated serum protein test data for analysis by a stakeholder for short-term, mid-term and long-term evaluation of blood glucose levels and prediction of events for a specific patient such as blood glucose levels falling outside a desired range (block 202 and 204). The repository 50 allows for generation of a greater variety of reports since the data is more comprehensive. For example, disease management companies can perform compliance reporting for selected ones of groups of patients (diabetes patient population trends reports), and real-time exception reporting. Reports can be generated for different stakeholders (e.g., patient, case manager and healthcare provider) that are linked but also have unique portal space in the repository such that notes can be posted and responded to among the stakeholders. Also, reports can be represented differently on the respective stakeholders' computer screens to have varying information and functional features, depending on the stakeholder viewing the report.

Thus, the exemplary embodiment of the present invention provides stakeholders with a means to move from reactive disease management to real-time and proactive disease management and therefore provide such direct benefits as increased productively for case workers and reductions in management cost and time expended, improved clinical outcomes, increased patient care and satisfaction (e.g., due to the real-time aspect of viewing and responding to test data), and greater healthcare team involvement. These benefits lead to such secondary benefits to DMCs as increased patient enrollment and business opportunities. Insurers, for example, can better evaluate financial impact of a disease management program based on outcomes and trends reports that can be obtained from the repository 50 described above in accordance with an exemplary embodiment of the present invention, and receive better cost effectiveness from a contracted disease management company. Using one or more of the exemplary embodiments of the present invention described herein, healthcare networks can increase productivity by spending less time gathering data and more time providing care to patients. Repository 50 data can be made available to multiple hospital and clinic sites. Patients are more satisfied when healthcare networks enroll in a system in accordance with an exemplary embodiment of the present invention because patient data is available anytime and wherever the patient goes, prescriptions are automated and patient data is securely available to the right people involved with a patient's disease management.

The exemplary embodiment of the present invention also allows disease management companies and other stakeholders to monitor drug therapy compliance. For example, diabetes management stakeholders can review medication dosages reported automatically, as well as collected information in the repository regarding test strip lot and corresponding test results and determine if a patient is maintaining a physician-directed schedule for testing and otherwise managing blood glucose levels. As described above, alerts can be sent when blood glucose levels are outside a selected range or test strips have expired or otherwise need to be replaced. As will be described below in connection with FIG. 19, tracking of test strip use in accordance with an exemplary embodiment of the present invention allows for more effective use of test strips, better control over test strip quality and quantity delivered to patients and more efficient billing to Medicare.

The automated transmission of blood glucose results and test strip lot number and meter calibration data allows for stakeholders with the access to the repository 50 to determine those test strips that have actually been used. Currently, Medicare guidelines determine the number of test strips that are sent per month to diabetes patients. Currently, there is no way to track whether the test strips are actually used. Mail order companies are permitted to bill Medicare for the maximum amount of test strips allotted to a patient regardless of whether the test strips go largely unused by the patient. Mail order companies need only contact the patient once each month before sending the Medicare-directed number of test strips to that individual and then billing Medicare for those strips. Accordingly, a significant amount of test strips paid for by Medicare can go unused and without any method of detecting the magnitude of such waste.

Figure 19:
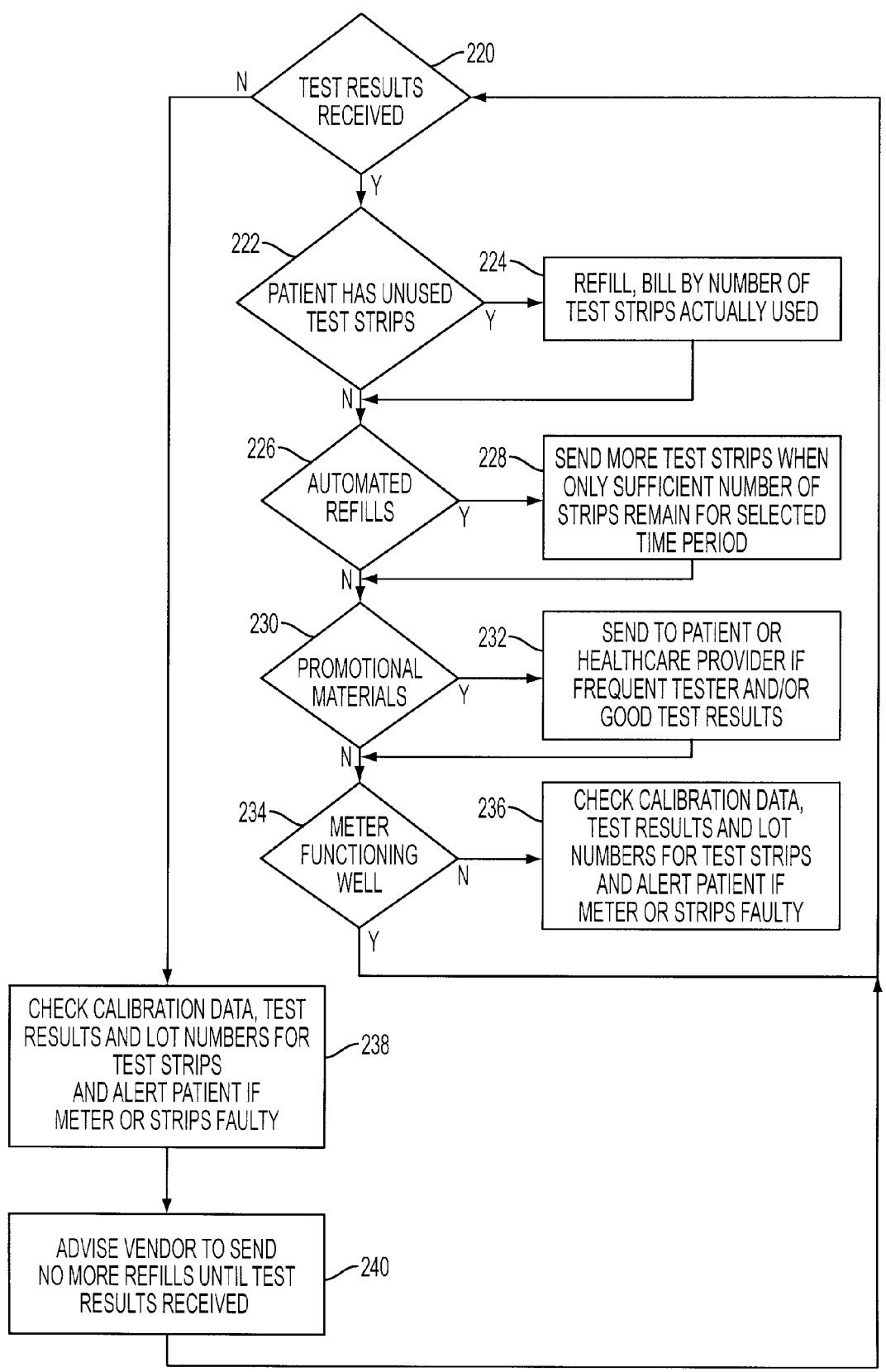
FIG. 19 is a flow chart illustrating use of test data to control test strip refills, promotional items and the like in accordance with an exemplary embodiment of the present invention.

With reference to FIG. 19, an exemplary embodiment of the present invention resolves this problem through the automatic transmission of test results from meters (e.g., meters 44, 142 or 148) to the repository 50 without any user interaction or interference. The repository 50 can be configured to store the number of test strips allotted by Medicare to a patient, the number of recommended tests per day the patient is to undergo, the number test results that have been received, and determine how many unused test strips a user has within a particular month (blocks 222 and 240). Based on this information, it can be determined whether a user needs a refill of test strips. Billing can therefore be on the basis of number of test strips that have actually been used, representing a significant savings to Medicare and other payors over current wasteful practices. The repository 50 and the automated communications described herein in accordance with exemplary embodiments of the present invention also allow for determination of refills and automated fulfillment of same since the number of unused test strips that are left can be determined (blocks 226 and 228). A vendor can use these automated communications and the repository 50 to estimate when a patient is going to be out of test strips and can automatically send more when the patient has only, for example, a two week supply left Alternatively, a vendor can be sent a message to send no more refills until a prescribed number of test results are received (block 240).

With continued reference to FIG. 19, the repository 50 also allows for review of testing practices and blood glucose results and can send promotional material from pharmacies or pharmaceutical companies to selected patients. As described above, the connected blood glucose meter (e.g., an RF meter 44 or a cell phone meter 142 or 148) provides for ability to send not only messages from the patient's healthcare team, or educational content to the patient, but also other types of messages. For example, as part of a business model in accordance with an exemplary embodiment of the present invention, advertising can be sold to companies who have targeted messages that they want these patients to receive (blocks 230 and 232). For illustrative purposes, a pharmaceutical company that is introducing a new diabetes therapy can therefore buy an advertisement that is transmitted to those patients whose health profile fits a potential target for the new therapy. These profiles can be obtained using algorithms and report generation operations of the repository 50.

In addition, as indicated in FIG. 19, overall accuracy of test strips and meters can be monitored by reviewing blood glucose levels, test trip lot numbers and meter calibration information (block 238). Finally, if test results are consistently outside desired parameters or nonexistent, alerts can be sent in the event that the test strips are defective or the meter 44, 142 or 148 is malfunctioning (blocks 234, 236 and 238). Accordingly, vendors can be advised to send replacement strips for malfunctioning or expired tests strips. Thus, automated test results reporting and management of other data such as test strip lot numbers and patient data such as recommended frequency of testing and therefore test strip usage tracking presents many advantages over current diabetes management systems such as tracking of expired or defective test strips, eliminating abusive practices such as test strip hoarding and unfair billing to Medicare or Medicaid, and monitoring associations between test strips and meters, to name a few.

Currently, Medicare requires mail order companies to call and ask patients if they need more test strips before sending them. Mail order companies can avoid the time and expense of making such calls since the number of test strips actually used can be tracked using the connectivity and repository of the present invention. Further, DMCs find the hiring of staff nurses to manage case loads to be difficult and expensive. The device connectivity and repository 50 described herein in accordance with exemplary embodiments of the present invention, however, can provide patients with a virtual coach and reduce reliance on nurses and other case managers. Using algorithms at the patient device 44, 142 or 148 or in the repository 50, the collected and stored data and information at the repository 50 and the two-way communication function described herein, points of education can be generated and sent via message to the patient as needed to improve medical outcomes.

Figure 20:
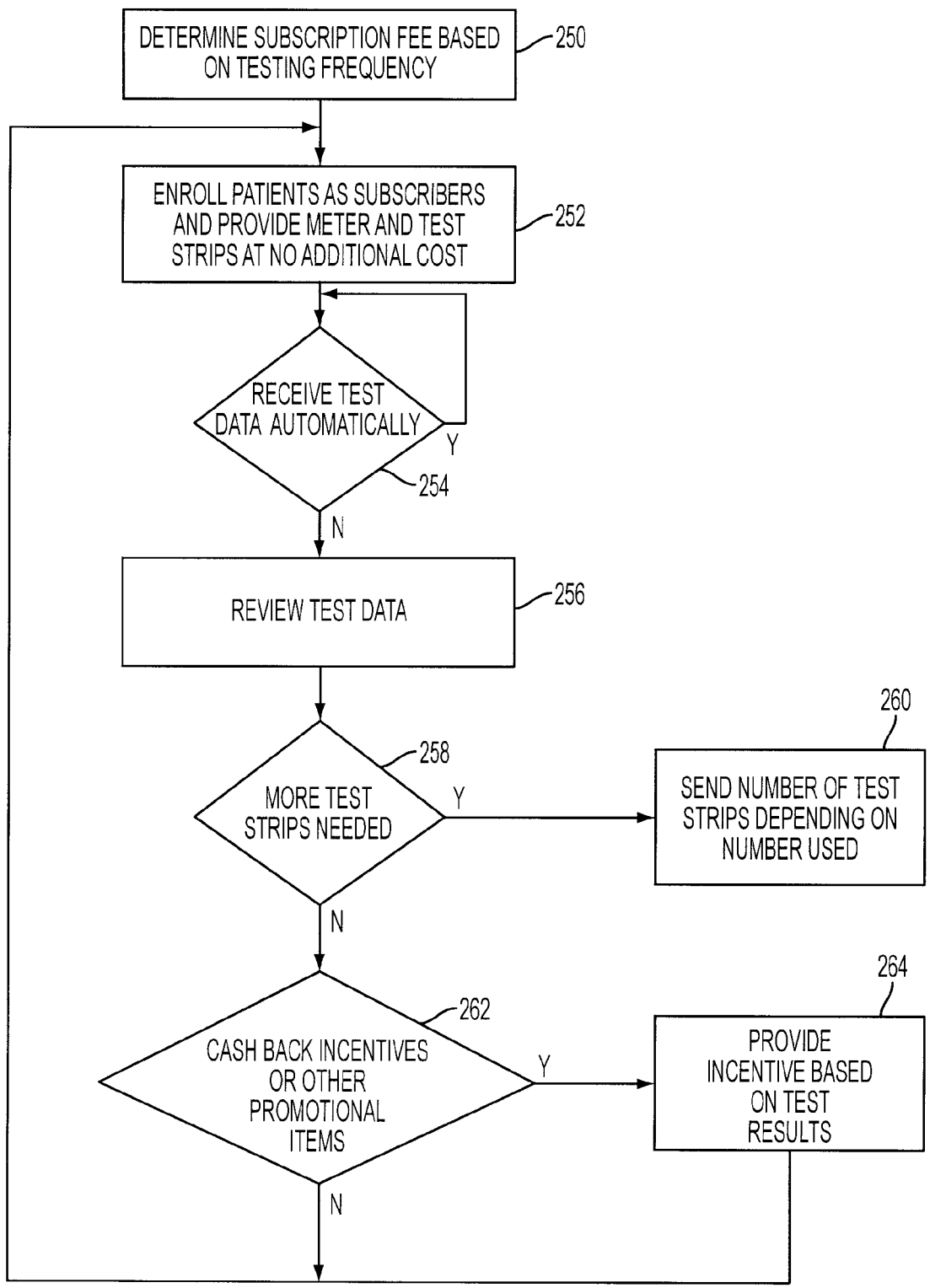
FIG. 20 is a flow chart illustrating use of test data to enroll patients in monthly service connectivity contract and manage incentives disbursements and the like in accordance with an exemplary embodiment of the present invention.

The exemplary embodiments of the present invention also allow for different and advantageous programs to be implemented. For example, with reference to FIG. 20, a cellular network-based system can be implemented wherein a monthly subscription fee can be determined based on test frequency and the number of times test data is uploaded to the repository (block 250). Once monthly subscribers are enrolled, they can be provided with blood glucose meters and test strips at no cost or at nominal cost, obviating the above-mentioned abusive practices of billing Medicare for unused strips (block 252). As the test data for a particular subscriber is uploaded, it can be reviewed to determine if more strips are needed (blocks 254, 256, 258 and 260). Also, patients' overall ability to manage the blood glucose within desired ranges can be determined and cash-back incentives or other promotional items can be provided to physicians and/or patients exhibiting improved diabetes management through their improved comprehensive test results (blocks 262 and 264). In addition, the third party payor (e.g., Medicare) would only pay for those test strips that had an associated result in the data repository 50 thereby reducing the likelihood of fraud and abuse in the system of reimbursement for diabetes supplies.

In accordance with an aspect of the present invention, radio frequency identification (RFid) technology is employed to realize advantages over existing disease management devices. The term "radio frequency identification transponder" is used to refer to any of a class of compact radio receiver-transmitters that are powered by an ambient radio frequency field. The transponder is accessed by modulating the field with an appropriate communication signal. The reaction can be a responsive signal, a change in the transponder, or both. The content of the communication signal and the response of the transponder are limited by the memory and control functions provided by the transponder and by the access time bandwidth available for communication. Within those limits, the transponder can be read and written in a manner similar to other digital memory devices used to store and retrieve digital information. Radio frequency identification transponders are widely available in a variety of forms. These devices include a non-volatile memory, such as an Electrically Erasable Programmable Read-Only Memory (EEPROM) semiconductor component integrally contained in the transponder. Stored in the non-volatile memory are encoded data. The radio frequency identification transponder also contains an antenna. The shape of the transponder and the antenna can vary depending on the specific embodiment. Memory and any control functions are provided by chip mounted on the support and operatively connected through the leads to the antenna.

Figure 21A:
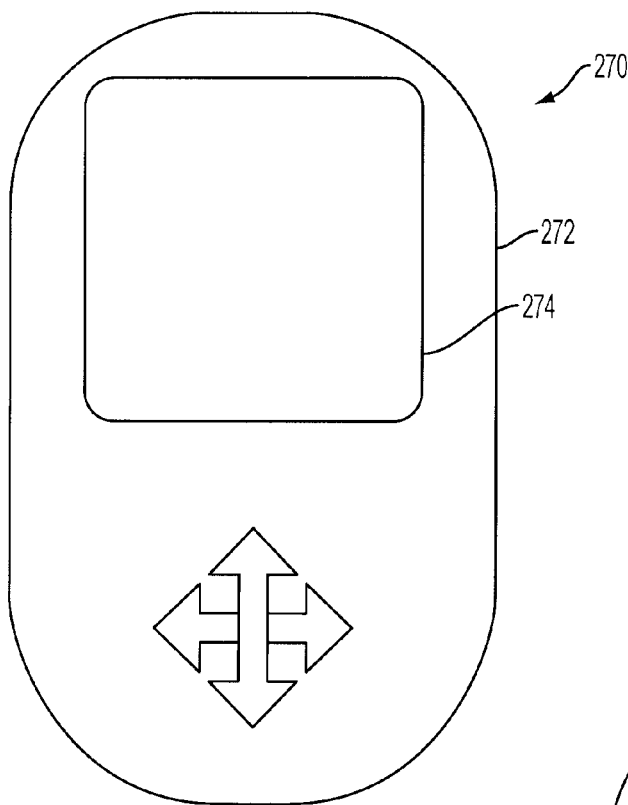
FIGS. 21A and B show, respectively, the front and back views of a blood glucose monitor containing a radio frequency identification transponder in accordance with an exemplary embodiment of the present invention.
Figure 21B:
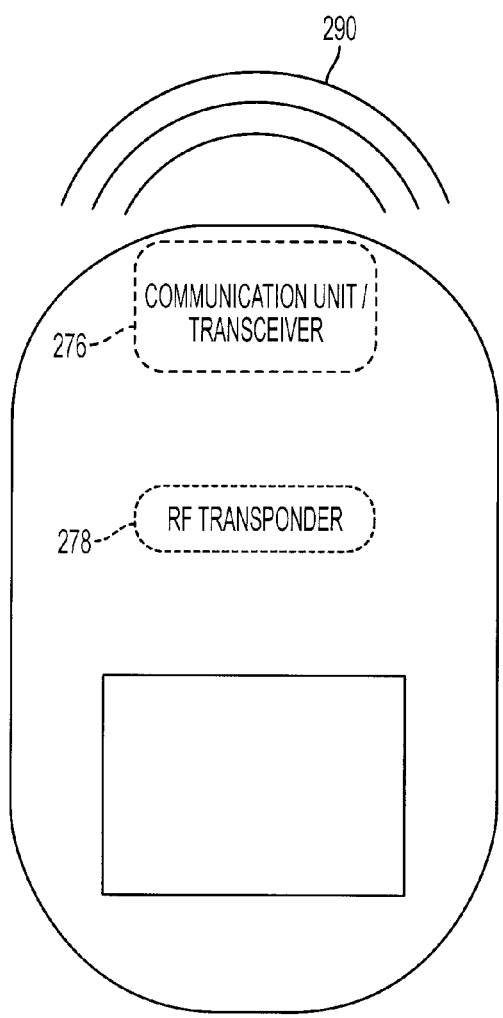

In accordance with an exemplary embodiment of the present invention, a blood glucose monitor 270 is provided which has a body 272, a glucose sensor (not shown) mounted in the body, a display 274, a radio frequency identification transceiver 276, and at least one radio frequency identification transponder 278 mounted within the body, as shown in FIGS. 21A and 21B. The transceiver 276 and transponder 278 are unshielded by the body. The lines 290 represent an ambient-frequency field generated by the transceiver 276.

Figure 22:
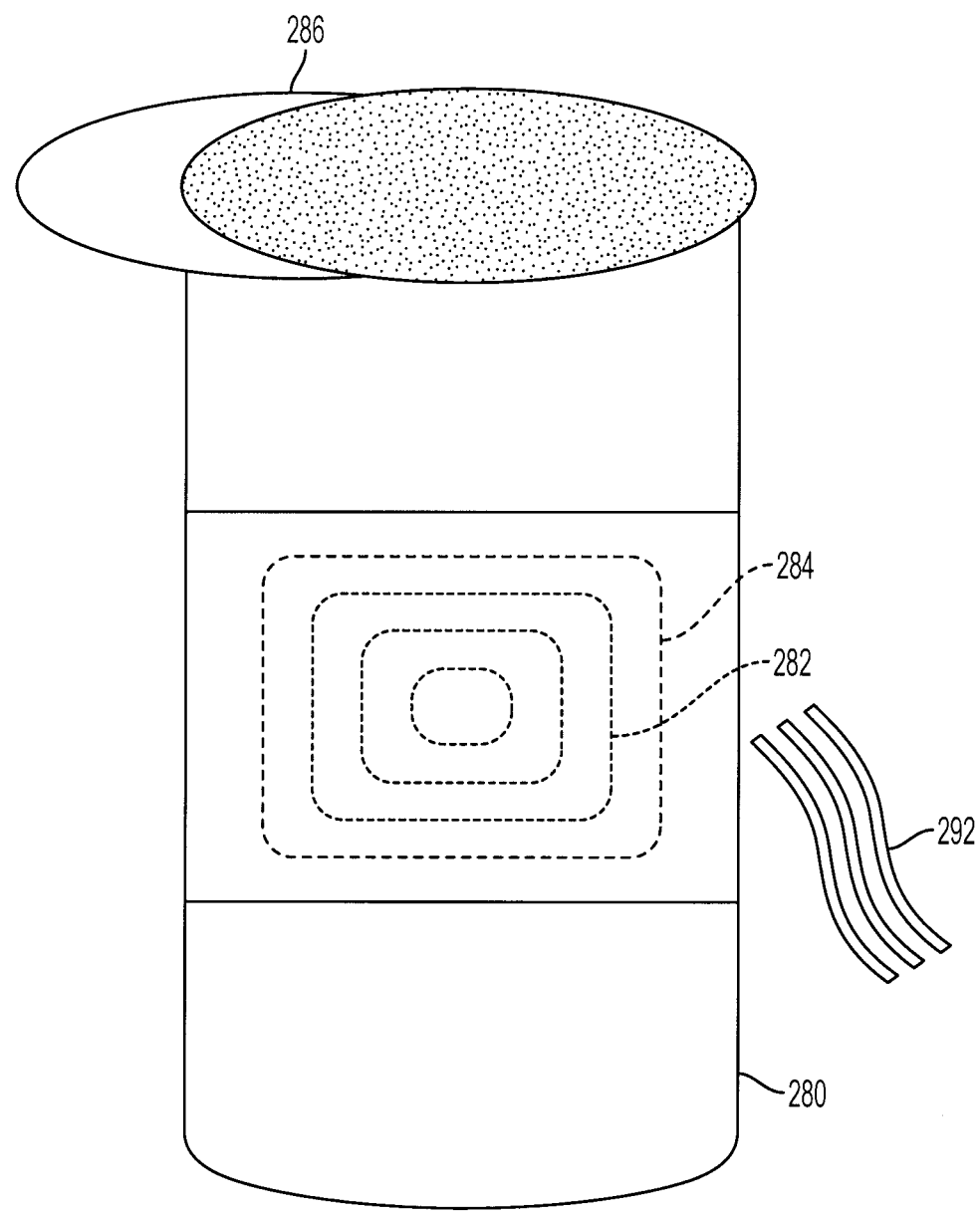
FIG. 22 shows a blood glucose test strip container with a radio frequency identification transponder integrated into the outside label in accordance with an exemplary embodiment of the present invention.
Figure 23:
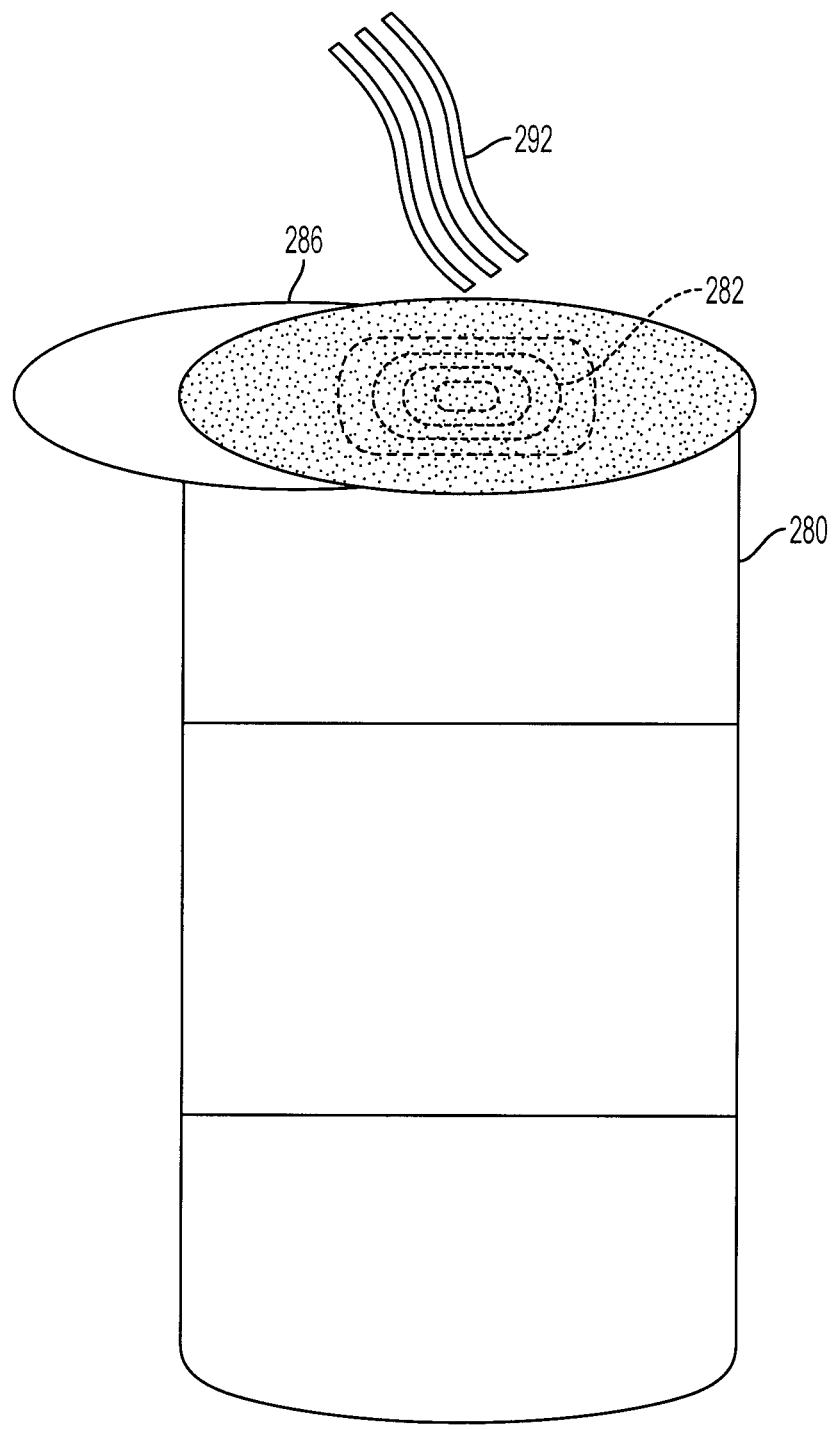
FIG. 23 shows a blood glucose test strip container with a radio frequency identification transponder integrated into the cap in accordance with an exemplary embodiment of the present invention.
Figure 24:
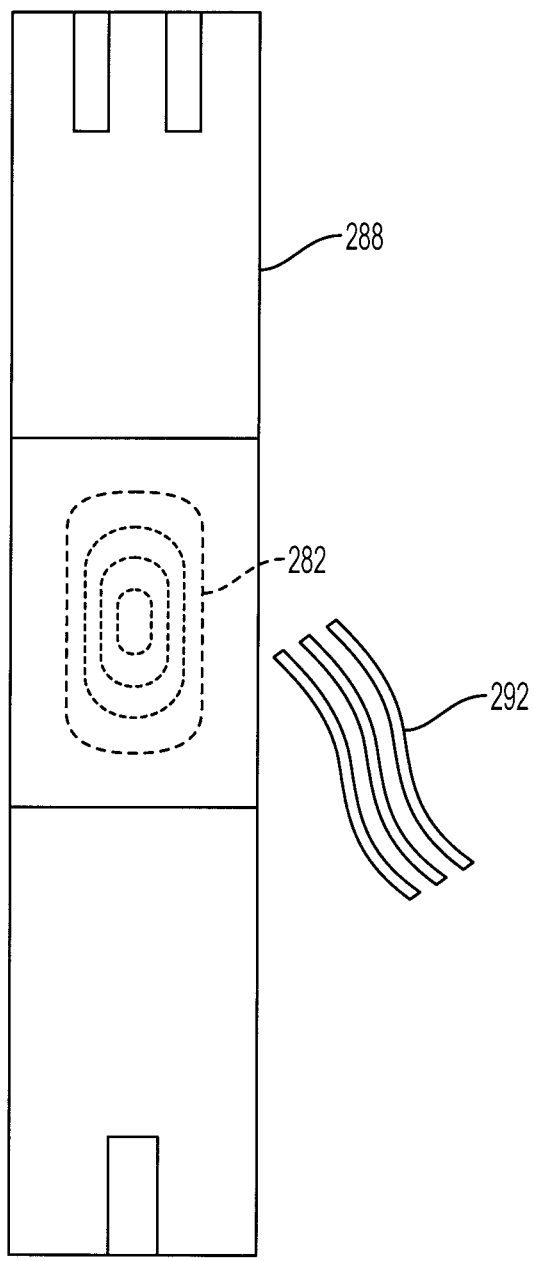
FIG. 24 shows a blood glucose test strip with a radio frequency identification transponder as part of the test strip in accordance with an exemplary embodiment of the present invention.
Figure 25:
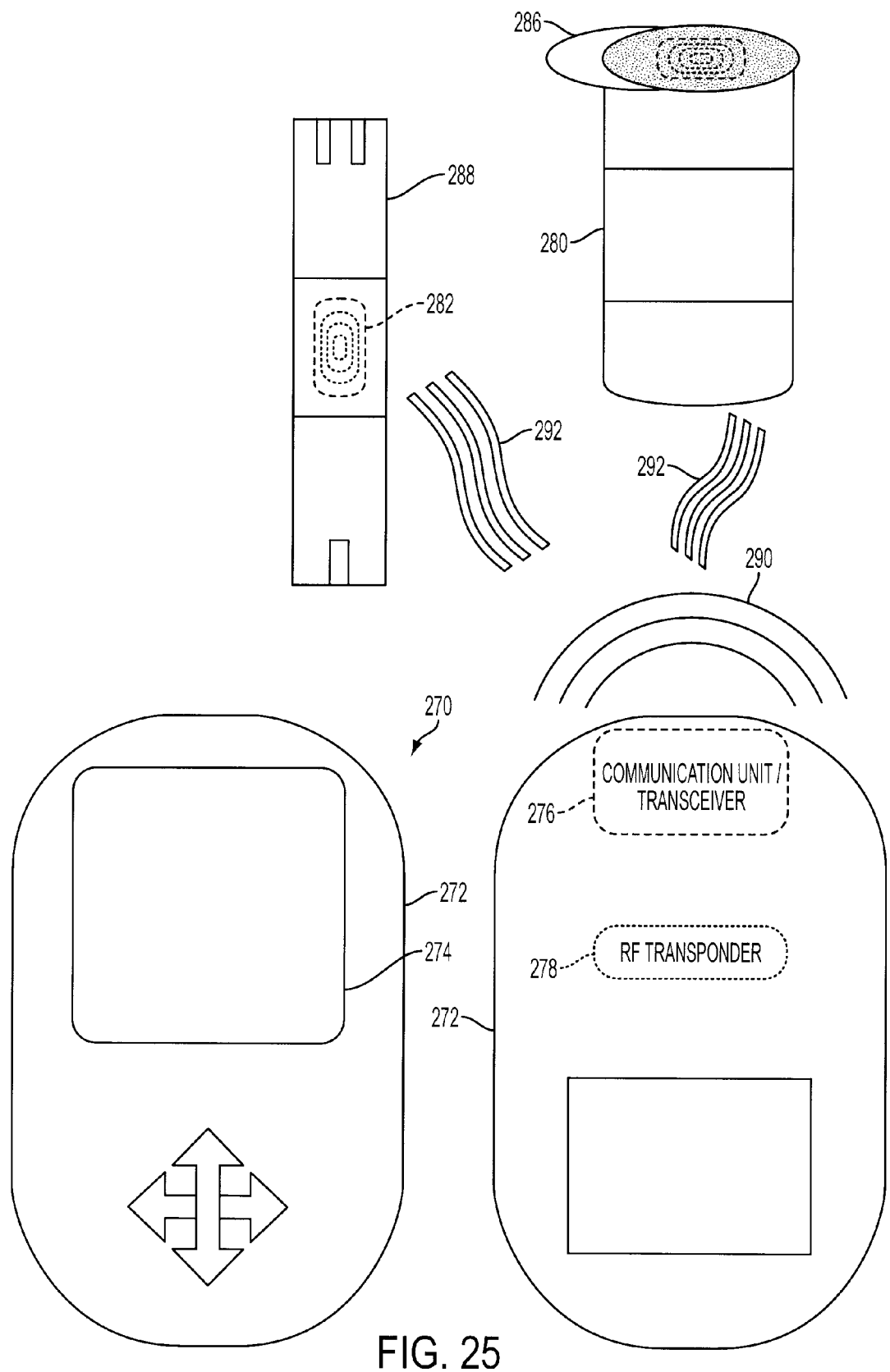
FIG. 25 shows a system where the blood glucose monitor receives data from the test strip container and the test strip in accordance with an exemplary embodiment of the present invention.

During use, a container 280 of test strips including a radio frequency identification transponder 282 (e.g., integrated into a container label 284 or the lid 286 as shown in FIGS. 22 and 23, respectively) or individual test strips 288 containing a radio frequency identification transponder (FIG. 24) have their radio frequency identification transponders 282 activated by the blood glucose monitor's transceiver 276, as indicated by the line pattern 290 in FIG. 25. This results in the container 280 of test strips, or the individual test strip 288, transmitting data comprising an encodement (indicated by line pattern 292) necessary for the monitor 270 to calculate an accurate measure of the blood glucose level in the blood sample applied to the test strip 288.

This exemplary embodiment of the present invention realizes a number of advantages and improvements over the existing diabetes management devices. The typical use of a conventional blood glucose monitor requires that the user manually enter a code number into the blood glucose monitor that corresponds to the code number printed by the manufacturer on the test strip container. This code number is a type of calibration data that ensures that the results obtained are accurate to the degree claimed by the manufacturer in the labeling for the test strips. If the user of the blood glucose monitor does not pay attention to this code number or enters an incorrect code number, the blood glucose results obtained could be significantly different than the results obtained with a correct code number. A significantly higher or lower result could lead to incorrect medical therapy by the user or the healthcare professional performing the blood glucose test. By contrast, having the encodement 292 transmitted from the test strip container or the individual test strip in accordance with the exemplary embodiment of the present invention ensures that the blood glucose test provides the most accurate result, eliminating the likelihood of an inaccurate result due to user error. Also, the encodement can contain additional information such as, for example, date of manufacture, the test strip expiration date, lot number, manufacturer identification, and logistic information such as distribution country or region. This additional information can be stored in the repository 50 and used by the system of the present invention, which is exemplified by the illustrative embodiments disclosed herein, to provide alerts or warnings about the expiration date, to enable or disable use of certain combinations of meters and test strips depending on the country or region, and to aid logistics management.

The present invention, which is exemplified by the illustrative embodiments disclosed herein, provides solutions to prior art problems. When the blood glucose test strips are manufactured and a calibration code is established for a particular lot, this code is embedded in the radio frequency identification transponder 282 of either the container 280 holding these test strips, the individual test strips 288, or both. When a container 280 of test strips or an individual test strip 288 is in close proximity to the blood glucose monitor 270, the blood glucose monitor's transceiver 276 creates a field 290 that activates the container or test strip radio frequency identification transponder 282 which then automatically transmits its embedded code 292 to the blood glucose monitor 270. The blood glucose monitor 270 then uses this code in calculating the blood glucose result that is displayed once a test strip with a blood sample has been received in the blood glucose monitor. Further, the encodements 292 can include information about the individual test, whether from the transponder in the container, the transponder in the test strip, or the transponder contained within the monitor itself. Examples will now be described.

In a first example, two elements contain radio frequency identification transponders, that is, the blood glucose monitor 270 and the test strip container 280. In this example, the close proximity of the test strip container to the blood glucose monitor is required for the monitor to receive the calibration code.

In a second example, two elements contain radio frequency identification transponders, that is, the blood glucose monitor 272 and the individual test strips 288. In this example, the close proximity of the test strip due to its insertion in the blood glucose monitor is required for the monitor to receive the calibration code.

In a third example, three elements contain radio frequency identification transponders, that is, the blood glucose monitor 270, the test strip container 280, and the individual test strips 288. In this example, the close proximity of both the test strip container and the individual test strip are used as a confirmation by the blood glucose monitor that the inserted test strip has the same calibration code as that transmitted by the test strip container.

In a fourth example, the test strip container 280 stores and transmits the calibration code, the test strip expiration date, and the lot number. These data are interpreted by the meter 270 by comparing the test strip expiration date to the current date set in the meter to determine if the test strip 288 being used has expired or not.

In a fifth example, the test strip 288 stores and transmits the calibration code, the test strip expiration date, and the lot number. These data are interpreted by the meter 270 by comparing the test strip expiration date to the current date set in the meter to determine if the test strip being used has expired or not.

In a sixth example, the radio frequency identification transponder 278 in the blood glucose monitor 270 is used for communication with other devices such as a pump or docking station or detector in warehouse or manufacturing location. In other words, a pump or docking station can transmit a field via a transceiver to determine if a BGM 270 is listening and can communicate with it. A detector can transmit a field that activates the radio frequency identification transponders of the blood glucose monitors packed in a crate to determine if any of them were incorrectly packed and therefore to avoid shipping errors.

In accordance with an exemplary embodiment of the present invention, a means for automatically determining the association of a diagnostic test performed by an individual to a mealtime is provided. The association of a diagnostic test to a mealtime is based on the timing of a therapeutic intervention performed by the individual. The present invention is directed to both an analytical process and the parameters used by the analytical process. The present invention is exemplified when determining, for a given blood glucose test, whether that test is taken prior to a meal or after a meal based on the timing of an associated insulin injection. Described below are two methods, that is a parameter-based method (FIG. 26) and an analytical method (FIG. 27), for automatically making this determination in accordance with exemplary embodiments of the present invention.

In the parameter-based method (FIG. 26), the determination relies on therapy data (e.g., insulin injections) as indicated by block 300 and diagnostic test data (e.g., blood glucose meter test results) as indicated by block 302 and their corresponding time stamps, as well as a set of parameters (block 304) provided by the individual as follows:

A single time representing the latest an individual would eat their first meal (M1);
  A single time representing the latest an individual would eat their second meal (M2);
  A single time representing the latest. an individual would eat their third meal (M3);
  A single time representing the latest an individual would go to sleep (S1); and
  A single time representing the latest an individual would test their blood glucose in the middle of the night. (N1).

In the parameter-based method, the determination also relies on a set of timing thresholds internal to the analysis as follows:

blood glucose test times that are less than or equal to 30 minutes before the injection time are categorized as before the meal (blocks 310 and 312);
  blood glucose test times that are greater than or equal to 90 minutes AND less than or equal to 180 minutes after the injection time are categorized as after the meal (blocks 314 and 320);
  blood glucose test times that are less than or equal to 45 minutes before the injection time AND are greater than or equal to 180 minutes after the previous injection time are categorized as before the meal (blocks 312 and 318); and
  blood glucose test times that are greater than or equal to 30 minutes after the injection time AND are less than or equal to 90 minutes after the injection time are categorized as unknown (blocks 316 and 322).

The allocation of values (block 308) in accordance with this exemplary embodiment of the present invention is as follows:

if the injection time is before M1 on a given day, that injection will be associated with the first meal of the day;
  if the injection time is after M1 and before M2 on a given day, that injection will be associated with the second meal of the day;
  if the injection time is after M2 and before M3 on a given day, that injection will be associated with the third meal of the day;
  if the injection time is after M3 and before S1 on a given day, that injection will be associated with the bedtime for that day; and if no injection time and the blood glucose test time is after N1 and before N1+5 on a given day, that blood glucose test will be associated with a nighttime test.

Contention between multiple tests is resolved in accordance with this exemplary embodiment of the present invention as follows: if two blood glucose tests are performed prior to an insulin injection, the blood glucose test closest in time to the injection time is used for the analysis. Based on these parameters, a data set of insulin injection times and blood glucose test times can be analyzed to determine the following, for example:

which blood glucose tests are associated with an injection; and
  whether the blood glucose test is categorized as a before meal test or an after meal test for three mealtimes, a bedtime test, or a nighttime test.

In the analysis-based method (FIG. 27), the determination relies on performing an analysis of the individual's data to determine:

the number of injections for each day; and
  the number of blood glucose tests for each day (block 330).

Additionally, the individual can provide a number representing the typical number of meals eaten per day (block 332).

Insulin injection times and blood glucose test times are examined to determine how the times cluster (block 334). This may be performed using average times and some measure of variation and confidence intervals around those times throughout the day, relative to the number of meals eaten per day (block 336). This provides a means to segment the day into mealtimes, bedtime, and nighttime. Once the values are segmented, the analysis proceeds as in the parameter-based method described above to determine whether a blood glucose test is before a meal or after a meal using the timing thresholds, that is:

blood glucose test times that are less than or equal to 30 minutes before the injection time are categorized as before the meal (blocks 310 and 318);
  blood glucose test times that are greater than or equal to 90 minutes AND less than or equal to 180 minutes after the injection time are categorized as after the meal (blocks 314 and 320);
  blood glucose test times that are less than or equal to 45 minutes before the injection time AND are greater than or equal to 180 minutes after the previous injection time are categorized as before the meal (blocks 312 and 318); and
  blood glucose test times that are greater than or equal to 30 minutes after the injection time AND are less than or equal to 90 minutes after the injection time are categorized as unknown (blocks 316 and 322).

This aspect of the present invention realizes a number of advantages and improvements over the prior art. In the past, the determination of mealtimes was wholly dependent on one of two conventional methods:

1. An individual assigning fixed times to their before and after meal time periods; and
2. An individual "marking" their data in such a way as to indicate whether a test or action occurred before or after a meal, at bedtime, or in the night. In the first conventional method, a problem occurs in that the fixed times cannot take into account variations in daily life that might change the timing of meals, bedtime, or a middle of the night event. As a result, data that are from a time period after a meal are misrepresented as having occurred before a meal and vice versa. In the conventional second method, a burden is placed on the individual to make an extra effort to categorize each event either for later analysis or retrospectively "marking" each value according to its category. It is unlikely that an individual will either spend the time to mark every event, or that they will remember to mark every event at the time it occurs. Further, if they perform the "marking" retrospectively, the accuracy of their recollection is diminished, thus diminishing the accuracy of the event allocation.

The exemplary embodiments of the present invention described in connection with FIGS. 26 and 27 solve problems encountered with these conventional methods. First, these embodiments use the timing of a therapy intervention that is typically associated with the period immediately before a meal or immediately before bedtime and uses its occurrence as a proxy for the mealtime or bedtime. Thus, the accuracy of these embodiments of the present invention are directly related to the accuracy of the time information for the therapy intervention. Accordingly, if the therapy intervention's timestamp is itself automated and more accurately determined, the manner by which these embodiments correctly categorize the diagnostic test's timing is improved. Secondly, these embodiments establish timing thresholds that provide the ability to determine the most likely physiologic relationship between the therapy intervention and the diagnostic test.

Figure 28:
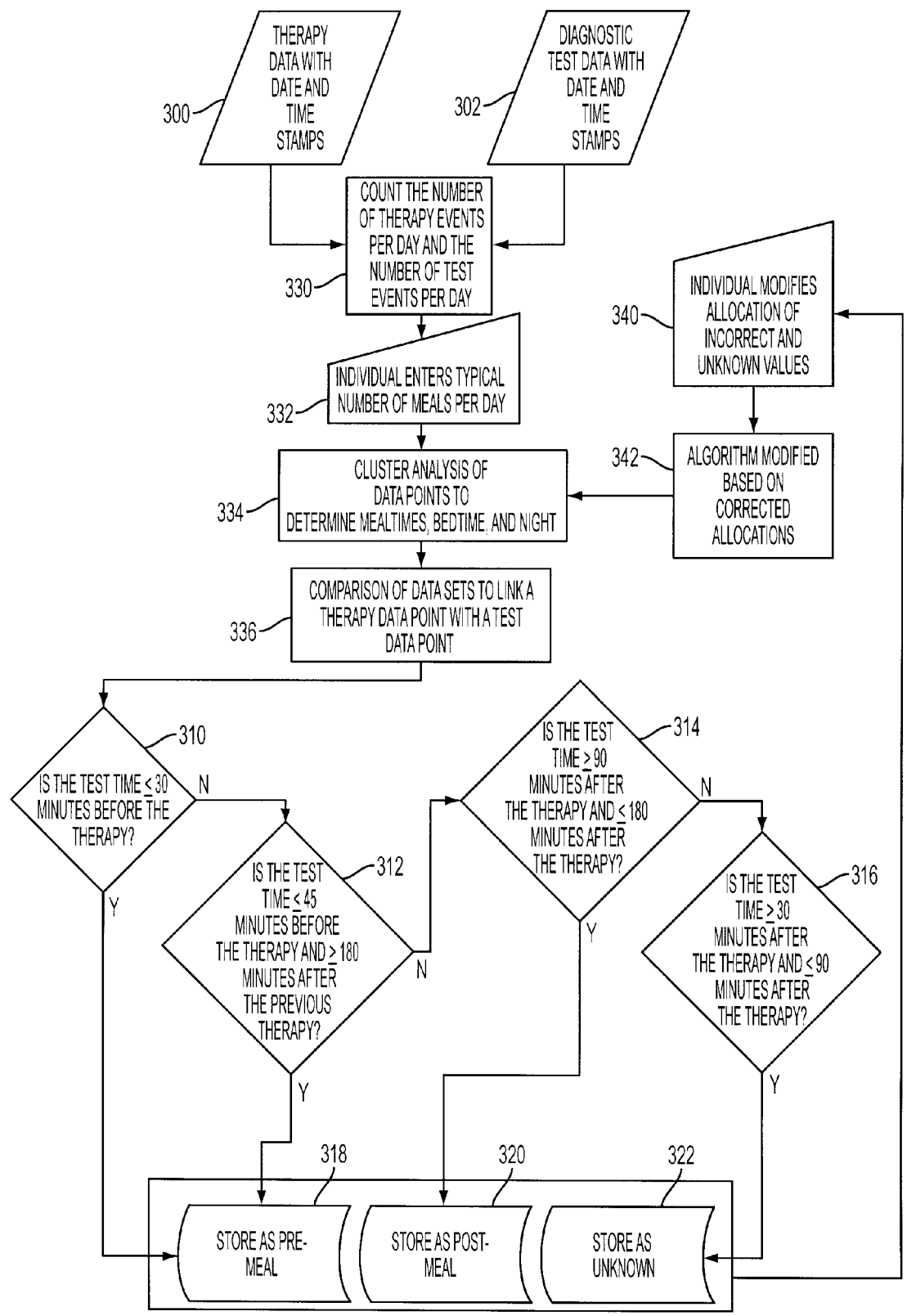
FIG. 28 is a process flow chart for an analysis-based approach with feedback loop for using therapy times to classify diagnostic test data in accordance with an exemplary embodiment of the present invention.

With reference to FIG. 28, a variation of the analysis-based embodiment described above is used with an analytic engine that contains an iterative learning algorithm that uses feedback from the individual to improve the accuracy of the categorizations over time. That is, with the initial dataset from an individual, the analytic engine can perform as described above, but the individual can then provide feedback in the form of corrections or changes to the categories defined by the engine (block 340). The analytic engine then incorporates this feedback into its algorithm and, on successive analyses, requires fewer corrections (block 342).

The underlying technical principle of this aspect of the present invention is a series of date and time comparisons that are performed on a dataset comprising two categories of values, where each value in each category has a unique date and time stamp. The first part of the approach compares the dates and times of the two categories of data to find close associations in time between data points. The second part of the approach is dependent on whether a parameter-based method (FIG. 26) is used or an analysis-based method (FIG. 27) is used. In general though, this part makes the assignment to categories of before or after meal, bedtime, or nighttime according to external parameters or to a statistical analysis of the dataset.

Figure 26:
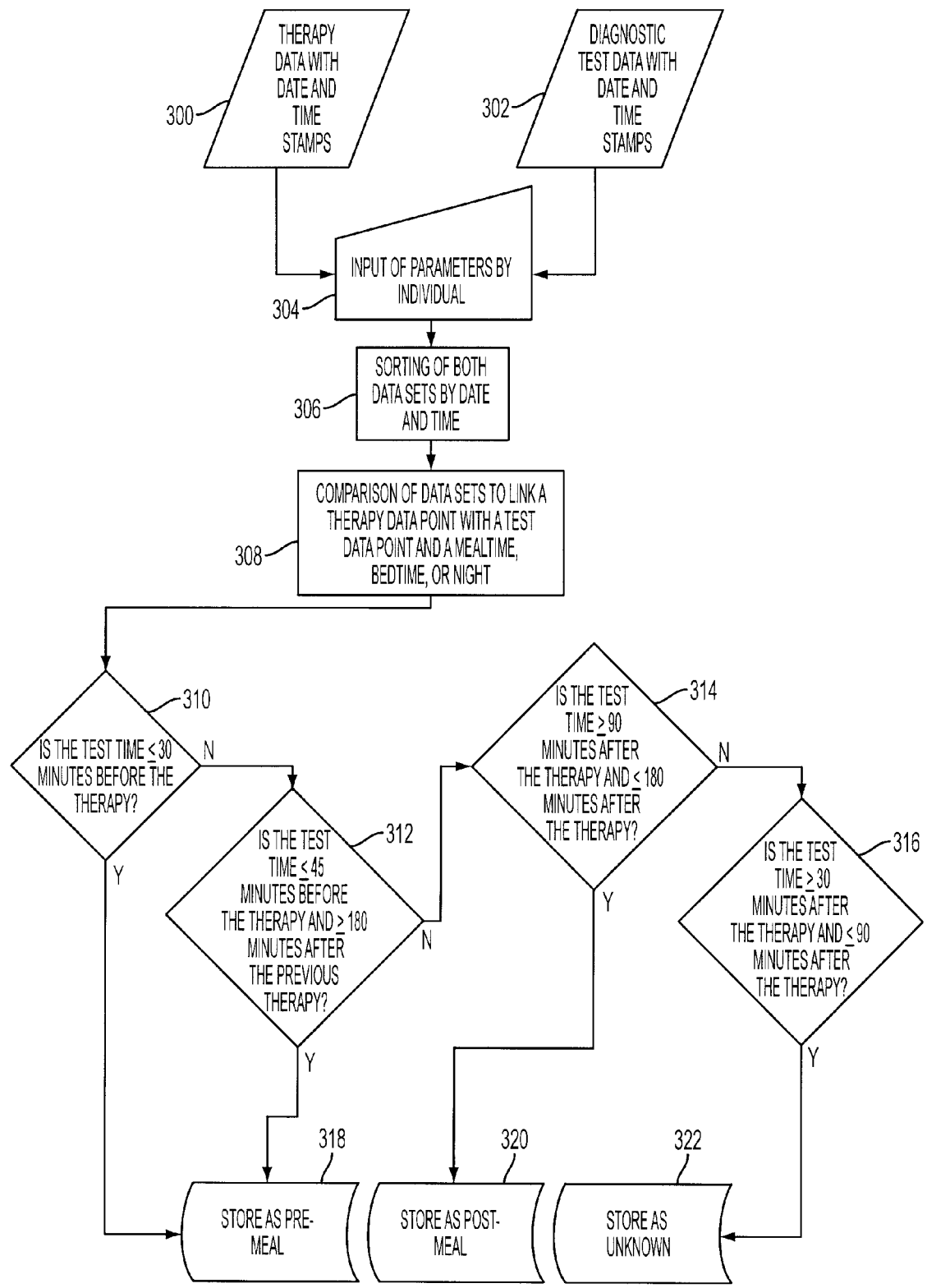
FIG. 26 is a process flow chart for a parameter-based approach for using therapy times to classify diagnostic test data in accordance with an exemplary embodiment of the present invention.
Figure 27:
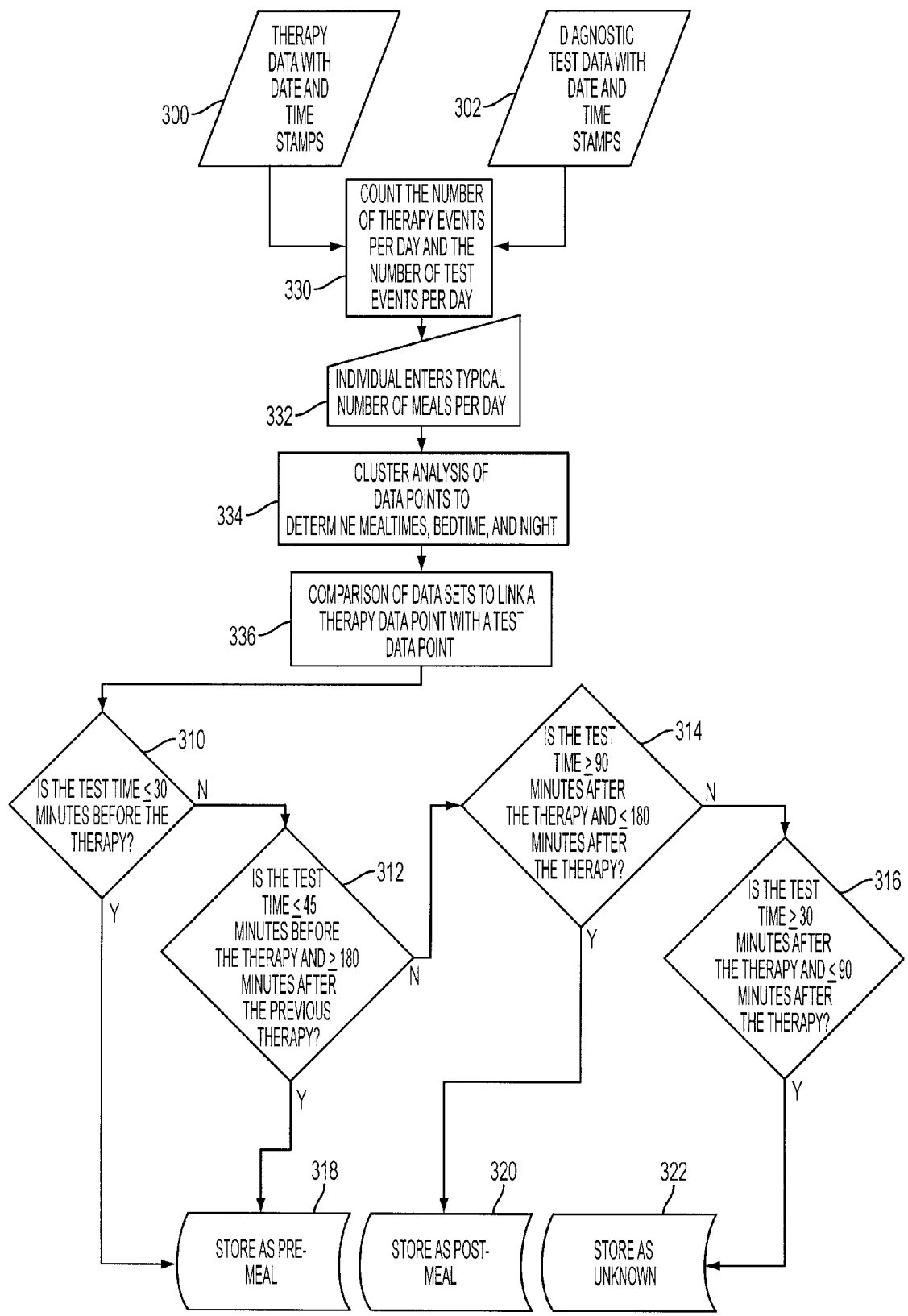
FIG. 27 is a process flow chart for an analysis-based approach for using therapy times to classify diagnostic test data in accordance with an exemplary embodiment of the present invention.

Fundamental to both methods of FIGS. 26 and 27 is the ability to establish timing thresholds that link the two categories of data or values. These timing thresholds would be based on clinical experience and physiologic data, or based on an analysis of an individual dataset over time. A related aspect of the present invention is the improvement in accuracy as the therapy intervention's date and timestamp accuracy improves, particularly if the therapy intervention's date and timestamp is automatically determined and stored in the dataset. The dataset (e.g., the two categories of data, and their associations in time), and the algorithm(s) for implementing the parameter-based or analysis-based methods, can be provided in repository or within the devices themselves. Placing the dataset and algorithm(s) in the repository 50 simplifies the device and realizes the advantages discussed above (e.g., reduced development time and therefore time to market, reduced complexity and therefore reduced potential for safety hazards, increased useable life of the device). In any event, the data in the repository 50 or within the devices themselves (e.g., meter 44) can be analyzed to abstract information about the patient's behaviors. This analysis can realize another advantage of improved messaging. In other words, the repository 50 can perform one or more algorithms to determine when messages such as alerts and educational messages should be sent to patients. A patient's test results, insulin intake and mealtimes can be analyzed to determine an optimal time at which to send a reminder message to the patient to take a test or administer insulin or schedule a physician's office visit, for example. Also, algorithmic processing of the repository 50 contents can affect the determination of a patient's readiness and willingness to receive information to that will optimally impact a change in that patient's behavior and his or her diabetes management practices.

Another benefit is that with a device (e.g., meter 44) that has an "always on" wireless connection, sophisticated firmware in the devices is no longer needed for performing analytical operations. For example, many BGM devices today provide BG averages, or graphical trend data, and so on. With the kinds of systems described herein in accordance with exemplary embodiments of the present invention, the devices (e.g., meters 44, 142 and 148) need not have any of these analytical capabilities, but rather merely act as display devices for the analytics performed at the repository level. In this way, the devices become less complex, which provides a number of benefits (e.g., reduced development time and therefore time to market; reduced complexity and therefore reduced potential for safety hazards, increased useable life of the device because software "upgrades" are performed at the repository level, not at the device level so devices do not have to be replaced, the ability to perform device firmware upgrades wirelessly without requiring the device to be replaced.

Figure 29:
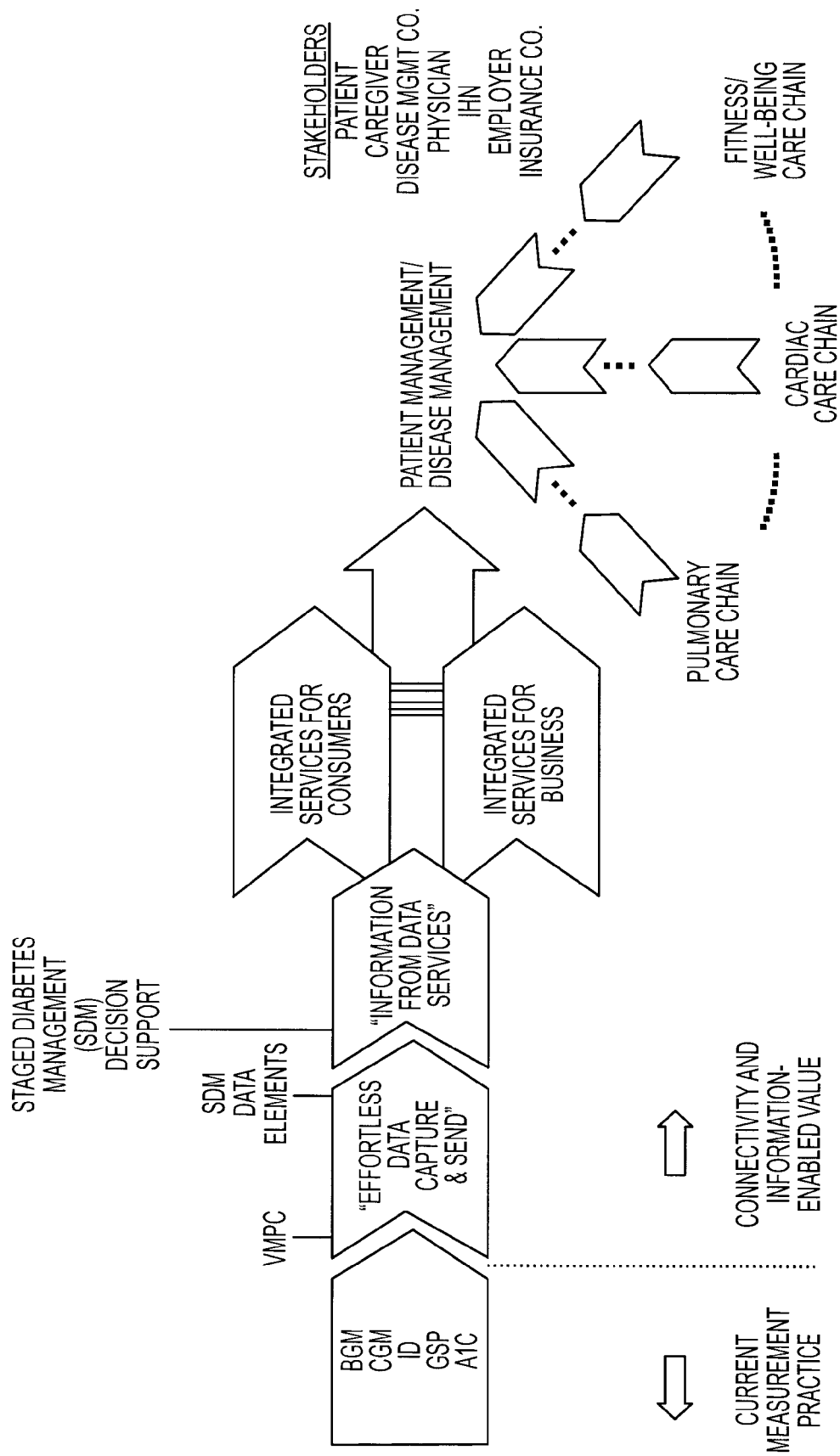
Figure 32:
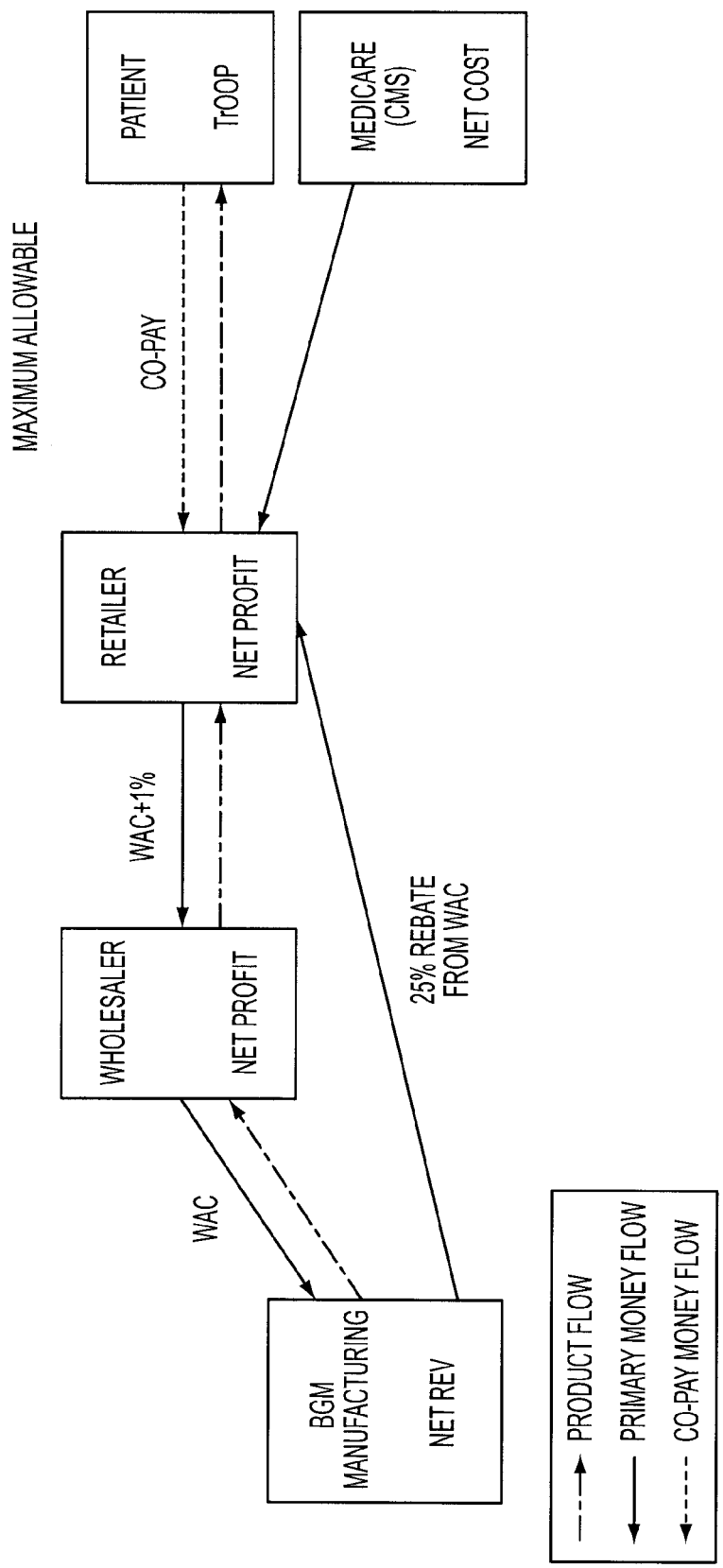
FIGS. 32 through 37 illustrate current cash flows between DM stakeholders that can be improved by exemplary embodiments of the present invention in the context of overall patient and disease management.
Figure 33:
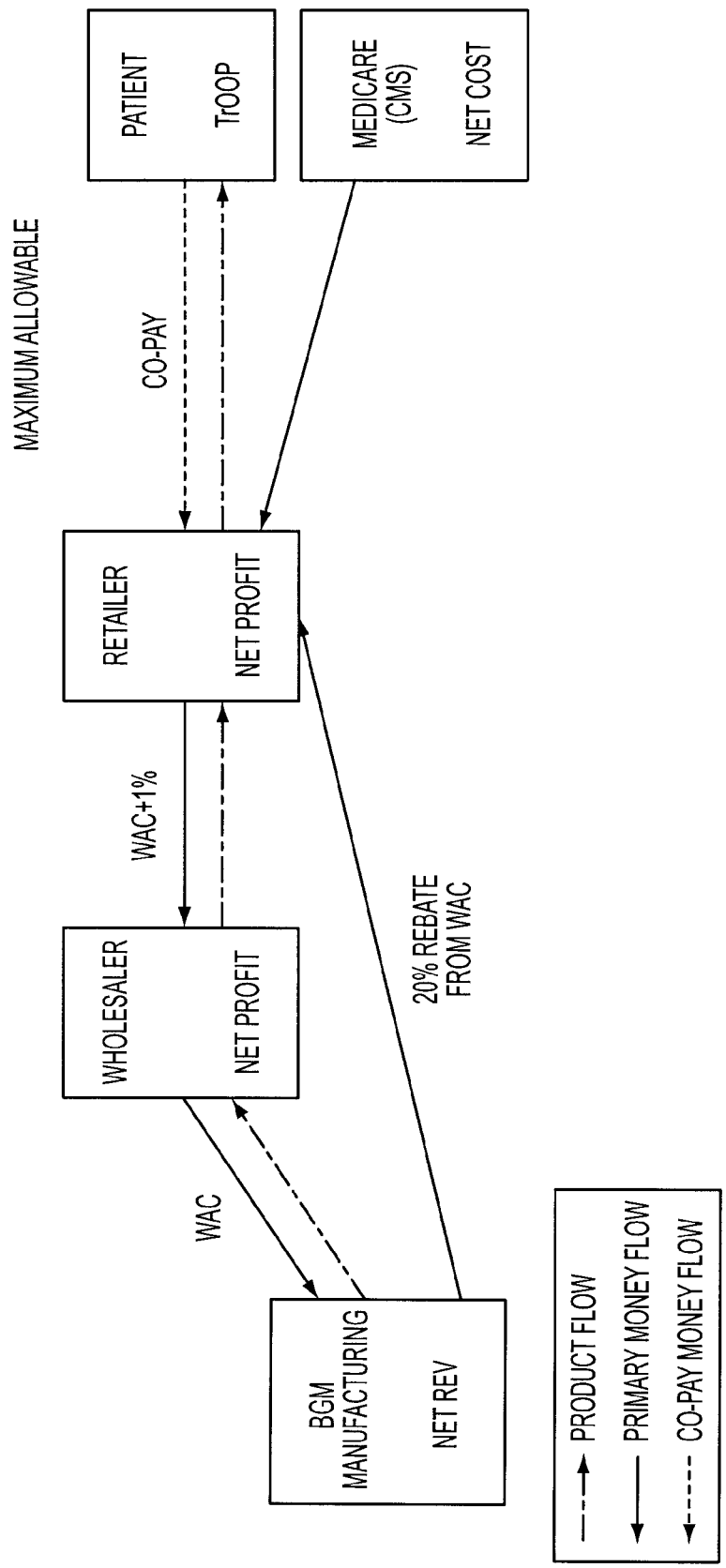

FIGS. 29-31 describe improved services and potential revenue benefits realized by the system of the present invention depicted in FIGS. 3 and 4 and described herein as exemplified in FIGS. 5a through 17. FIGS. 29, 30 and 31 illustrate the benefits of the connectivity and value added information provided by exemplary embodiments of the present invention in the context of overall patient and disease management.

As shown in FIG. 29, the left side of hashed line demarcates current measurement practices of different diagnostic data that is shared between a patient, a healthcare provider and other parties as described above in the background section. The right side of hashed line indicates advantages of the exemplary embodiments of the present invention. For example, the effortless data capture and send operations of the connected BGMs, continuous glucose monitors (CGMs) and insulin delivery devices and the "information from data" services provided using the repository 50, as described herein in accordance with exemplary embodiments of the present invention, provide integrated services for both customers and businesses including, but not limited to, patients, caregivers, DMCs, healthcare providers, integrated health networks (IHNs), employers and insurance companies. In addition to diabetes, the patient management and disease management services provided by the exemplary embodiments of the present invention are useful for different types of healthcare conditions including, but not limited to, pulmonary care, cardiac care, fitness/well-being care. Examples are provided in FIGS. 30 and 31 such as a diabetes nurse educator (DNE) tracking hundreds of patients through a repository portal and noting that certain patients need immediate attention.

Figure 34:
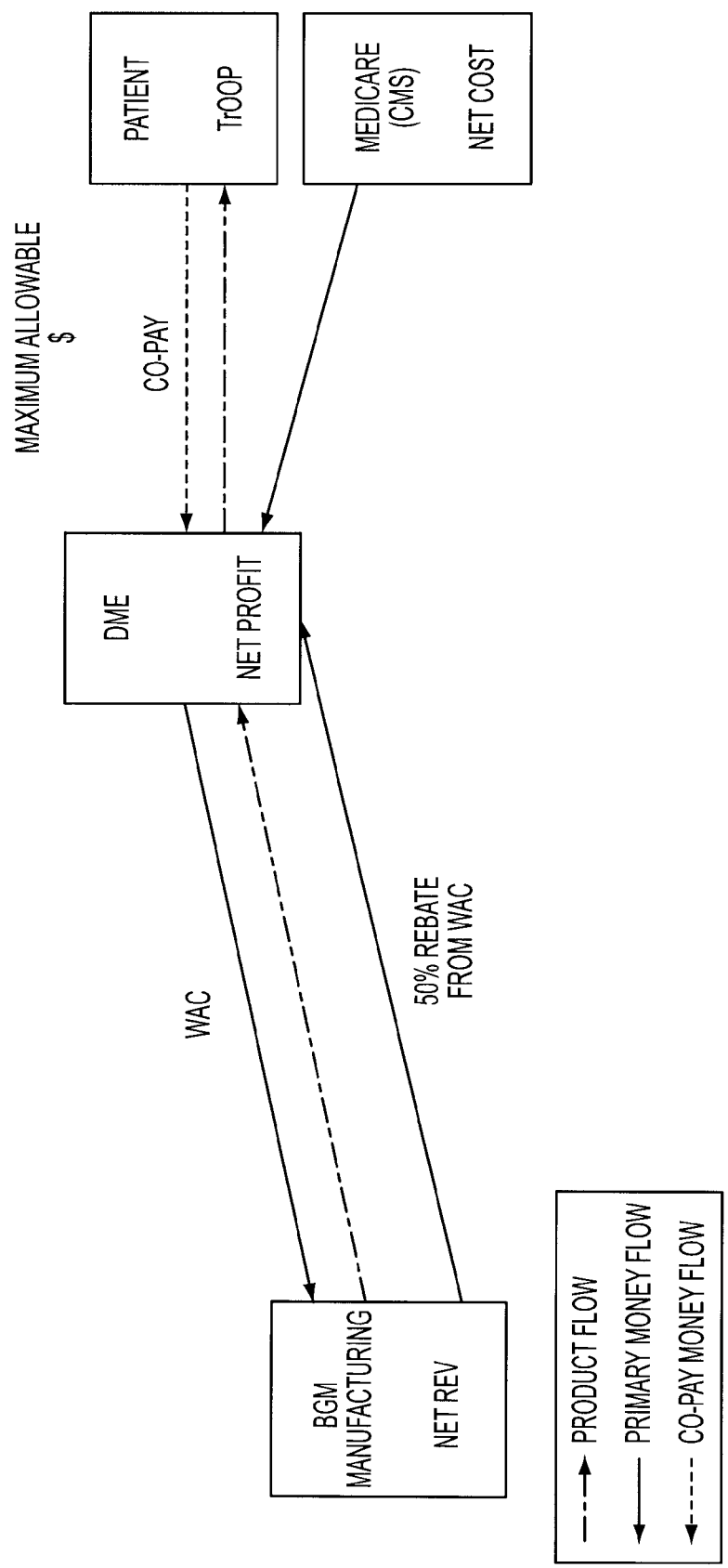
Figure 35:
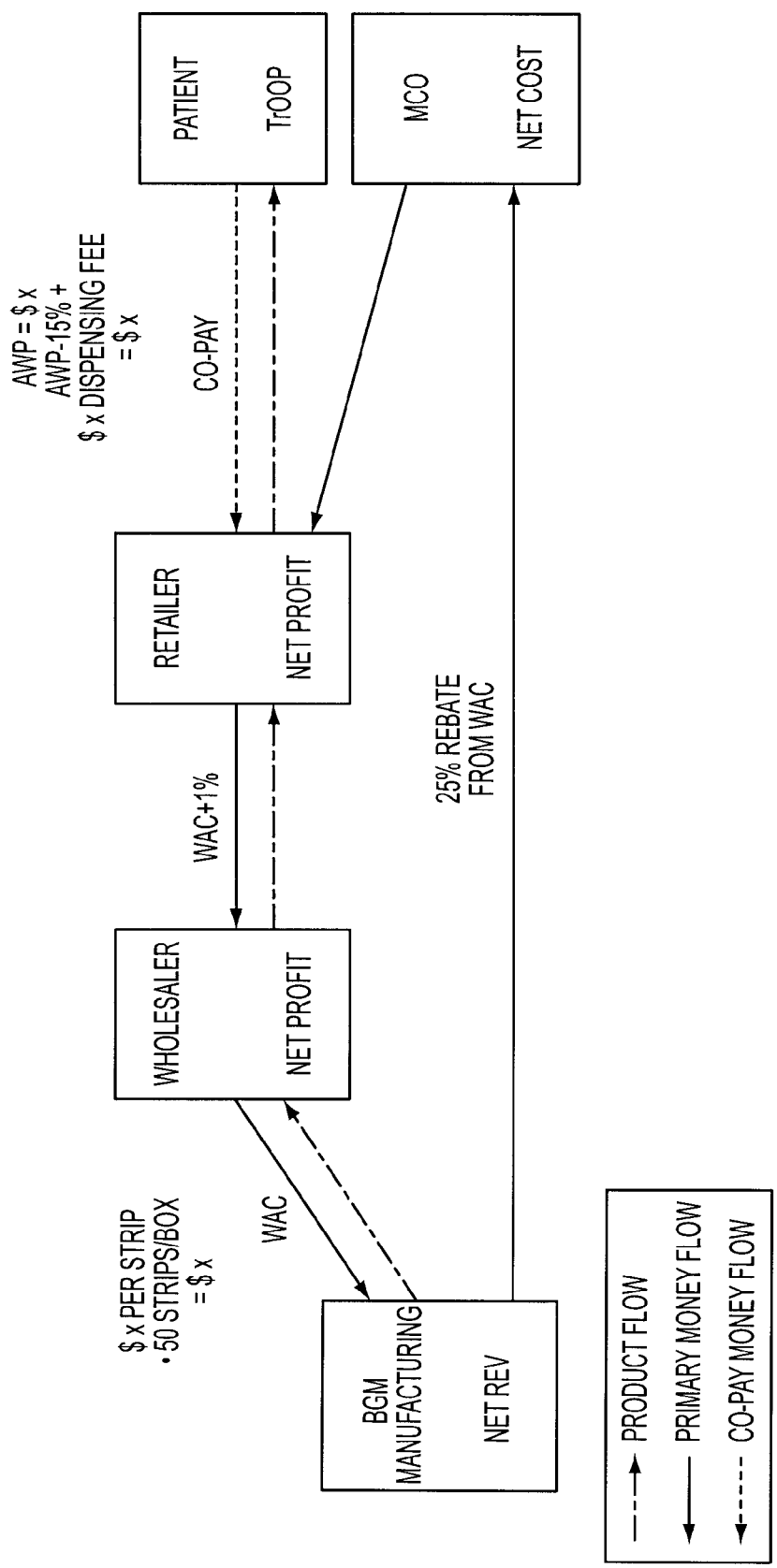
Figure 36:
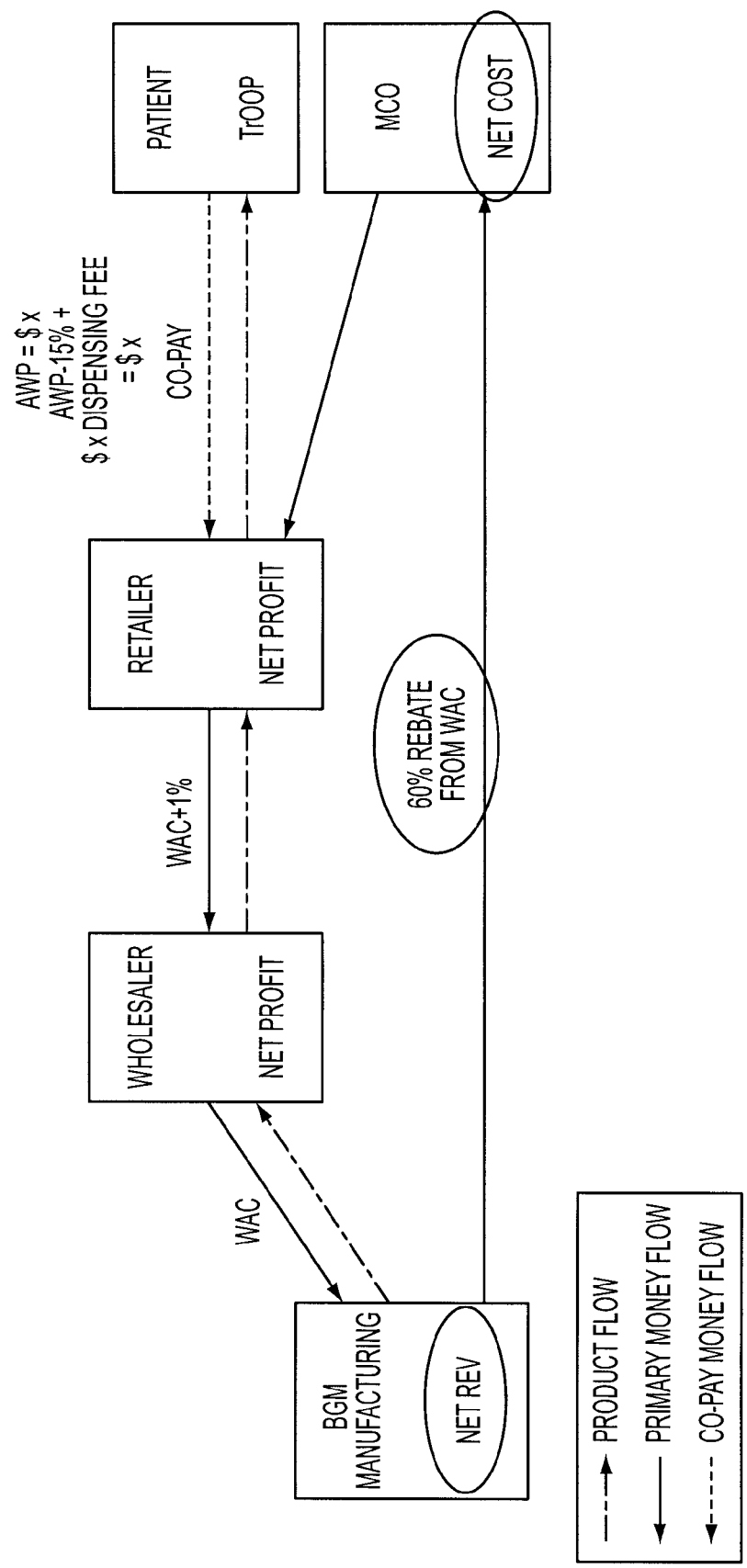
Figure 37:
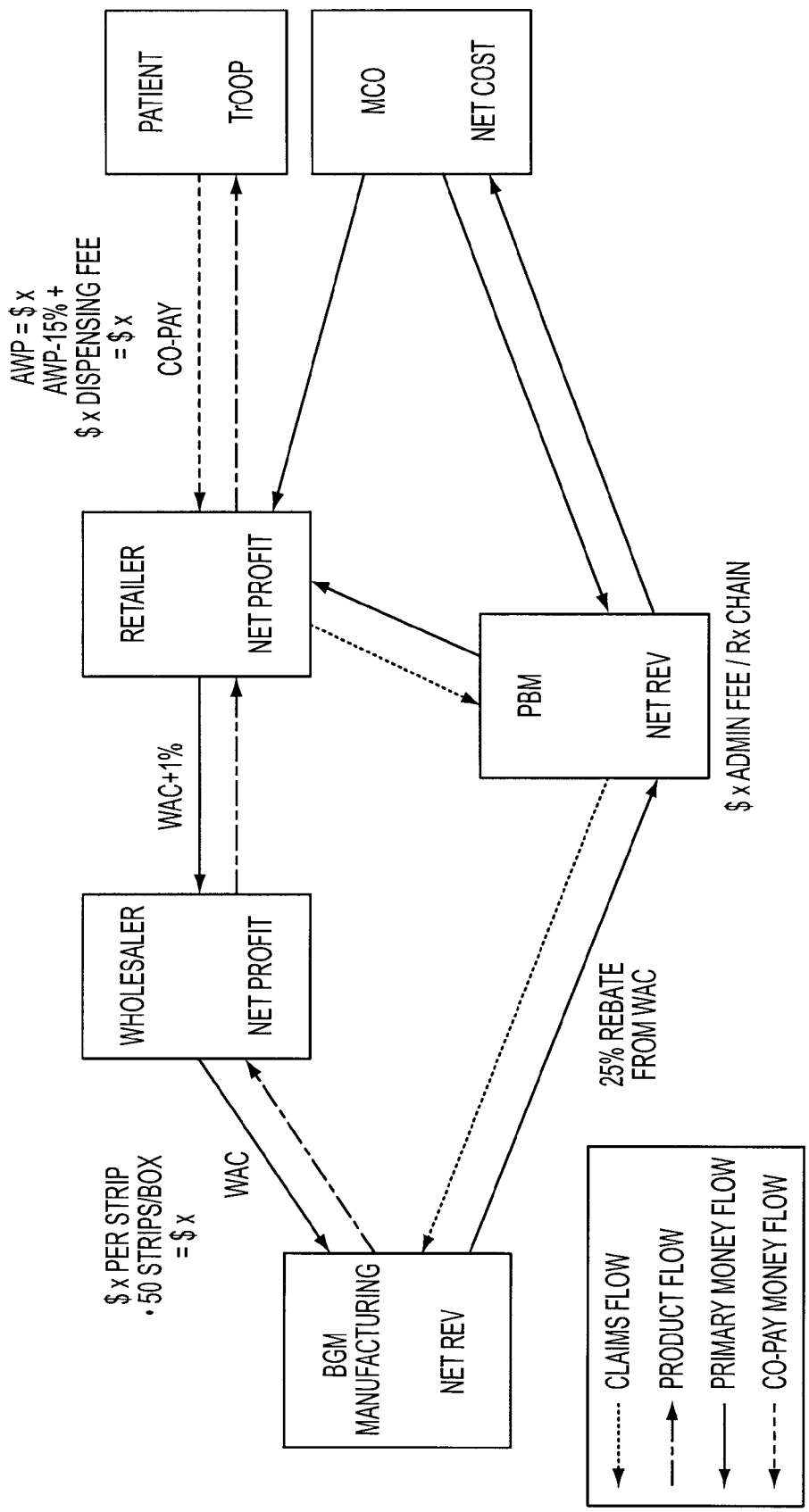

FIGS. 32-37 illustrate retail money flow advantages provided by exemplary embodiments of the present invention. For example, FIGS. 32 and 33 each illustrate product flow such as test strips from a BGM manufacturer to a patient via a wholesaler and retailer, and revenue flow between these parties. FIGS. 35 and 36 illustrate similar parties except for a third party payer such as a managed care organization in lieu of Medicare. FIG. 37 also includes a pharmacy benefits manager (PBM). FIG. 34 illustrates product flow from a BGM manufacturer to a patient via a durable medical equipment supplier or DME, and revenue flow between these parties. The accurate test result reporting, proactive disease counseling, test strip tracking and other advantages of the exemplary embodiments of the present invention provide the additional benefit of significant cost savings and therefore can allow for rebates as shown.

Figure 38:
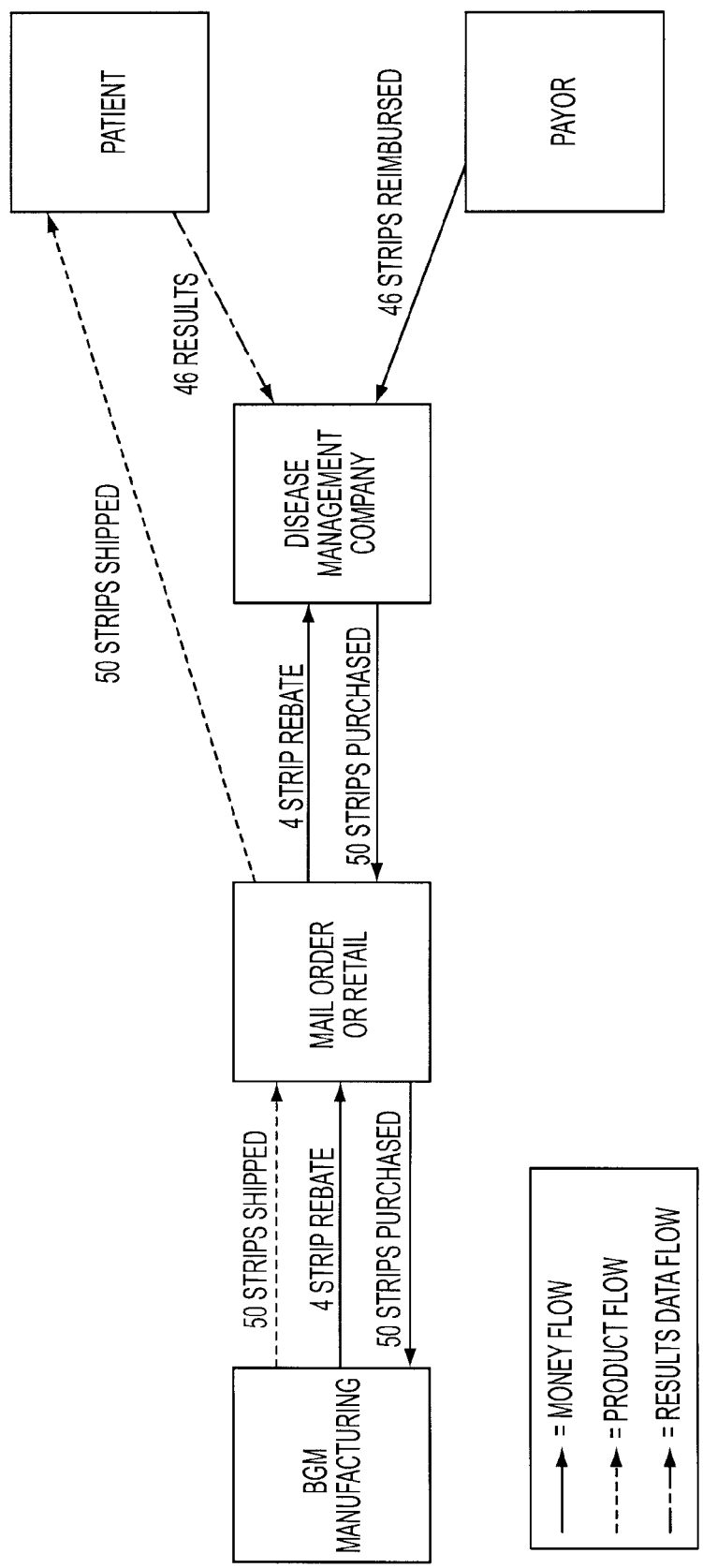
FIGS. 38, 39 and 40 illustrate improvement over current cash flows between DM stakeholders afforded by a pay-for-results model implemented in accordance with an exemplary embodiment of the present invention.
Figure 39:
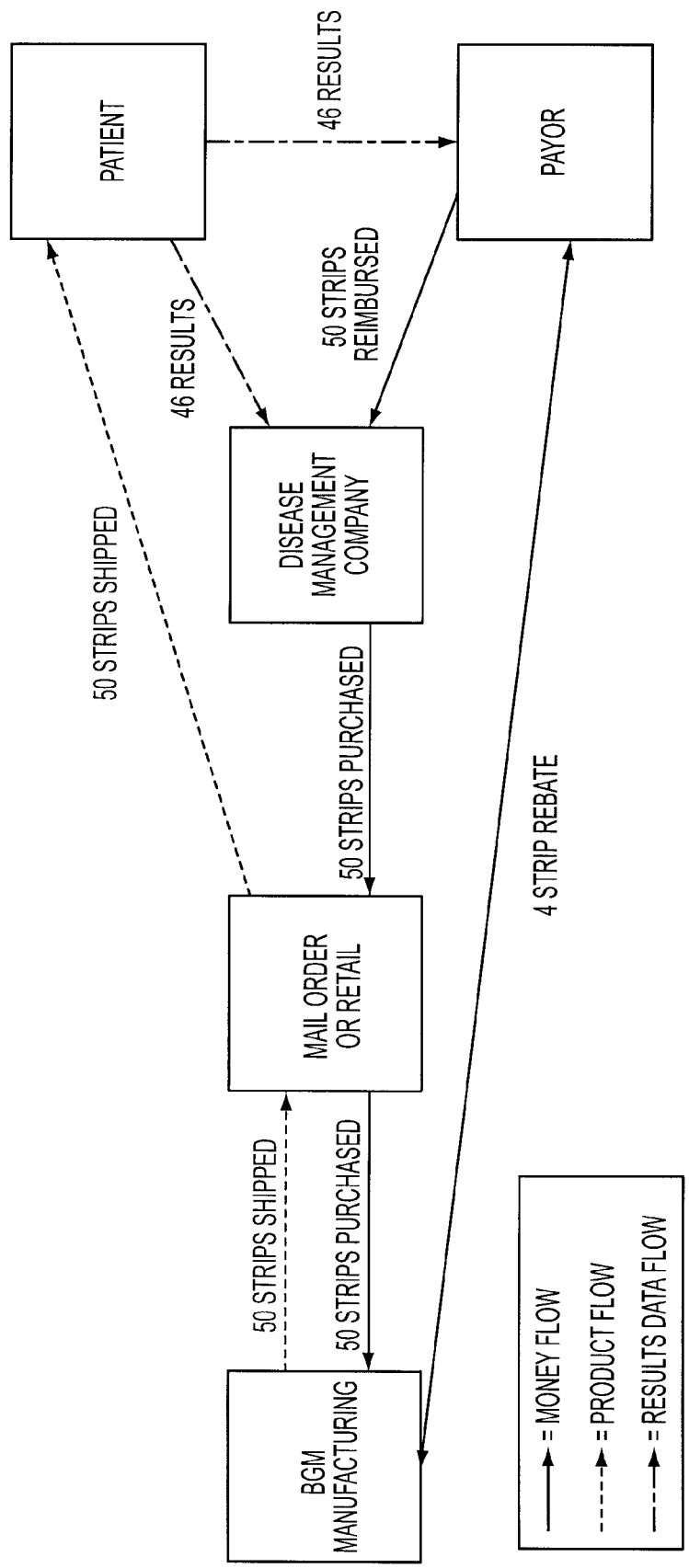
Figure 40:
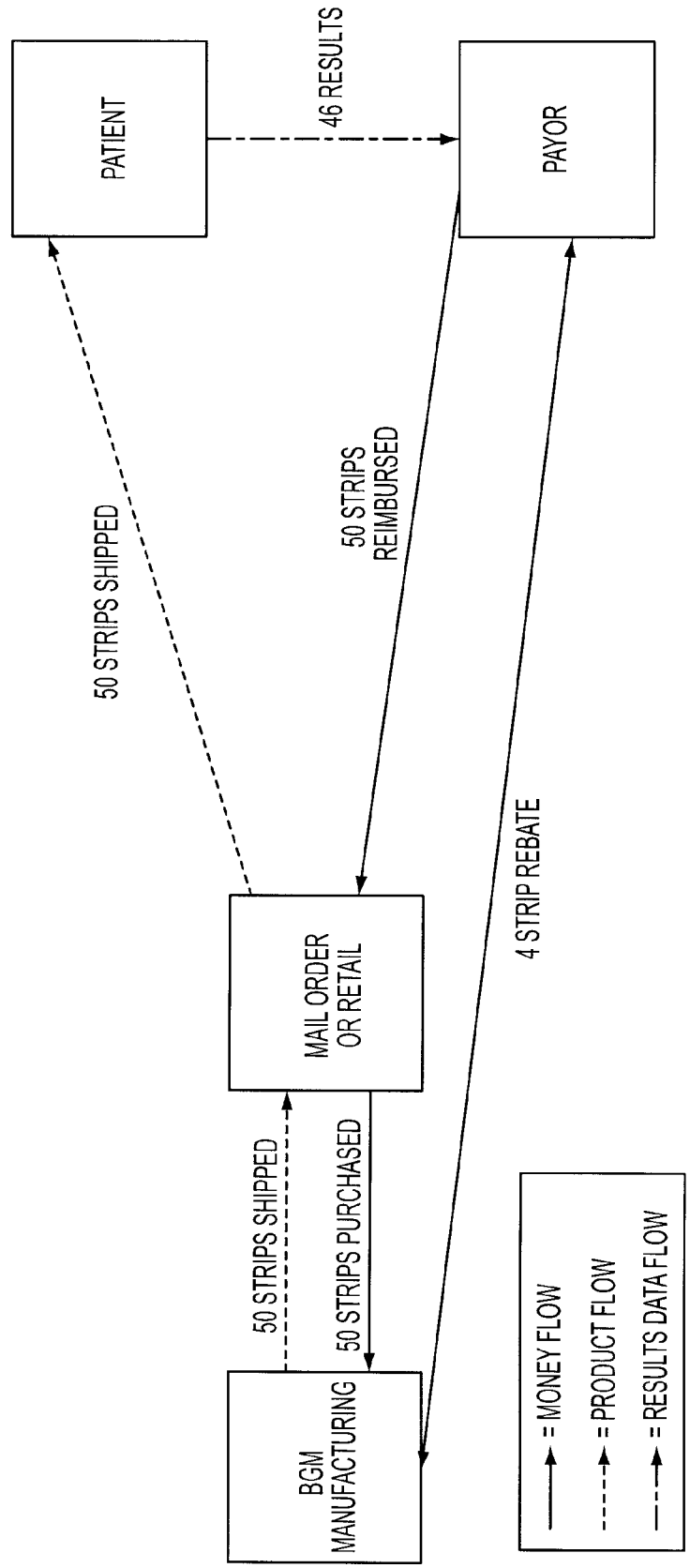

FIGS. 38, 39 and 40 illustrate improvement over current cash flows between DM stakeholders afforded by a pay-for-results model implemented in accordance with an exemplary embodiment of the present invention such as determining actual use of test strips. As shown in FIG. 38, a disease management company can determine from an order in the repository 50 that a patient should receive 50 test strips per month based on their current prescribed testing frequency. A mail order or retail vendor can purchase 50 strips from a BGM manufacturer and ship them to the patient and bill the DMC. The DMC and/or payor can, in turn, determine from the repository that only 46 test strips were used by the patient during a selected period of time as determined using the method described above in accordance an exemplary embodiment of the present invention. The payor need only pay for 46 test strips. The DMC and/or payor can receive a rebate for the 4 unused test strips.

Figure 41D:
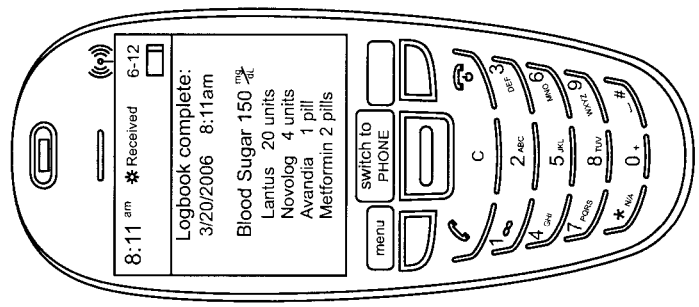
FIGS. 41A, 41B, 41C and 41D each illustrate a blood glucose monitor with a display message in accordance with an exemplary embodiment of the present invention.
Figure 41C:
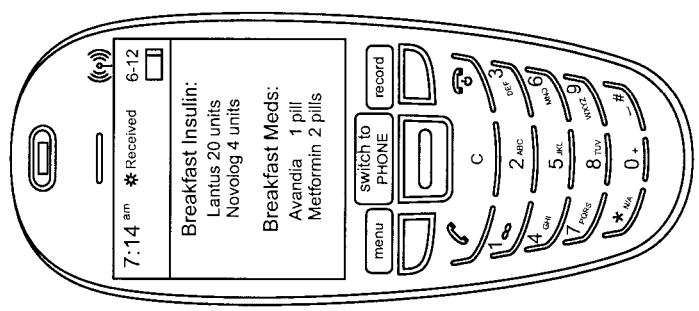
Figure 41B:
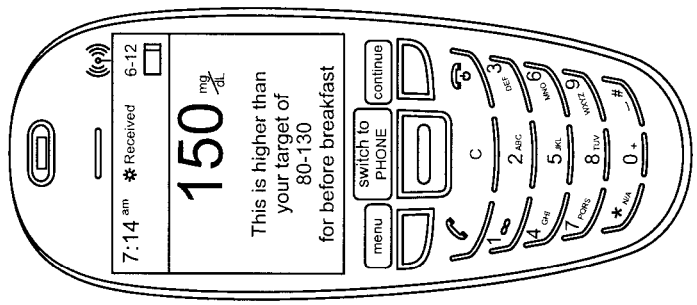
Figure 41A:
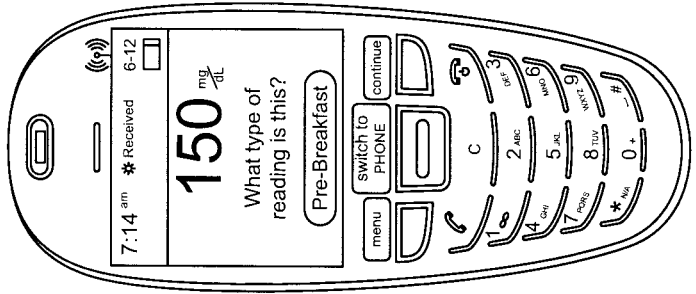

FIGS. 41A through 41D, 42 and 43 illustrate additional advantages of the connected disease management devices and data capture and analyses methods described herein with reference to exemplary embodiments of the present invention. FIG. 41D illustrates how the system illustrated in FIG. 3 collects data such as blood glucose level, date and time, among other optional data such as pre-meal and post-meal readings. As shown in FIG. 41B, a user is given real-time feedback based on information analyzed in the repository 50 (e.g., ADA target or physician prescribed target values for blood glucose levels). As shown in FIG. 41C, the data in the repository can be used to calculate a required insulin dose or other medication that can be transmitted to the BGM to prompt users to take required medication level. With reference to FIG. 41D, the testing and dosage data, among other information such as nutrition and pre-meal or post-meal blood glucose levels, is stored in the repository 50 for use by various stakeholders such as a patient, healthcare provider, DMC and so on. As shown in FIG. 42, the data can be collected, analyzed and summarized in a display screen for a number of patients to more effectively manage diabetes patient populations. The display screen can include recent readings, averages over a selected number of days and insulin dose compliance that is color coded or shaded to enhance identification of patients whose ranges or readings are high, low or within a target range. As show in FIG. 43, the data for a selected patient can be captured on a display screen as a one-page action plan with additional information such as blood glucose averages over time.

It is to be understood that the exemplary embodiments of the present invention described herein can be embodied as computer-readable codes on a computer-readable recording medium. The computer-readable recording medium is any data storage device that can store data which can thereafter be read by a computer system. Examples of the computer-readable recording medium include, but are not limited to, read-only memory (ROM), random-access memory (RAM), CD-ROMs, magnetic tapes, floppy disks, optical data storage devices, and carrier waves (such as data transmission through the Internet via wired or wireless transmission paths). The computer-readable recording medium can also be distributed over network-coupled computer systems so that the computer-readable code is stored and executed in a distributed fashion. Also, functional programs, codes, and code segments for accomplishing the present invention can be easily construed as within the scope of the invention by programmers skilled in the art to which the present invention pertains.

While certain exemplary embodiments of the invention have been shown and described herein with reference to certain preferred embodiments thereof, it will be understood by those skilled in the art that various changes in form and details may be made therein without departing from the spirit and scope of the invention as defined by the appended claims and their equivalents.

What is claimed is:

1. A computer-implemented method of determining test strip and insulin usage comprising:
    storing testing data for a plurality of patients in a repository, the testing data comprising for respective patients at least one of the number of recommended tests per day and the number of test strips allotted to the patient via one of a supplier and an insurer according to their respective prescriptions for testing;
    automatically, without user involvement, transmitting test results from a blood glucose meter to the repository in response to detection of an event selected from the group consisting of telephone activation if the blood glucose meter is built into or connected to a cellular telephone configured to communicate with the repository wirelessly, and selected motion activation of the blood glucose meter, the test results comprising measured glucose level;
    analyzing, using the computer, the testing data and the test results stored in the repository for at least a selected one of the patients to determine at least one of the number of test strips actually used by the patient within a selected time period and the number of allotted test strips that are unused within a selected time period;
    storing, at the repository, prescription data indicating insulin allotted to patients according to their respective prescriptions for insulin;
    automatically, without user involvement, transmitting to the repository delivery data relating to insulin delivered by an insulin delivery device in response to detection of complete insulin delivery;
    analyzing, using the computer, the stored prescription data and the delivery data stored at the repository that corresponds to insulin delivered by the insulin delivery device over a selected period of time to determine if a prescribed patient supply of insulin requires replenishment; and
    generating an output indicative of at least one of a number of the allotted test strips determined to be actually used or determined to remain unused, and an order for more insulin when the prescribed patient supply of insulin is determined to require replenishment.

2. The method as claimed in claim 1, further comprising automatically generating a refill prescription for test strips if the number of test strips actually used by the patient is determined to indicate that a selected ratio of the number of test strips allotted to the patient remain unused.

3. The method as claimed in claim 1, further comprising generating an estimate of when the patient is going to be out of test strips and automatically sending more test strips to the patient when a selected number of test strips allotted to the patient are determined to remain unused.

4. The method as claimed in claim 1, further comprising billing at least one of an insurer and healthcare payor for test strips based on the number of test strips determined to be actually used by the patient.

5. The method as claimed in claim 1, further comprising:
    analyzing the testing data and the test results stored in the repository to identify selected ones of the patients having selected glucose levels based on their corresponding test results; and
    transmitting at least one of a promotion, educational information and an incentive to the selected ones of the patients.

6. The method as claimed in claim 5, wherein the transmitting further comprises:
    analyzing the testing data and the test results stored in the repository to identify selected ones of the patients having at least one of selected health profiles based on their corresponding test results; and
    selling advertising to vendors for transmission to the selected ones of the patients as potential consumers for new diabetes management products.

7. The method as claimed in claim 1, wherein the repository stores meter calibration data for the blood glucose meter, and further comprising:
    analyzing the test results and the meter calibration data stored in the repository to determine whether the blood glucose meter is malfunctioning; and
    transmitting an alert when the blood glucose meter is determined to be malfunctioning.

8. The method as claimed in claim 1, wherein the testing data further comprises at least one of date of test strip manufacture, test strip expiration date, lot number, calibration data, manufacturer identification, and logistic information comprising distribution country or region, and further comprising:
    analyzing the test results and the testing data stored in the repository to determine whether any of the test strips are defective;
    transmitting at least one of an alert to the patient when any of the test strips are determined to be defective, and an alert advising a vendor to send the patient more test strips to replace the test strips determined to be defective.

9. A computer-implemented method of determining glucose sensor and insulin usage comprising:
    storing testing data for a plurality of patients in a repository, the testing data comprising for respective patients at least the number of recommended tests per day according to their respective prescriptions for testing;
    automatically, without user involvement, transmitting test results from a blood glucose meter to the repository in response to detection an event selected from the group consisting of telephone activation if the blood glucose meter is built into or connected to a cellular telephone configured to communicate with the repository wirelessly, selected pressure activation of the blood glucose meter, and selected motion activation of the blood glucose meter, the test results comprising measured glucose level;

analyzing, using the computer, the testing data and the test results stored in the repository for at least a selected one of the patients to determine the number of times a glucose sensor was actually used by the patient within a selected time period;

storing, at the repository, prescription data indicating insulin allotted to patients according to their respective prescriptions for insulin;

automatically, without user involvement, transmitting to the repository delivery data relating to insulin delivered by an insulin delivery device in response to detection of complete insulin delivery;

analyzing, using the computer, the stored prescription data and the delivery data stored at the repository that corresponds to insulin delivered by the insulin delivery device over a selected period of time to determine if a prescribed patient supply of insulin requires replenishment; and generating an output indicative of at least one of the number of times the glucose sensor was determined to be used, and an order for more insulin when the prescribed patient supply of insulin is determined to require replenishment.

10. The method as claimed in claim 9, wherein the glucose sensor is an insertable continuous glucose monitor sensor, and further comprising automatically sending a new glucose sensor to the patient if the number of times the glucose sensor was actually used by the patient is determined to be a selected non-zero integer number.

11. The method as claimed in claim 1 or 9, further comprising:
storing device data at an insulin delivery device, the device data comprising at least one of an insulin delivery device identification number, insulin-type and amount of insulin delivered via the insulin delivery device, the insulin delivery device comprising at least one of a syringe, a microneedle, a pump and an insulin pen, and being configured to deliver insulin; and
transmitting, to the repository, delivery data relating to insulin that was delivered by the insulin delivery device to the patient and comprising device data.

12. The method of claim 11, wherein the insulin delivery device comprises an RFID tag configured to transmit an insulin delivery device identification number corresponding to the insulin delivery device and to store the insulin delivery device data, and further comprising:
activating the RFID tag via an RFID reader in a blood glucose meter to collect at least the device data; and
wirelessly communicating the delivery data to the repository automatically and substantially in real-time without user involvement in response to the activating.

13. The method of claim 12, wherein the device data in the RFID tag comprises at least one of insulin-type delivered via the insulin delivery device, dosage, time stamp of delivery, and an identifier for at least one of the insulin delivery device, the blood glucose meter and the patient.

14. The method of claim 12, further comprising transmitting, via the blood glucose meter, the delivery data to the repository substantially coincidentally with a blood glucose testing event.

15. The method of claim 12, further comprising transmitting, via the blood glucose meter, the delivery data to the repository via at least one of a cellular network and the internet.

16. The method of claim 12, further comprising:
storing at the repository insulin delivery device identification numbers that uniquely identify corresponding insulin delivery devices; and
tracking via the repository the usage of respective ones of the insulin delivery devices.

17. The method of claim 12, further comprising transmitting the delivery data to the repository in response to the activating the RFID tag and detection of complete insulin delivery.

18. The method of claim 11, wherein the delivery data comprises multiple dose information.

19. The method of claim 12, further comprising:
storing multiple dose information at the insulin delivery device; and
transmitting the multiple dose information to the repository in response to the activating the RFID tag.

20. The method of claim 11, wherein the transmitting by the insulin delivery device comprises scanning available wireless frequencies and selecting a protocol based on optimal transmission qualities of a scanned frequency to communicate with the repository using at least one of a plurality of wireless protocols.

21. The method of claim 12, further comprising automatically transmitting at least one of blood glucose test data and the delivery data to the repository based on detection of at least one of the activating via the RFID reader, test strip reading, blood glucose measurement, detected motion, telephone activation when the blood glucose meter is connected to a cellular telephone, pressure activation, activation based on time, completion of insulin delivery, and repository instruction.

22. The method as claimed in claim 1, further comprising at least one of
automatically refilling a prescription for test strips if the number of test strips actually used by the patient is determined to be a selected ratio of the number of test strips allotted to the patient, and
generating an estimate of when the patient is going to be out of test strips and automatically sending more test strips to the patient when a selected number of test strips allotted to the patient are determined to remain unused.

23. The method as claimed in claim 22, wherein the automatically refilling comprises a vendor sending refills to the patient, and further comprising:
determining that a prescribed number of test results for the patient has not been received at the repository during a selected time period; and
transmitting a message to the vendor to send no more refills to the patient until the prescribed number of test results for the patient are received at the repository.

24. The method as claimed in claim 1, further comprising:
transmitting, to a third party payor, the determined number of test strips actually used by the patient; and
billing the third party payor on the basis of determined number of test strips that have actually been used.

25. The method as claimed in claim 1, further comprising determining compensation of a manufacturer of the test strips by at least one of a wholesaler and retailer that provide test strips to the respective patients for whom the testing data and the test results are stored in the repository, the determined compensation being at least wholesale acquisition cost (WAC) for the determined number of test strips that have actually been used by the respective patients.

26. The method as claimed in claim 25, further comprising determining a rebate for the third party payor that is less than the WAC and based on the determined number of test strips that have actually been used by the respective patients.

27. The method as claimed in claim 1, further comprising:
determining compensation of a manufacturer of the test strips by a wholesaler or retailer that provides test strips to the respective patients for whom the testing data and the test results are stored in the repository, the determined compensation of the manufacturer being for a selected number of test strips shipped to the wholesaler or retailer;
determining the reimbursement amount of the wholesaler or retailer by a third party payor to be for the selected number of test strips shipped to the wholesaler or retailer; and
determining a rebate for the third party payor in the amount of the reimbursement amount less compensation corresponding to the number of test strips determined to have actually been used by the respective patients based on their test results stored in the repository.

28. The method of claim 1, further comprising:
analyzing, for at least one selected patient, information in the repository comprising at least one of the testing data, the test results, the insulin delivery device data, and the data relating to the insulin delivered by the insulin delivery device, to generate real-time feedback for the patient;
transmitting the feedback to the blood glucose meter for display, the feedback comprising at least one of a calculated insulin dose, a prompt to medicate, and an indication of current blood glucose level relative to prescribed target values for blood glucose levels.

29. The method of claim 28, further comprising:
analyzing the information in the repository corresponding to a plurality of patients to generate a display screen indicating selected information for each of the plurality of patients comprising at least one of the test results for a selected time period, an average of the test results over a designated time period, and insulin dose compliance based on the data relating to the insulin delivered by the insulin delivery device; and
identifying the patients on the display screen whose information is above, below or within selected ranges using respective color coding or shading on the display screen.

* * * * *